(12) United States Patent
Hermann et al.

(10) Patent No.: US 7,862,496 B2
(45) Date of Patent: Jan. 4, 2011

(54) BRACHYTHERAPY APPARATUS AND METHODS FOR USING THEM

(75) Inventors: George D. Hermann, Portola Valley, CA (US); Eduardo Chi Sing, Dana Point, CA (US); Gail S. Lebovic, Frisco, TX (US); Mark A. Cole, Santa Ana, CA (US); Mark A. Ritchart, Murrieta, CA (US); Than Nguyen, Fountain Valley, CA (US)

(73) Assignee: Cianna Medical, Inc., Aliso Viejo, CA (US)

( * ) Notice: Subject to any disclaimer, the term of this patent is extended or adjusted under 35 U.S.C. 154(b) by 771 days.

(21) Appl. No.: 11/276,851

(22) Filed: Mar. 16, 2006

(65) Prior Publication Data
US 2007/0106108 A1 May 10, 2007

Related U.S. Application Data

(60) Provisional application No. 60/735,649, filed on Nov. 10, 2005.

(51) Int. Cl.
*A61N 5/00* (2006.01)
(52) U.S. Cl. .......................................................... 600/3
(58) Field of Classification Search .................. 600/1–8, 600/37; 602/79; 604/21, 104; 606/15, 49, 606/108, 159, 191, 194, 198
See application file for complete search history.

(56) References Cited

U.S. PATENT DOCUMENTS

| 3,060,924 A | 10/1962 | Rush |
| 3,750,653 A | 8/1973 | Simon |
| 3,968,803 A | 7/1976 | Hyman |
| 4,427,005 A | 1/1984 | Tener |
| 4,580,561 A | 4/1986 | Williamson |

(Continued)

FOREIGN PATENT DOCUMENTS

DE 3921291 1/1991

(Continued)

OTHER PUBLICATIONS

PCT International Search Report for PCT/US2006/060581, Applicant: BioLucent, Inc., Forms PCT/ISA/220 and PCT/ISA/210, dated May 3, 2007, 7 pages.

(Continued)

*Primary Examiner*—Samuel G Gilbert
(74) *Attorney, Agent, or Firm*—William A. English; Vista IP Law Group LLP

(57) ABSTRACT

Apparatus for delivering brachytherapy to a target tissue region includes an elongate body including a proximal end, a distal end sized for introduction into a tissue tract and carrying a plurality of elongate members including pathways for receiving a source of radiation. The elongate members are movable between collapsed and expanded configurations. During use, a tract is created through tissue, and the elongate body carrying the elongate members is advanced through the tract into a target location with the elongate members in the collapsed configuration. The elongate members are directed to the expanded configuration at the target location, and radiation is delivered to treat tissue at the target location, e.g., by introducing one or more radiation sources along the pathways.

59 Claims, 43 Drawing Sheets

U.S. PATENT DOCUMENTS

| | | | |
|---|---|---|---|
| 4,714,074 A | 12/1987 | Rey et al. | |
| 4,798,212 A | 1/1989 | Arana | |
| 4,936,823 A | 6/1990 | Colvin et al. | |
| 4,957,476 A | 9/1990 | Cano | |
| 4,976,680 A | 12/1990 | Hayman et al. | |
| 5,056,523 A | 10/1991 | Hotchkiss, Jr. et al. | |
| 5,106,360 A | 4/1992 | Ishiwara et al. | |
| 5,152,741 A | 10/1992 | Farnio | |
| 5,235,966 A | 8/1993 | Jamner | |
| 5,242,372 A | 9/1993 | Carol | |
| 5,279,565 A | 1/1994 | Klein et al. | |
| 5,302,168 A | 4/1994 | Hess | |
| 5,336,178 A | 8/1994 | Kaplan et al. | |
| 5,354,257 A | 10/1994 | Roubin et al. | |
| 5,411,466 A | 5/1995 | Hess | |
| 5,423,747 A | 6/1995 | Amano | |
| 5,429,605 A | 7/1995 | Fearnot | |
| 5,484,384 A | 1/1996 | Fearnot | |
| 5,503,613 A | 4/1996 | Weinberger | |
| 5,509,900 A | 4/1996 | Kirkman | |
| 5,538,502 A | 7/1996 | Johnstone | |
| 5,540,659 A | 7/1996 | Teirstein | |
| 5,611,767 A | 3/1997 | Williams | |
| 5,653,683 A | 8/1997 | D'Andrea | |
| 5,678,572 A | 10/1997 | Shaw et al. | |
| 5,707,332 A | 1/1998 | Weinberger | |
| 5,713,828 A | 2/1998 | Coniglione | |
| 5,720,717 A | 2/1998 | D'Andrea | |
| 5,730,698 A | 3/1998 | Fischell et al. | |
| 5,782,740 A | 7/1998 | Schneiderman | |
| 5,840,008 A | 11/1998 | Klein et al. | |
| 5,843,163 A | 12/1998 | Wall | |
| 5,851,171 A | 12/1998 | Gasson | |
| 5,863,284 A * | 1/1999 | Klein | 600/3 |
| 5,863,285 A * | 1/1999 | Coletti | 600/3 |
| 5,882,291 A | 3/1999 | Bradshaw et al. | |
| 5,891,091 A | 4/1999 | Teirstein | |
| 5,910,102 A | 6/1999 | Hastings | |
| 5,913,813 A | 6/1999 | Williams et al. | |
| 5,916,143 A | 6/1999 | Apple et al. | |
| 5,931,774 A | 8/1999 | Williams et al. | |
| 5,938,582 A | 8/1999 | Ciamacco, Jr. et al. | |
| 5,942,209 A | 8/1999 | Leavitt et al. | |
| 5,976,106 A | 11/1999 | Verin et al. | |
| 6,013,019 A * | 1/2000 | Fischell et al. | 600/3 |
| 6,022,308 A | 2/2000 | Williams | |
| 6,033,357 A | 3/2000 | Ciezki et al. | |
| 6,036,632 A | 3/2000 | Whitmore et al. | |
| 6,056,722 A | 5/2000 | Jayaraman | |
| 6,059,752 A | 5/2000 | Segal | |
| 6,071,263 A | 6/2000 | Kirkman | |
| 6,074,339 A | 6/2000 | Gambale et al. | |
| 6,083,148 A | 7/2000 | Williams | |
| 6,117,064 A | 9/2000 | Apple et al. | |
| 6,159,139 A | 12/2000 | Chiu | |
| 6,159,141 A | 12/2000 | Apple et al. | |
| 6,176,821 B1 | 1/2001 | Crocker et al. | |
| 6,179,766 B1 | 1/2001 | Dickerson | |
| 6,196,996 B1 | 3/2001 | Teirstein | |
| 6,200,256 B1 | 3/2001 | Weinberger | |
| 6,200,257 B1 | 3/2001 | Winkler | |
| 6,213,976 B1 | 4/2001 | Trerotola | |
| 6,217,585 B1 * | 4/2001 | Houser et al. | 606/108 |
| 6,221,003 B1 | 4/2001 | Sierocuk et al. | |
| 6,221,030 B1 | 4/2001 | Avaltroni | |
| 6,234,951 B1 | 5/2001 | Hastings | |
| 6,238,374 B1 | 5/2001 | Winkler | |
| 6,258,099 B1 | 7/2001 | Mareiro et al. | |
| 6,261,320 B1 | 7/2001 | Tam et al. | |
| 6,264,599 B1 | 7/2001 | Slater et al. | |
| 6,264,631 B1 | 7/2001 | Willis et al. | |
| 6,267,775 B1 | 7/2001 | Clerc et al. | |
| 6,287,249 B1 | 9/2001 | Tam et al. | |
| 6,338,709 B1 | 1/2002 | Geoffrion | |
| 6,358,195 B1 | 3/2002 | Green et al. | |
| 6,371,904 B1 | 4/2002 | Sirimanne et al. | |
| 6,413,204 B1 | 7/2002 | Winkler et al. | |
| 6,450,937 B1 * | 9/2002 | Mercereau et al. | 600/7 |
| 6,458,069 B1 | 10/2002 | Tam et al. | |
| 6,482,142 B1 | 11/2002 | Winkler et al. | |
| 6,482,178 B1 | 11/2002 | Andrews et al. | |
| 6,494,824 B1 | 12/2002 | Apple et al. | |
| 6,506,145 B1 | 1/2003 | Bradshaw et al. | |
| 6,508,784 B1 | 1/2003 | Shu | |
| 6,527,692 B1 | 3/2003 | Weinberger | |
| 6,527,693 B2 | 3/2003 | Munro, III et al. | |
| 6,540,656 B2 | 4/2003 | Fontayne | |
| 6,540,734 B1 | 4/2003 | Chiu et al. | |
| 6,554,757 B1 | 4/2003 | Geitz | |
| 6,582,353 B1 | 6/2003 | Hastings et al. | |
| 6,589,158 B2 | 7/2003 | Winkler | |
| 6,592,548 B2 | 7/2003 | Jayaraman | |
| 6,607,476 B1 | 8/2003 | Barnhart | |
| 6,607,478 B2 | 8/2003 | Williams | |
| 6,638,206 B2 | 10/2003 | Green et al. | |
| 6,641,518 B2 | 11/2003 | Wolfson et al. | |
| 6,645,135 B1 | 11/2003 | Bhat | |
| 6,648,811 B2 | 11/2003 | Sierocuk et al. | |
| 6,659,933 B2 | 12/2003 | Asano | |
| 6,673,006 B2 | 1/2004 | Winkler | |
| 6,676,667 B2 | 1/2004 | Mareiro et al. | |
| 6,685,619 B2 | 2/2004 | Halpern et al. | |
| 6,692,460 B1 | 2/2004 | Jayaraman | |
| 6,699,170 B1 | 3/2004 | Crocker et al. | |
| 6,746,465 B2 | 6/2004 | Diederich et al. | |
| 6,752,752 B2 | 6/2004 | Geitz | |
| 6,910,999 B2 | 6/2005 | Chin et al. | |
| 6,923,754 B2 | 8/2005 | Lubock | |
| 6,955,641 B2 | 10/2005 | Lubock | |
| 7,041,047 B2 | 5/2006 | Gellman et al. | |
| 7,056,276 B2 | 6/2006 | Nakano | |
| 7,273,445 B2 * | 9/2007 | Pulido et al. | 600/3 |
| 7,357,770 B1 | 4/2008 | Cutrer et al. | |
| 2001/0007071 A1 | 7/2001 | Koblish | |
| 2002/0016583 A1 | 2/2002 | Cragg | |
| 2002/0032359 A1 | 3/2002 | Geoffrion et al. | |
| 2002/0151879 A1 * | 10/2002 | Loeb | 606/15 |
| 2002/0165427 A1 | 11/2002 | Yachia et al. | |
| 2003/0092957 A1 | 5/2003 | Scott et al. | |
| 2003/0114878 A1 | 6/2003 | Diederich et al. | |
| 2003/0158515 A1 | 8/2003 | Gonzalez et al. | |
| 2003/0163017 A1 | 8/2003 | Tam et al. | |
| 2003/0236443 A1 | 12/2003 | Cespedes et al. | |
| 2004/0006305 A1 | 1/2004 | Hebert et al. | |
| 2004/0068231 A1 | 4/2004 | Blondeau | |
| 2004/0087828 A1 | 5/2004 | Green et al. | |
| 2004/0116767 A1 * | 6/2004 | Lebovic et al. | 600/7 |
| 2004/0127765 A1 | 7/2004 | Seiler et al. | |
| 2004/0260142 A1 | 12/2004 | Lovoi | |
| 2005/0061533 A1 | 3/2005 | Lovoi et al. | |
| 2005/0075662 A1 | 4/2005 | Pedersen et al. | |
| 2005/0080313 A1 | 4/2005 | Stewart et al. | |
| 2005/0090845 A1 | 4/2005 | Boyd | |
| 2005/0096647 A1 | 5/2005 | Steinke et al. | |
| 2005/0101823 A1 | 5/2005 | Linares et al. | |
| 2005/0101860 A1 | 5/2005 | Patrick et al. | |
| 2005/0124843 A1 | 6/2005 | Singh | |
| 2005/0182286 A1 | 8/2005 | Lubock | |
| 2005/0240074 A1 | 10/2005 | Lubock | |
| 2006/0015166 A1 | 1/2006 | Kindlein et al. | |
| 2006/0020156 A1 | 1/2006 | Shulka | |
| 2006/0094923 A1 | 5/2006 | Mate | |
| 2006/0100475 A1 * | 5/2006 | White et al. | 600/3 |
| 2006/0116546 A1 | 6/2006 | Eng | |

| | | | | | | |
|---|---|---|---|---|---|---|
| 2006/0173233 | A1 | 8/2006 | Lovoi | EP | 0955071 | 2/2004 |
| 2006/0173235 | A1 | 8/2006 | Lim et al. | EP | 1402922 A1 | 3/2004 |
| 2006/0184192 | A1 | 8/2006 | Markworth et al. | EP | 1405600 | 4/2004 |
| 2006/0199990 | A1 | 9/2006 | Rioux et al. | EP | 1428477 | 6/2004 |
| 2006/0235365 | A1 | 10/2006 | Terwilliger et al. | EP | 1568397 | 8/2005 |
| 2006/0258895 | A1 | 11/2006 | Maschke | WO | 00/59378 | 10/2000 |
| 2007/0106108 | A1 | 5/2007 | Hermann et al. | WO | 01/95808 | 12/2001 |
| 2007/0167667 | A1 | 7/2007 | Lubock et al. | WO | 03/077768 | 9/2003 |
| 2007/0191668 | A1 | 8/2007 | Lubock et al. | WO | 03/079907 | 10/2003 |
| | | | | WO | 2005037363 A | 4/2005 |

FOREIGN PATENT DOCUMENTS

| | | |
|---|---|---|
| DE | 3924291 | 1/1991 |
| DE | 3889635 | 9/1994 |
| DE | 69027361 | 1/1997 |
| DE | 69219427 | 1/1998 |
| DE | 69714973 | 4/2003 |
| DE | 69529618 | 12/2003 |
| DE | 69628820 | 5/2004 |
| EP | 0775505 A1 | 5/1997 |
| EP | 0906769 | 4/1999 |
| EP | 0955071 | 11/1999 |

OTHER PUBLICATIONS

PCT Written Opinion for PCT/US2006/060581, Applicant: BioLucent, Inc., Forms PCT/ISA/237, dated May 3, 2007, 8 pages.

PCT International Search Report for PCT/US2006/060581, Applicant: BioLucent, Inc., Forms PCT/220 and PCT/210, dated May 3, 2007, 7 pages.

PCT Written Opinion for PCT/US2006/060581, Applicant: BioLucent, Inc., Forms PCT/ISA/237, dated May 3, 2007, 8 pages.

* cited by examiner

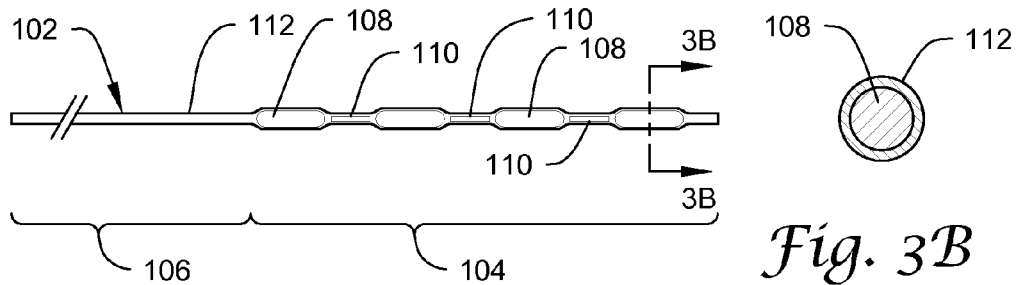
*Fig. 3A*
*Fig. 3B*
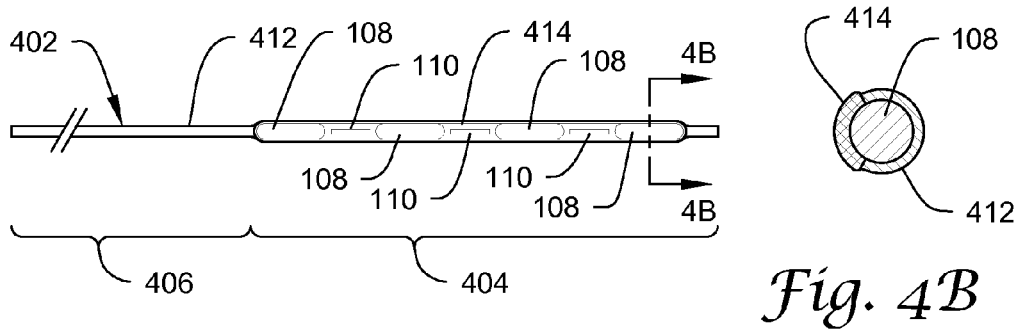
*Fig. 4A*
*Fig. 4B*
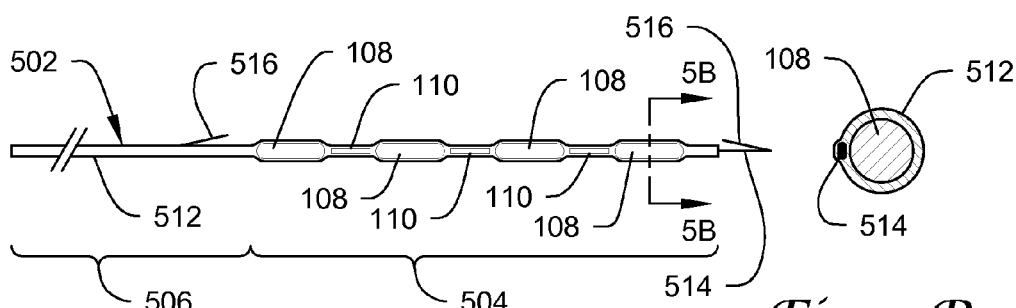
*Fig. 5A*
*Fig. 5B*
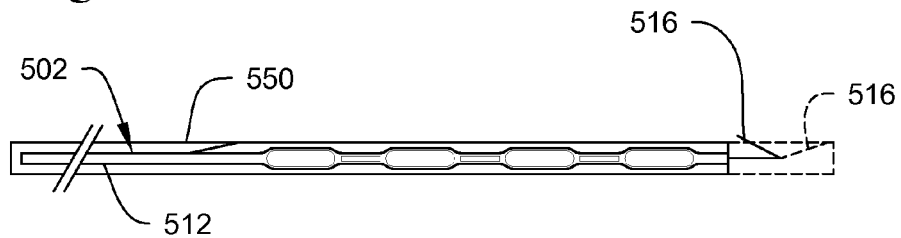
*Fig. 5C*

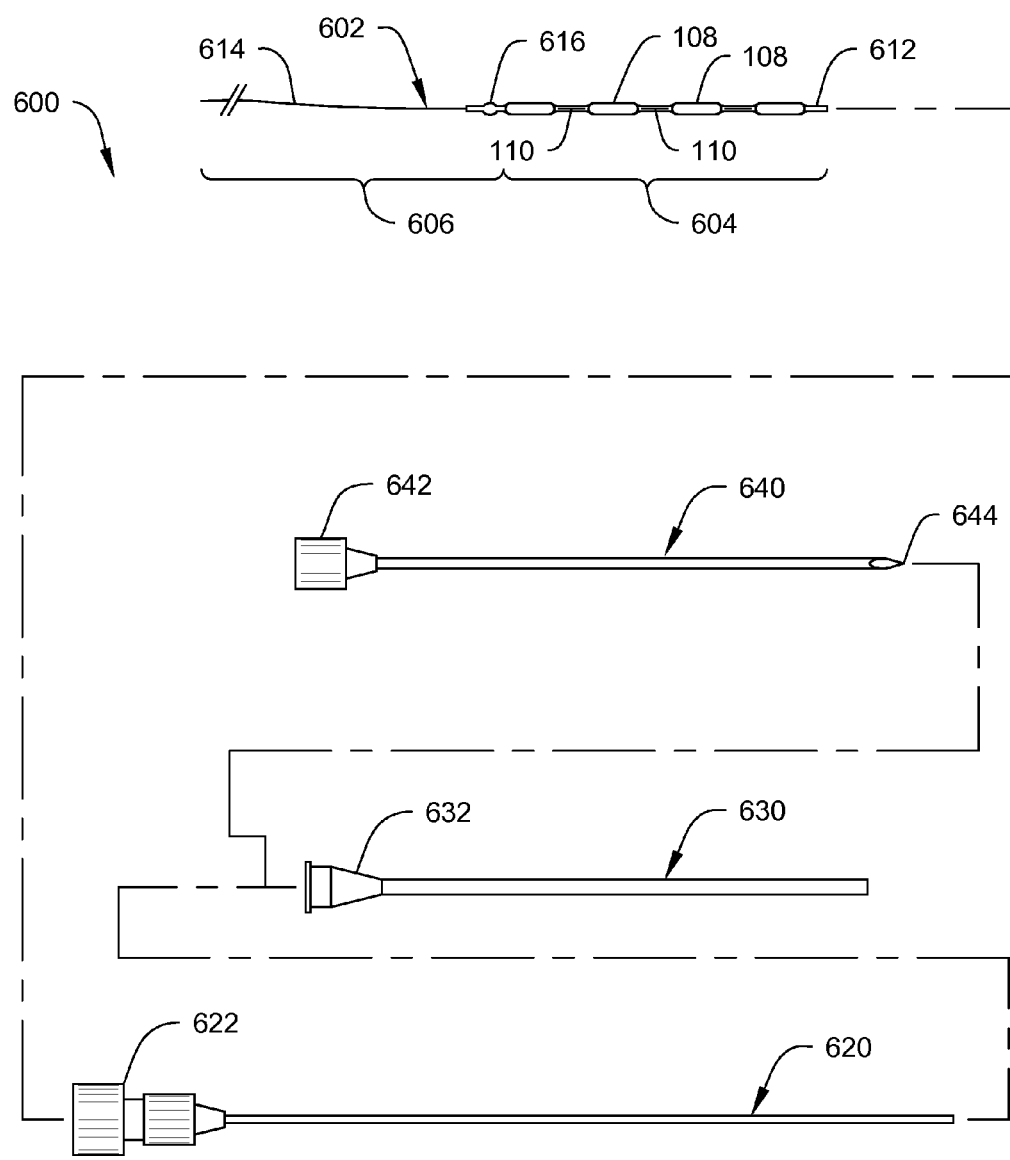

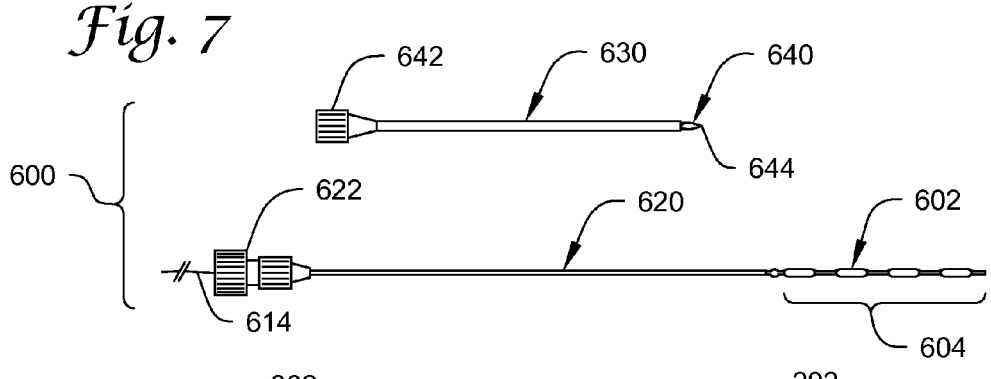
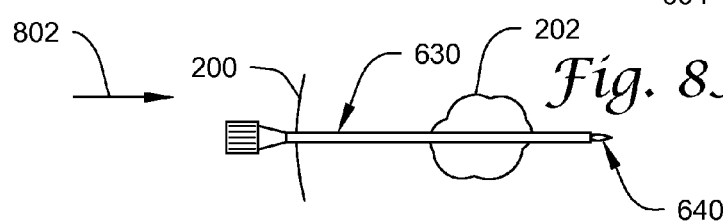
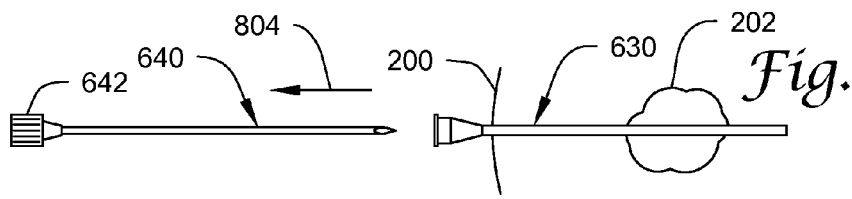
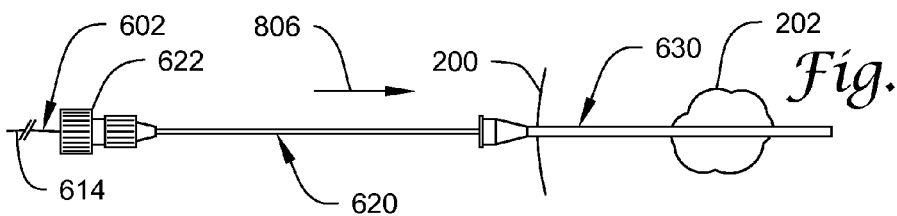
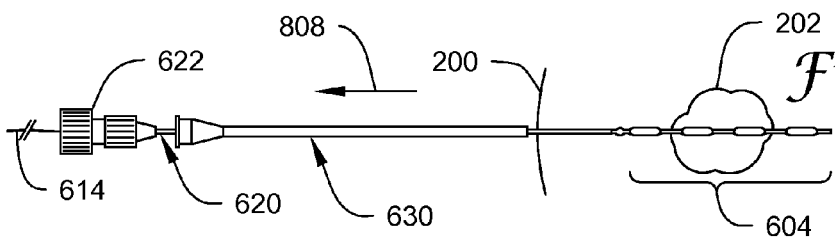
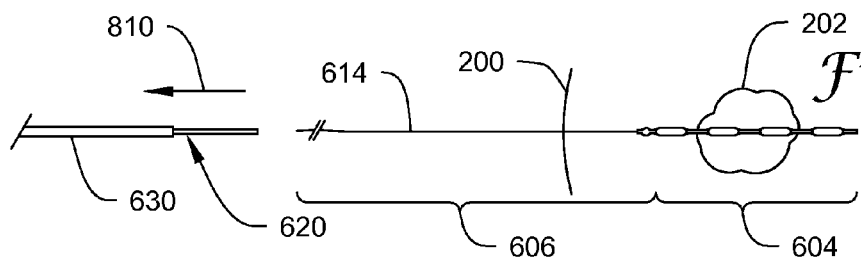

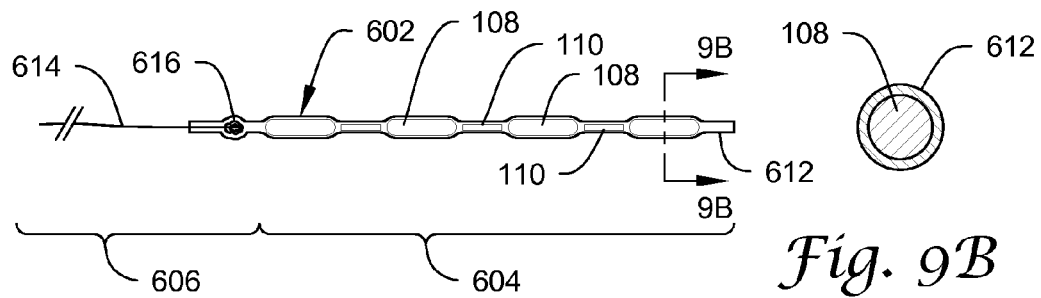
Fig. 9A
Fig. 9B
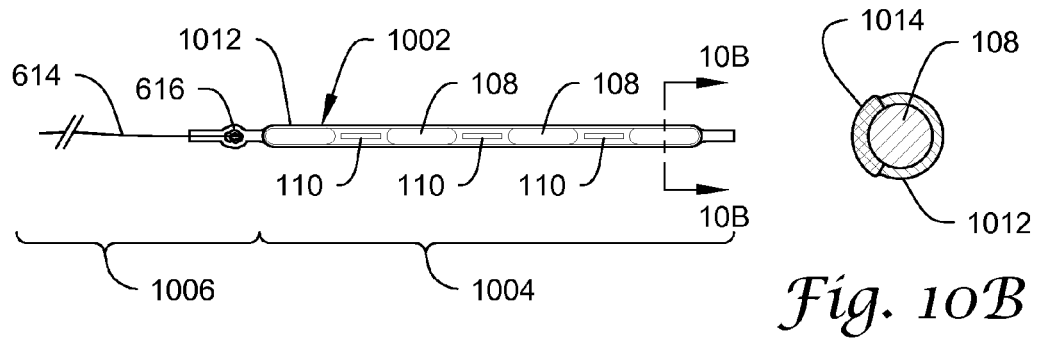
Fig. 10A
Fig. 10B
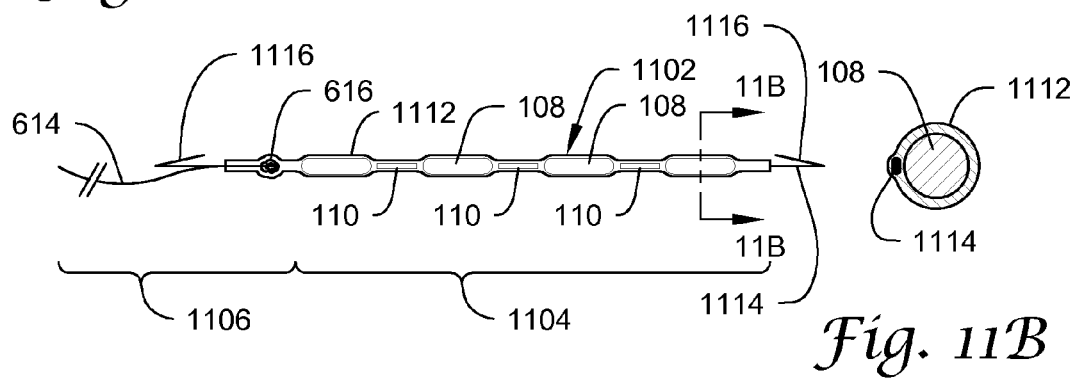
Fig. 11A
Fig. 11B

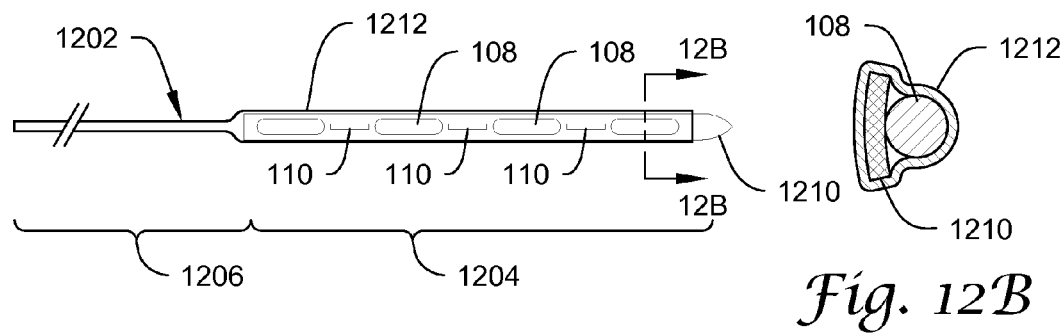
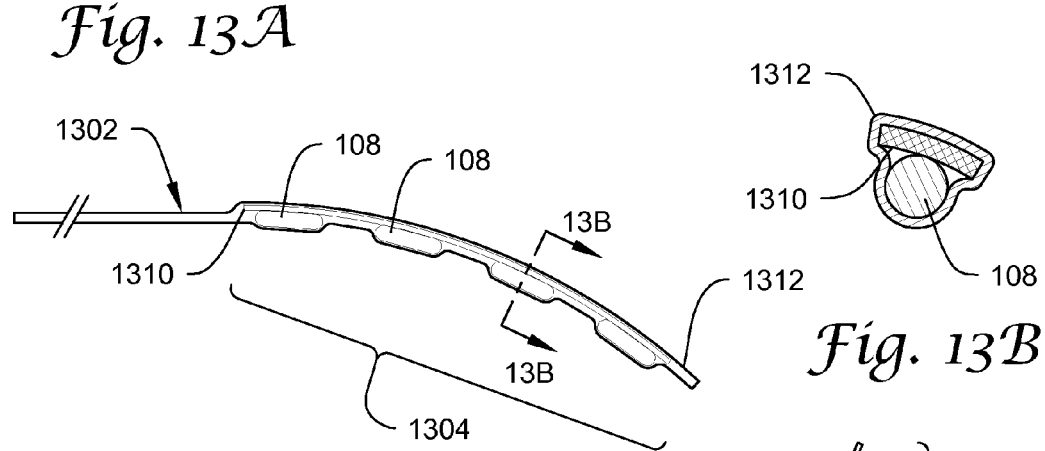
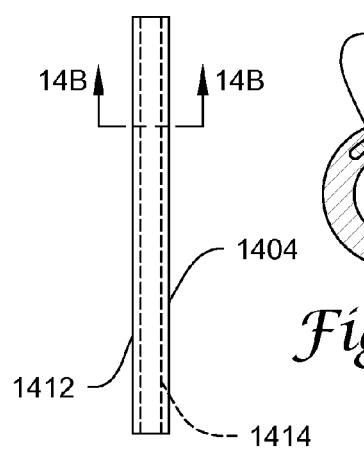
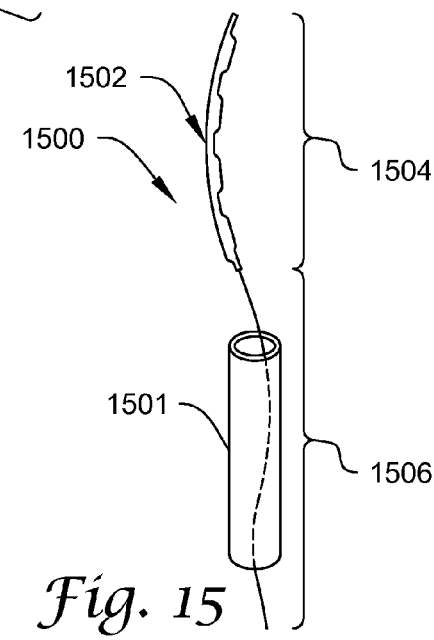

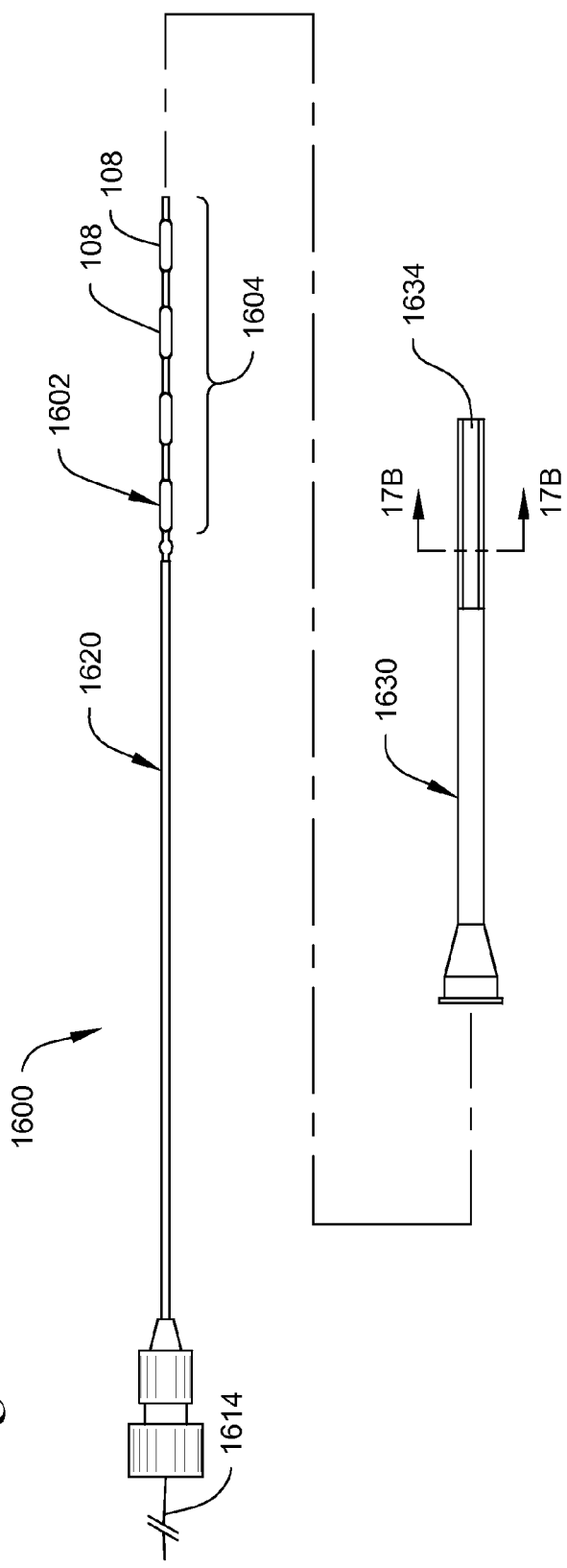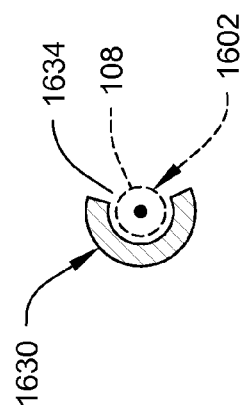
Fig. 17A
Fig. 17B

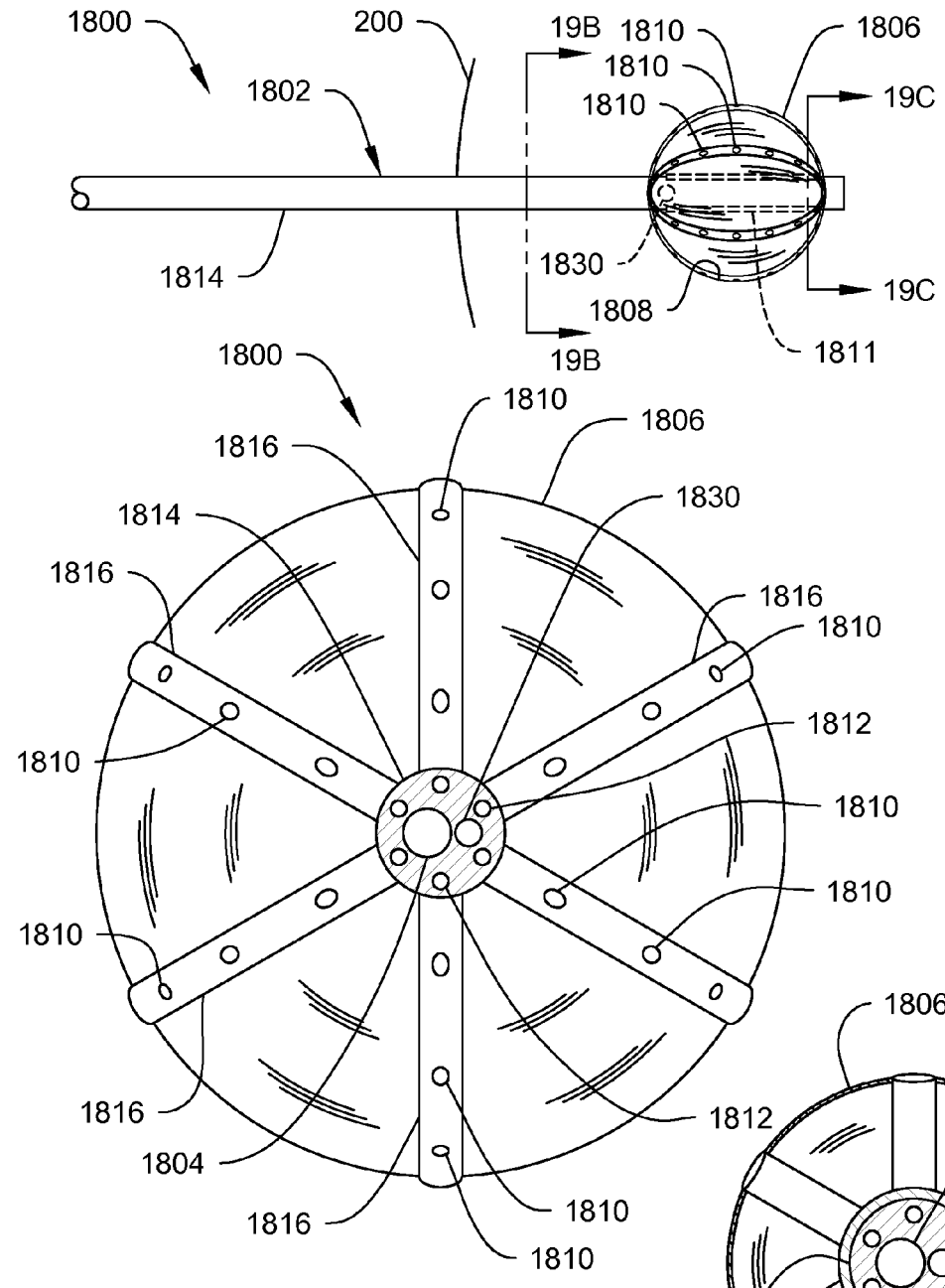
Fig. 19A
Fig. 19B
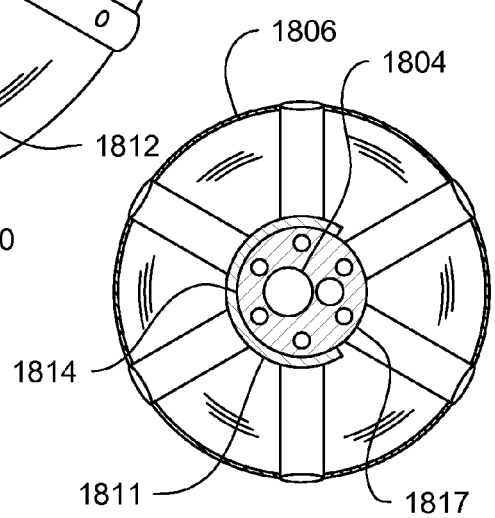
Fig. 19C

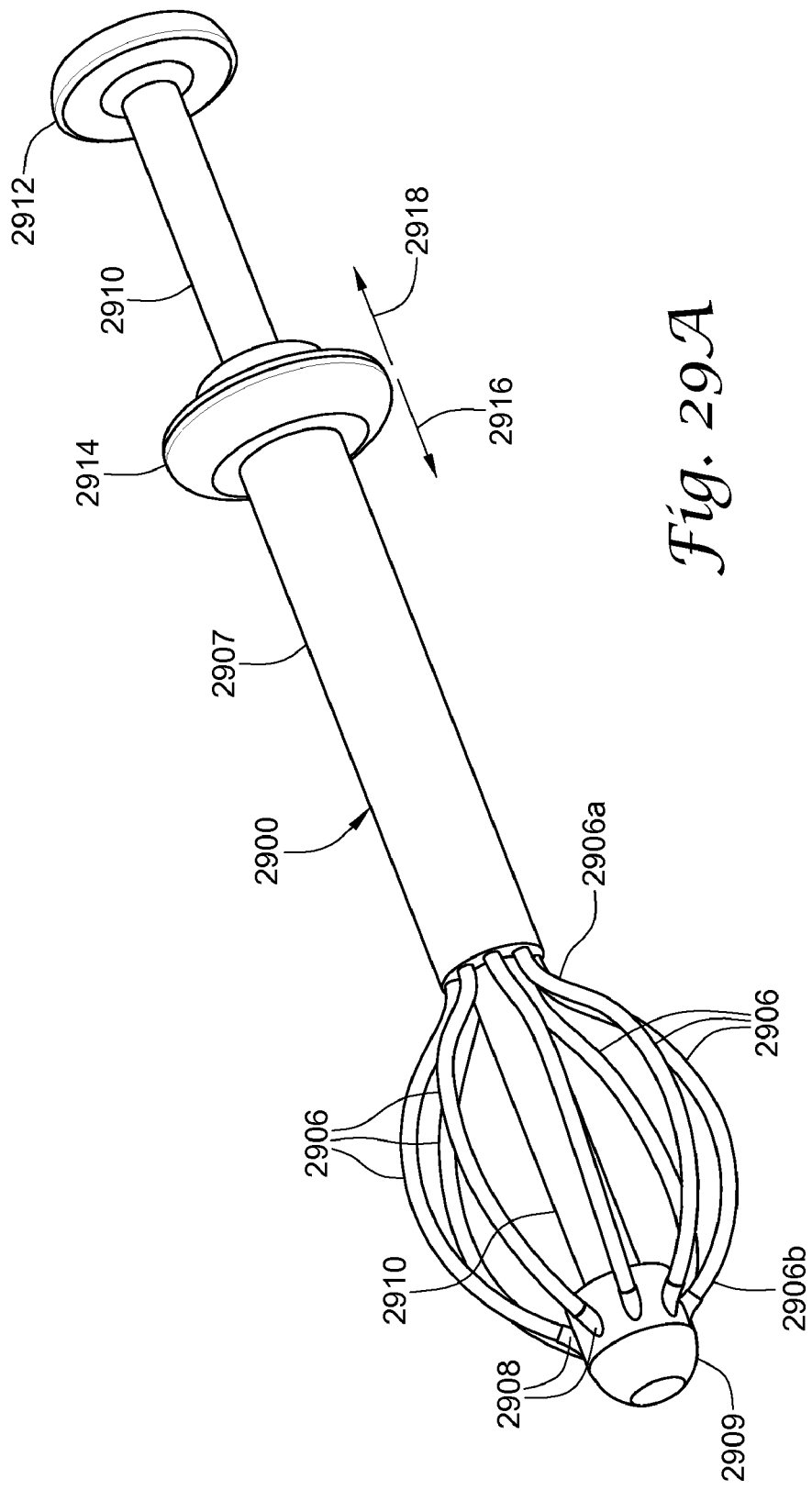

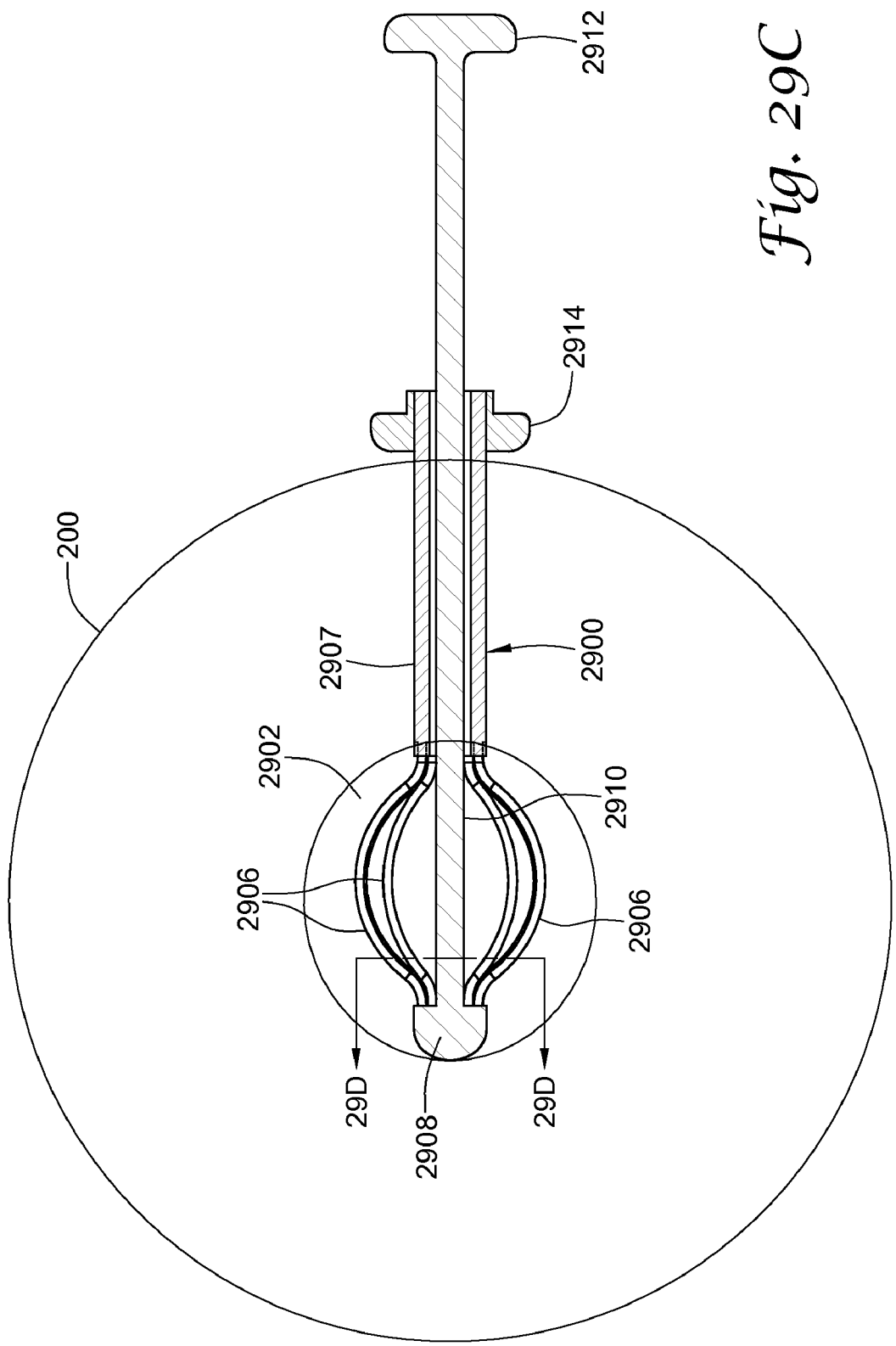

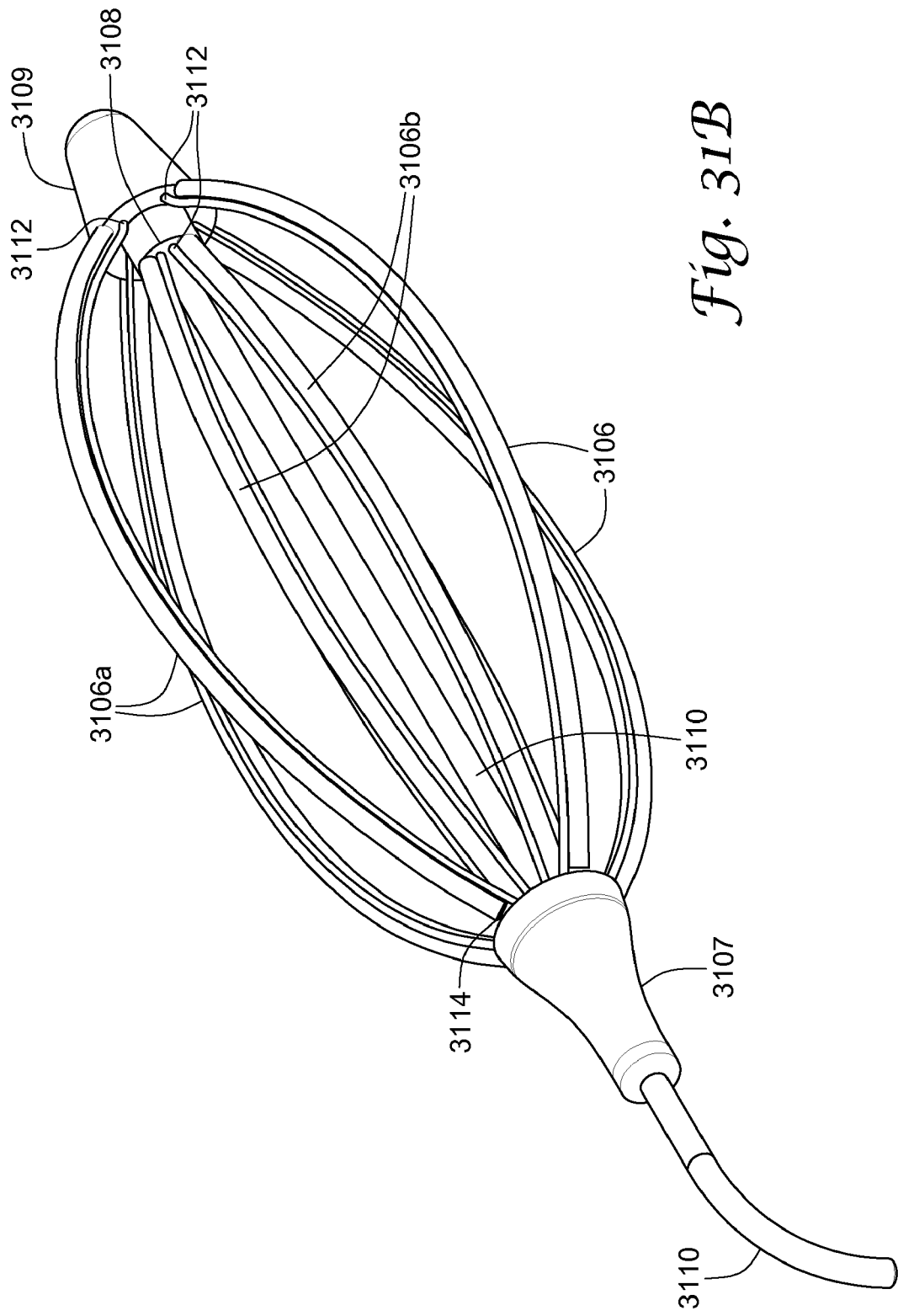

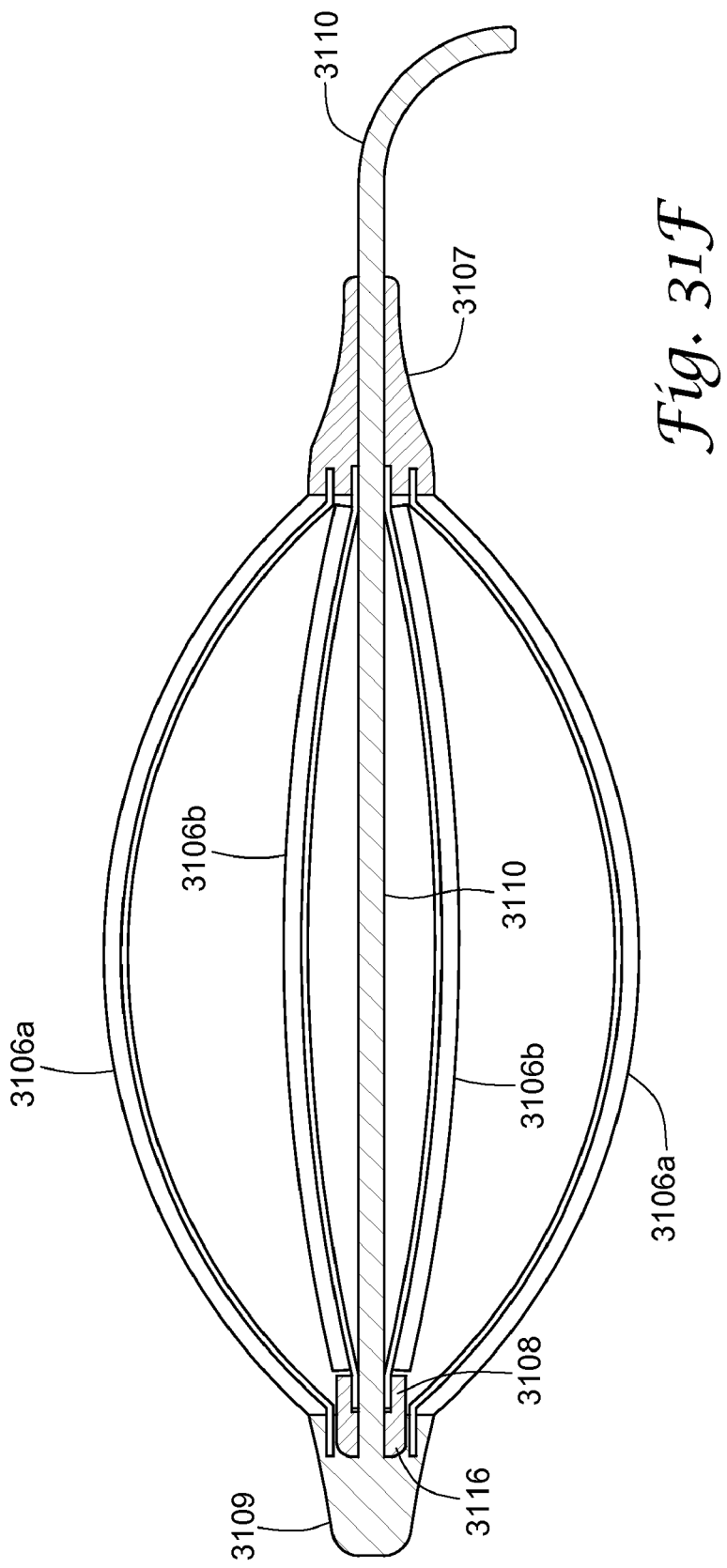

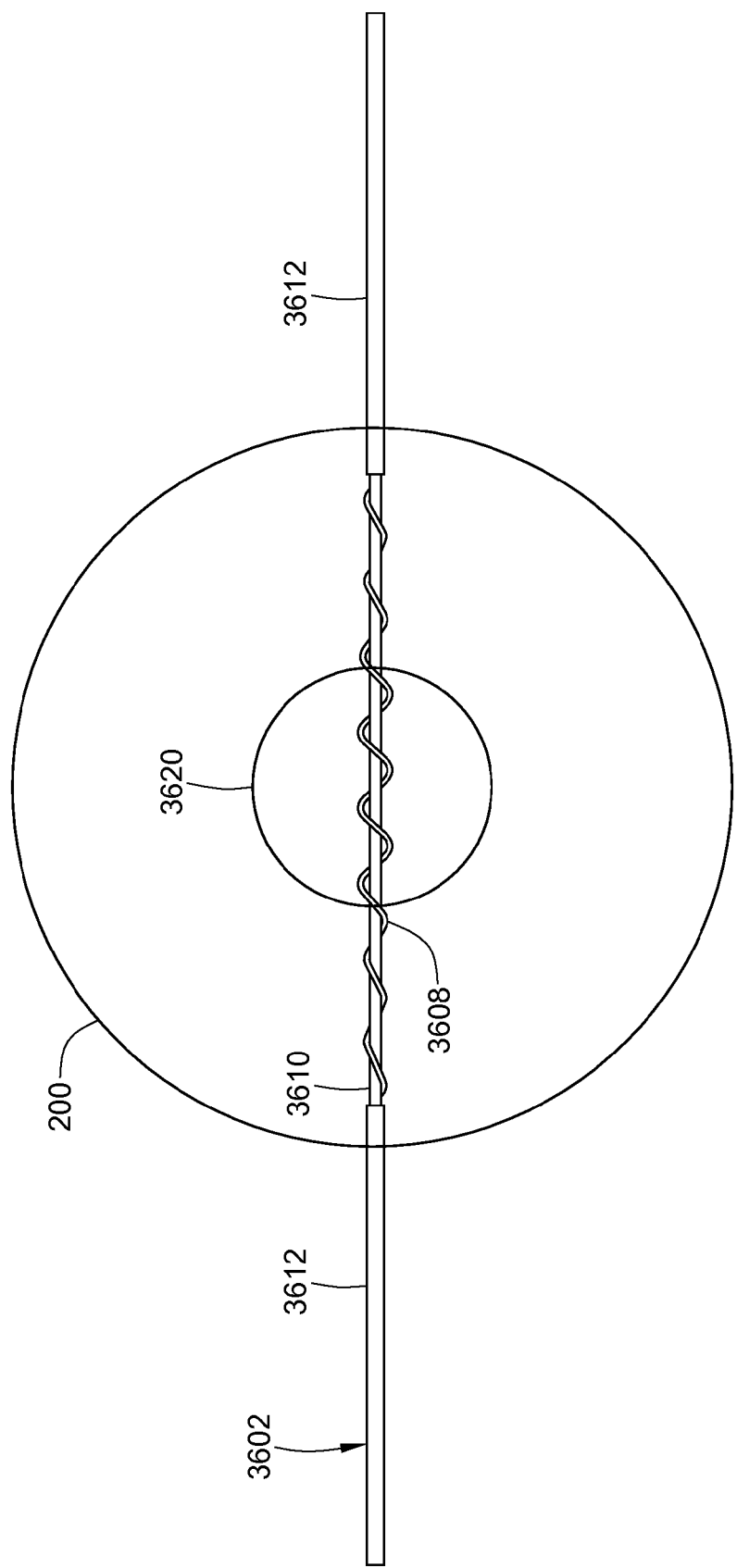

BRACHYTHERAPY APPARATUS AND METHODS FOR USING THEM

This application claims benefit of U.S. Provisional Application Ser. No. 60/735,649, filed Nov. 10, 2005, the entire disclosure of which is expressly incorporated by reference herein.

FIELD OF THE INVENTION

The present invention relates generally to apparatus, methods, and systems for providing brachytherapy to a human or other mammalian body, and more particularly to expandable apparatus for performing brachytherapy treatment within tissue, e.g., within breast tissue and/or within a body cavity, and to methods for performing brachytherapy using such apparatus.

BACKGROUND

Brachytherapy is a type of radiation therapy used to treat malignant tumors, such as cancer of the breast or prostate. In general, brachytherapy involves positioning a radiation source directly into target tissue, which may include a tumor and/or tissue surrounding a cavity or void, which may contain potentially cancerous cells (such as a cavity or void created by removing a tumor).

Brachytherapy is often divided into two categories: high dose rate (HDR) and low dose rate (LDR) brachytherapy. In HDR brachytherapy, a high activity radiation source is placed into target tissue, often via a previously implanted catheter, for a short period of time, e.g., lasting from several seconds to a few minutes. In contrast, LDR brachytherapy places a low activity radiation source into the target tissue for a longer, sometimes indefinite, period of time.

Both forms of brachytherapy have advantages. For instance, HDR brachytherapy provides higher radiation levels delivered over a shorter dose delivery period. LDR brachytherapy, on the other hand, utilizes lower activity radiation sources. The energy field of the LDR radiation source results in a measured and localized dose of radiation delivered to target tissue, e.g., a tumor, gland, or other tissue surrounding a cavity or void. However, the energy field thereafter decays to avoid excessive exposure of nearby healthy tissue.

Due in part to the lower activity of LDR radiation sources, LDR brachytherapy may provide various advantages. For example, for healthcare workers, exposure precautions for LDR brachytherapy may be less stringent than those for HDR brachytherapy. Also there are radiobiological advantages of LDR brachytherapy over HDR brachytherapy (e.g. the dose rate effect), which can lead to better sparing of normal tissue during treatment. Moreover, for patients, the relatively longer implantation period associated with LDR brachytherapy may result in fewer visits to a healthcare facility over the course of radiation treatment, as compared to HDR brachytherapy where patients must return to the healthcare facility for each fraction of radiation delivered, which, for breast brachytherapy, may typically include eight to ten (8-10) fractions.

Common radiation sources used in LDR brachytherapy include radioactive isotopes such as Palladium (Pd)-103, Iodine (I)-125, Gold (Au)-198, and Iridium (Ir)-192. While the size and shape of the isotopes may vary, they are provided, in common applications (e.g., prostate brachytherapy), in a standardized size of cylindrically shaped capsules that are approximately the size of a grain of rice, e.g., about 0.8 millimeter in diameter and about 4.5 millimeters in length, and are often referred to as "seeds."

LDR seeds are often delivered through needles using a guide template. The guide template may include a matrix of holes that guide the longitudinal advancement of the needles to ensure their proper position relative to the target tissue. Once the needles are properly located in the target tissue, the seeds may be deposited along the longitudinal axis of each needle, after which the needles may be withdrawn.

While effective, current brachytherapy implementations have potential drawbacks. For example, the LDR seeds are typically left indwelling and free floating within the target tissue and are, therefore, susceptible to migration. Moreover, once implanted, LDR seeds are generally not considered removable or repositionable. LDR brachytherapy may also require careful dose distribution calculations and seed mapping before, and often during, seed implantation. Such calculation and mapping may allow effective radiation delivery to the target tissue volume, while minimizing radiation to surrounding healthy tissue (e.g., the urethra and rectum, for example, in prostate brachytherapy). Yet, while such dose calculation and seed mapping techniques are effective, problems may exist, such as potentially significant variability in accuracy of seed placement among different clinicians.

Yet another issue with conventional LDR brachytherapy techniques is that many of these techniques often require the radioactive seeds to be manipulated individually at the time of implantation, an often time-consuming process. Moreover, conventional LDR delivery needles are generally limited to delivering the seeds linearly (along a relatively straight line). Thus, to achieve a desired therapy profile, numerous implants (e.g., including about 50-100 seeds, as are common with prostate brachytherapy) are often required, in conjunction with potentially complex dose distribution and mapping techniques and equipment.

SUMMARY

The present invention is generally directed to apparatus and methods for delivering brachytherapy to a localized target tissue region. While the invention is useful in treating most any area of the body, it offers particular advantages in the treatment of breast tissue, e.g., breast tumors or lumpectomy cavities. For example, the invention may be used to place and remove a localized radiation source for both neoadjuvant and post-excisional treatment.

Exemplary embodiments of the invention are directed to brachytherapy devices and apparatus. Such devices and apparatus are capable of delivering brachytherapy treatment to a target region (e.g., breast tissue region). Other embodiments are directed to delivering brachytherapy devices to the target region. Systems and methods for delivering brachytherapy to the target region are also provided.

In accordance with one embodiment, a brachytherapy treatment apparatus is provided that includes an elongate body including a proximal end and a distal end sized for introduction into a tract through tissue. A plurality of elongate members may be provided on the distal end including pathways for receiving a source of radiation therealong, the elongate members being movable from a collapsed configuration for introduction through a tissue tract to a target location, and an expanded configuration. A source of radiation may be introduceable along the pathways for delivering radiation to the target location.

In accordance with another embodiment, a method is provided for brachytherapy treatment of tissue within a body that includes creating a tract through tissue to a target location comprising a cavity, and advancing an elongate body carrying a plurality of elongate members through the tract into the target location with the elongate members in a collapsed configuration. The elongate members may be directed to an expanded configuration at the target location to position the elongate members away from a central axis such that tissue in the target region (e.g., surrounding the cavity) extends between at least a portion of adjacent elongate members, and radiation may be delivered to the target location to treat tissue at the target location.

The above summary is not intended to describe each embodiment or every implementation of the present invention. Rather, a more complete understanding of the invention will become apparent and appreciated by reference to the following detailed description and claims in view of the accompanying drawing.

BRIEF DESCRIPTION OF THE DRAWINGS

The present invention will be further described with reference to the drawing, wherein:

FIGS. 3A-3B are enlarged partial views of a brachytherapy device in accordance with yet another embodiment;

FIGS. 4A-4B are enlarged partial views of a brachytherapy device in accordance with still another embodiment;

FIGS. 5A-5B are enlarged partial views of a brachytherapy device in accordance with yet another embodiment;

FIG. 5C is a view of the brachytherapy device of FIGS. 5A-5B illustrating an exemplary removal method;

FIG. 6 is an exploded view of a brachytherapy apparatus or kit in accordance with yet another embodiment;

FIG. 7 illustrates the brachytherapy apparatus of FIG. 6 as it may be partially assembled;

FIGS. 8A-8E are diagrammatic illustrations of a method of using the brachytherapy apparatus of FIGS. 6 and 7;

FIGS. 9A-9B are enlarged partial views of a brachytherapy device in accordance with another embodiment;

FIGS. 10A-10B are enlarged partial views of a brachytherapy device in accordance with yet another embodiment;

FIGS. 11A-11B are enlarged partial views of a brachytherapy device in accordance with still another embodiment;

FIGS. 12A-12B are enlarged partial views of a brachytherapy device in accordance with still another embodiment;

FIGS. 13A-13B are enlarged partial views of a brachytherapy device in accordance with yet another embodiment;

FIGS. 14A-14B are enlarged partial views of a brachytherapy device in accordance with still another embodiment;

FIG. 15 is a diagrammatic view of a brachytherapy apparatus in accordance with another embodiment;

FIGS. 16A-16G are diagrammatic illustrations of non-linear brachytherapy apparatus and methods in accordance with various embodiments, wherein: FIGS. 16A-16E illustrate a dual, off-axis catheter assembly; and FIGS. 16F-16G illustrate a spiral-shaped catheter;

FIGS. 17A-17B illustrate a brachytherapy apparatus in accordance with yet another embodiment;

FIGS. 19A-19C are diagrammatic views of a balloon catheter assembly, e.g., HDR catheter, in accordance with one embodiment;

FIGS. 28A-28D illustrate an intracavitary brachytherapy treatment apparatus, wherein: FIG. 28A illustrates the apparatus in a collapsed, e.g., linear, configuration; FIGS. 28B and 28C illustrate the apparatus in partially expanded or deployed configurations; and FIG. 28D illustrates the apparatus in a fully deployed configuration;

FIGS. 29A-29F illustrate an intracavitary brachytherapy treatment apparatus, wherein: FIG. 29A is a perspective view of the apparatus in an expanded or deployed, e.g., curvilinear, configuration; FIG. 29B is a section view of the apparatus in a collapsed, e.g., straight, configuration and positioned within a lumpectomy cavity; FIG. 29C is a section view of the apparatus in the partially deployed configuration within the cavity; FIG. 29D is a cross-section taken along lines 29D-29D of FIG. 29C; FIG. 29E illustrates an alternative partial cross-section of a portion of the apparatus of FIG. 29D; and FIG. 29F illustrates a perspective view of a portion of the apparatus;

FIGS. 30A-30C illustrate an intracavitary brachytherapy treatment apparatus in accordance with yet another embodiment, wherein: FIG. 30A is a side elevation view in an expanded or deployed, e.g., curvilinear, configuration; FIG. 30B is a section view of the apparatus in a collapsed, e.g., straight configuration; and FIG. 30C is a section view of the apparatus in the expanded or deployed configuration;

FIGS. 31A-31F illustrate an intracavitary or curvilinear brachytherapy treatment apparatus in accordance with still another embodiment, wherein: FIG. 31A is a perspective view of the apparatus in a collapsed, e.g., straight, configuration; FIG. 31B is a perspective view of the apparatus in an expanded or deployed, e.g., curvilinear, configuration; FIG. 31C is a side elevation view of the apparatus in the collapsed configuration; FIG. 31D is an end elevation view of the apparatus in the collapsed configuration; FIG. 31E is a section view of the apparatus in the collapsed configuration; and FIG. 31F is a section view of the apparatus in the deployed configuration;

FIGS. 32A-32G illustrate an exemplary method of using the apparatus of FIGS. 31A-31F to delivery brachytherapy to a cavity within a body, e.g., a lumpectomy cavity of a breast, wherein: FIG. 32A is a perspective view of the apparatus collapsed and implanted; FIGS. 32B and 32C are front and side elevation views of the implanted and collapsed apparatus, respectively; FIG. 32D is a perspective cross section of the breast with the apparatus in the deployed configuration; FIG. 32E is a section view of the breast with the apparatus in the deployed configuration; FIG. 32F is a diagrammatic view of the apparatus deployed within the cavity; and FIG. 32G is a diagrammatic section view illustrating exemplary radiation coverage provided by the apparatus;

FIGS. 33A-33G illustrate an intracavitary brachytherapy treatment apparatus in accordance with yet another embodiment; wherein: FIG. 33A is a side elevation view of the apparatus in a collapsed configuration; FIG. 33B is a perspective view of the apparatus in a deployed configuration; FIG. 33C is a side elevation view of the apparatus in the deployed configuration; FIG. 33D is a cross section taken along line 22D-22D of FIG. 33C; FIG. 33E is another section view of the apparatus; FIG. 33F illustrates the apparatus implanted and partially deployed within a target tissue region; and FIG. 33G illustrates the apparatus fully deployed within the target tissue region.

DETAILED DESCRIPTION OF EXEMPLARY EMBODIMENTS

Figure 1:
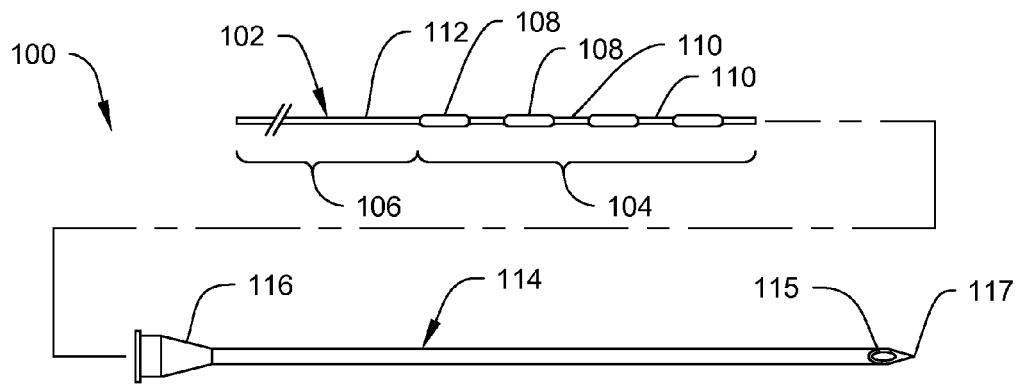
FIG. 1 illustrates an exemplary brachytherapy apparatus or kit in accordance with one embodiment.

In the following detailed description of exemplary embodiments, reference is made to the accompanying drawings, which form a part hereof, and in which are shown by way of illustration specific embodiments in which the invention may be practiced. It is to be understood that other embodiments may be utilized and structural changes may be made without departing from the scope of the present invention.

Generally speaking, the present invention is directed to brachytherapy apparatus and methods. For example, in one embodiment, a system is provided for delivering one or more therapeutic elements (e.g., radiation sources) relative to a target tissue region. Once delivered, the radiation sources may be either immediately withdrawn (e.g., in HDR applications), or left in place, e.g., implanted, for a defined period (e.g., in LDR applications). In either instance, the radiation sources may deliver therapy to the target tissue region in accordance with a predefined therapy profile.

In some embodiments, LDR radiation sources may be implanted and secured to the body or target tissue in such a way as to prevent or substantially limit movement of the sources relative to the target tissue. Unlike conventional LDR brachytherapy, the apparatus and methods described herein may facilitate indwelling therapy using pre-arranged packages of radioactive sources, e.g., seeds, but also allow easy removal of the radiation sources at the completion of brachytherapy.

As used herein, "radiation source" and "radioactive source" may include most any therapeutic element operable to deliver a dose of radiation. For example, the radiation source may be one or more radioactive seeds or, alternatively, one or more LDR or HDR wire elements (e.g., Iridium wire).

The term "implantable," as used herein, indicates the capability of a device to be inserted into the body and then maintained in a relatively fixed or static position within the surrounding tissue, for an extended period of time, e.g., an hour or more and, more preferably, several hours or more, including several days or more.

Furthermore, "target tissue," "target tissue region," "target region," and "target tissue volume," as used herein, may include most any portion of a human (or other mammalian) body that has been identified to benefit from radiation therapy. For example, the target tissue region may be a tumor or lesion itself, tissue proximate or surrounding the tumor, or a cavity region created by tumor excision (such as the surrounding tissue or cavity associated with a lumpectomy cavity of the breast).

It should be noted that, while described herein primarily with respect to LDR brachytherapy, the apparatus and methods described herein may also be used for HDR brachytherapy (e.g., HDR catheters), as described further below. Moreover, while described herein with respect to brachytherapy, the apparatus and methods may apply to other therapy regimens that benefit from the removable implantation of therapy-delivering elements.

For the sake of brevity, the apparatus and methods are described herein for treating breast cancer. However, this particular application is not limiting. That is, those of skill in the art will readily appreciate that the systems, apparatus, and methods described herein may apply to most any cancer that may receive benefit from brachytherapy.

With this introduction, turning to the drawings, FIG. 1 illustrates an exemplary kit or apparatus 100 for providing brachytherapy to a target tissue region of a body. The apparatus 100 may include an elongate and flexible, removably implantable brachytherapy treatment device 102 (also referred to hereinafter as "brachytherapy device 102") having a therapy delivery portion 104, and an elongate and flexible tail portion 106. The tail portion 106 may, as further described below, provide the ability to remove the device 102 at therapy completion. Other components described below, e.g. locking members, may also be included with the apparatus 100.

The term "flexible" is used herein to describe a component that is highly pliant, e.g., a component that may be substantially and easily bent, flexed, and/or twisted without experiencing breakage or permanent deformation.

The therapy delivery portion 104 may form a carrier pod of therapeutic elements, e.g., radiation sources such as radioactive seeds 108, secured relative to one another and to the therapy delivery portion 104. One or more spacers 110 may optionally be located between each seed 108 to obtain the desired seed separation.

The seeds 108 may be produced from most any acceptable radioactive source now known (e.g., radioactive Palladium, Iodine, Cesium, or Iridium) or later developed. Typically, numerous seeds 108 are provided and precisely placed along the length of the therapy delivery portion 104 in order to correspond to the desired therapy delivery regimen. The seeds 108 may have the same radiation intensity or one or more seeds 108 in a pod may have different radiation intensities from one another. In some applications, one or more of the seeds 108 may be separated by spacers of varying length to achieve the desired dose effect. While the radioactive sources are described herein as seeds 108, they may take other forms such as a continuous filament (or numerous discontinuous segments) of radioactive wire (e.g., Iridium wire).

In some embodiments, the brachytherapy device 102 may include a flexible casing or casing member, illustrated in the figures as tube or tube member 112, in which the seeds 108 and optional spacers 110 are securely retained. In some embodiments, the casing is made from a non-dissolving and flexible, heat-shrinkable tubing material. "Heat-shrinkable tubing," as used herein, refers to tubing, such as various plastic tubing, in which subsequent thermal exposure causes the tubing to shrink, thereby allowing it to securely retain the seeds 108 in place. Exemplary heat-shrinkable materials include polyester, fluorinated polymers, and polyolefins.

While most any number of tubing sizes is contemplated, in one embodiment, the tube 112 may have an initial inside diameter of about 1 mm and a wall thickness of about 0.05 mm. Once heated, the tube 112 may shrink (if unconstrained) to an outer diameter ranging from about 0.3 mm to about 0.6 mm.

While the casing is described herein generally as tube-shaped, the casing may, in other embodiments, be most any shape that is capable of effectively securing the individual seeds 108 relative to the casing and to one another.

Once the seeds 108 and optional spacers 110 are located within the tube 112, the tube may be shrunk by exposure to heat, thus contracting the tube 112 around the seeds 108. The tail portion 106 may be formed by an integral portion, e.g., extension, of the casing (tube 112) that extends beyond the seeds 108. To reduce the diameter of the tail portion 106, it may also be thermally treated (shrunk). Other embodiments (described below) may utilize a two-part brachytherapy device, e.g., a separate filament tail portion attached to the therapy delivery portion.

Regardless of the specific configuration, the brachytherapy devices 102 described herein provide not only proper spacing of the seeds 108, but also facilitate subsequent seed identification and removal. Moreover, because the seeds are contained within the pod defined by the therapy delivery portion 104, seeds may not require individual handling, thus simplifying inventory and handling prior to, and at the time of, implantation.

The components of the device 102, including the casing (tube 112) and tail portion 106, are preferably constructed of non-dissolving materials. The term "non-dissolving" is used herein to indicate most any material that does not substantially deteriorate or otherwise break down during the implantation period.

The brachytherapy apparatus 100 may also include a catheter or needle 114. While illustrated as needle 114, any other type of catheter or tubular member, such as the cannulae described further below, may also be used without departing from the scope of the invention. The needle 114 defines a lumen 115 of sufficient size to allow the therapy device 102 to pass therethrough, as indicated in FIG. 1. In some embodiments, the needle 114 may further include a hub 116 at a proximal end, e.g., to assist with manipulation of the needle and/or insertion of the therapy device 102. A distal end of the needle 114 may form a sharpened tip 117 operable to pierce the body, as further described below. The needle 114 may be made from most any suitable biocompatible material. For example, it may be made from metal, e.g., stainless steel, titanium, or nickel titanium alloy. It may also include a removable outer sheath (not shown), e.g., made of plastic, such as a fluorinated polymer.

FIGS. 2A-2E illustrate an exemplary method of using the brachytherapy apparatus 100 of FIG. 1. Once a target tissue region 202 (e.g., a tumor or tumor cavity) within body 200 is accurately located, the needle 114 may be inserted into the body 200, as shown by arrow 203 in FIG. 2A, to a predetermined depth. The relative location(s) of the needle 114 and/or the target tissue region 202 may be determined by most any method, e.g., via ultrasound, CT scan, stereotactic X-ray, and the like. The needle 114 may further be aligned with the use of a needle guiding template, e.g., as described below, or by other techniques.

Figure 2A:
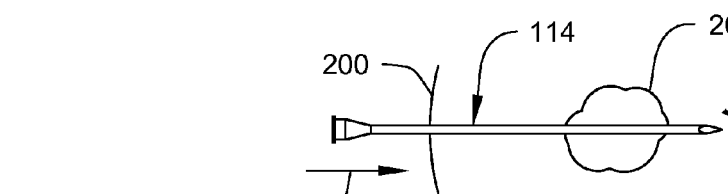
FIGS. 2A-2E are diagrammatic illustrations of a method for using the brachytherapy apparatus of FIG. 1.
Figure 2B:
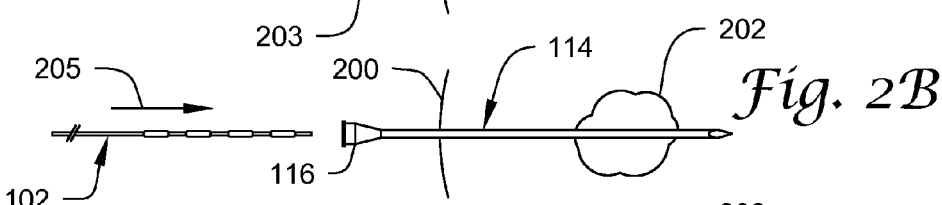
Figure 2C:
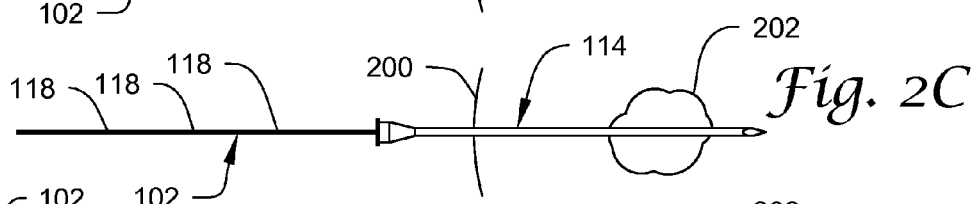

Next, the brachytherapy device 102 may be inserted into the lumen 115 of the needle 114, as shown by arrow 205 in FIG. 2B, until the therapy delivery portion 104 is located at the desired depth relative to the target tissue region 202 as shown in FIG. 2C. To assist in determining the approximate insertion depth of the therapy device 102, the tail portion 106 may include measurement demarcations 118. Other location verification techniques, e.g., X-ray, ultrasound, etc., may also be used. Alternatively, the needle 114 may be inserted with the therapy device 102 at least partially loaded into the lumen 115 of the needle 114.

Figure 2D:
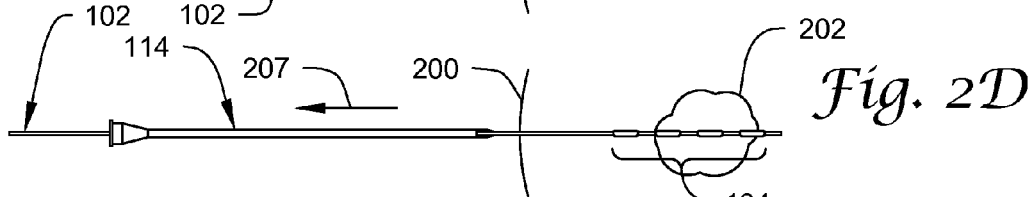
Figure 2E:
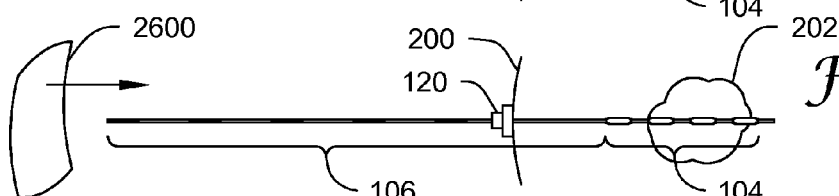

Once the therapy device 102 is located at the desired depth, the needle 114 may be withdrawn from the body in the direction 207 as shown in FIG. 2D, leaving the therapy delivery portion 104 of the device 102 at the desired position within the body 200. The tail portion 106 is preferably of sufficient length such that it extends outside of the body 200, as shown in FIG. 2E. That is, the tail portion 106 may extend externally through a puncture made by the needle 114. In one embodiment, the tail portion 106 may have sufficient column strength such that the tail portion 106 may be held while the needle 114 is withdrawn, thereby maintaining the therapy delivery portion 104 at the desired position.

Figure 27:
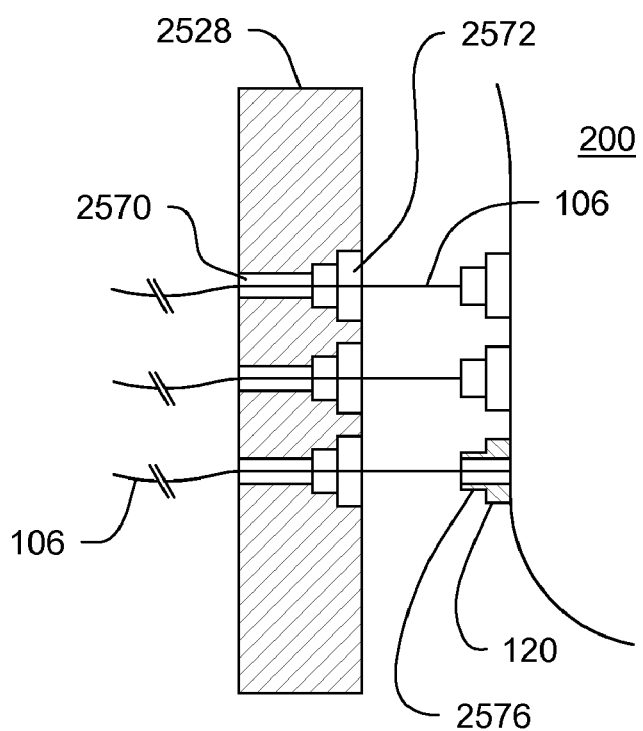
FIG. 27 is a cross-section of a portion of the delivery system of FIGS. 25A-25D.

In order to prevent migration of the therapy delivery portion 104, a locking member 120 may be crimped or otherwise attached to the tail portion 106 of the therapy delivery device 102 immediately adjacent the associated puncture in the body 200. The locking member 120 may assist in maintaining the location of the therapy delivery portion 104 relative to the target tissue region 202. While most any locking member may be used, one embodiment utilizes a malleable, hat- or U-shaped lock that can be easily and securely crimped to the tail portion with, for example, a surgical clip applier or similar tool. An enlarged view of an exemplary locking member 120 is illustrated in FIG. 27.

For illustration purposes, only a single therapy delivery device 102 is shown in FIGS. 2A-2E. However, in practice, multiple devices may be utilized to provide adequate dosage to the target tissue region 202. The actual number of devices 102 may vary depending on various parameters such as lesion size, radiation source activity levels, and proximity to other organs/vulnerable tissue (e.g., skin, chest wall). However, quantities ranging from about five (5) to about twenty five (25) devices are contemplated in an exemplary array of therapy devices 102.

Figure 2F:
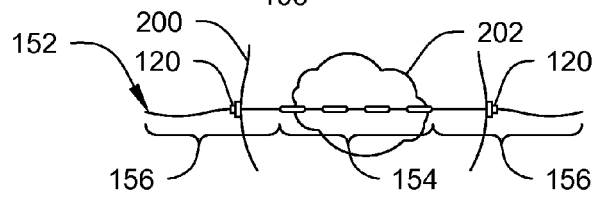
FIG. 2F is a diagrammatic illustration of another brachytherapy apparatus in accordance with another embodiment.

FIG. 2F illustrates a variation of the therapy device 102 of FIGS. 2A-2E that may offer additional benefits, especially to the treatment of breast cancer. In this embodiment, a therapy device 152 similar in most respects to the device 102 is provided. However, the device 152 may include both a first tail portion extending from a first end of a therapy delivery portion 154 and a second tail portion extending from a second end, i.e., it may include a tail portion 156 at each end of the therapy delivery portion 154. During implantation, the needle 114 may pass completely through the body, e.g., breast 200, such that one tail portion 156 extends out the opposite side of the breast 200. In this way, locking members 120 may be secured at two locations relative to the target tissue region 202, thus preventing or substantially limiting movement of the therapy delivery portion 154 relative to the target tissue region 202.

Unlike conventional brachytherapy catheters, which may be two millimeters (2 mm) or more in diameter, the therapy devices 102 may be about one millimeter (1 mm) or less in diameter at the therapy delivery portion 104 and even smaller at the tail portion 106. This construction permits the devices 102 to be relatively small and flexible, and thus less obtrusive to the patient. In fact, the size and flexibility of the tail portions 106 may be similar to that of a conventional suture. As a result, securing the tail portions 106 may be accomplished in any number of ways including, for example, folding the tail portions against the contour of the surrounding body and fixing them such as by tying the ends and/or securing the ends with adhesive, the latter represented by bandage 2600 in FIGS. 2E and 26.

FIG. 3A is an enlarged view of the therapy device 102 of FIG. 1. As clearly illustrated in this view, the therapy device 102 may include the therapy delivery portion 104 and the tail portion 106. As described above, the therapy delivery portion 104 may include one, or preferably more, radioactive seeds 108 separated by spacers 110 and encased within the casing, e.g., heat-shrinkable tube 112. The tail portion 106 may be formed by the portion of the tube 112 that does not surround the seeds 108. In some embodiments, the conformal properties of the tube 112 may be sufficient to ensure proper seed spacing, thus negating the need for spacers 110. FIG. 3B illustrates a section view through a seed 108 and the tube 112 taken along line 3B-3B of FIG. 3A.

FIGS. 4A-4B illustrate a therapy device 402 in accordance with another embodiment. The device 402 is similar in many respects to the device 102 described above. For example, the device 402 may include a therapy delivery portion 404 and a tail portion 406 as illustrated in FIG. 4A. A casing, e.g., heat shrinkable tube 412, may be used to encase the seeds 108 and optional spacers 110 as well as to form the tail portion 406. However, unlike the embodiment of FIGS. 3A-3B, the tube 412 may include a radioabsorptive portion 414, e.g., a substance or liner, positioned along a portion of the circumference of the therapy delivery portion 404 (see FIG. 4B). The radioabsorptive portion 414 may include a radiation attenuating material, which may reduce radiation exposure to tissue blocked by the radioabsorptive portion 414 as opposed to tissue not blocked by the portion 414. While not limited to any particular embodiment, the radioabsorptive portion may be formed by a substance (e.g., Tungsten, Nickel-Titanium alloy, stainless steel) applied to, or impregnated within, a portion of the tube 412. Alternatively, the radioabsorptive portion(s) may be formed by a liner within, or secured to a portion of, the tube 412. FIG. 4B illustrates a section view through a seed 108 and the tube 412 taken along line 4B-4B of FIG. 4A.

The term "radiotransparent" is used herein to indicate only that the identified portion of the apparatus or device is relatively more transparent to radiation than the portion identified as "radioabsorptive."

FIGS. 5A-5B illustrate a therapy device 502 in accordance with yet another embodiment. The device 502 is similar in many respects to the device 102 described above. For example, the device 502 may include a therapy delivery portion 504 and a tail portion 506 as shown in FIG. 5A. A casing, e.g., heat shrinkable tube 512, may be used to encase the seeds 108 and optional spacers 110 as well as to form the tail portion 506. However, unlike the previous embodiments, the therapy device 502 may incorporate an anchor member, e.g., a flat or round cross-section anchor wire 514, which extends along at least a part of the therapy delivery portion 504. The anchor wire 514 protrudes from one or both ends of the therapy delivery portion and may be bent or otherwise formed to provide one or more hooks, barbs, or other anchors 516.

When the therapy delivery portion 504 exits the needle 114 (see FIG. 1) during implantation, the anchors 516 may extend and engage surrounding tissue, thereby assisting in preventing proximal migration of the therapy device 502. While only a single anchor is shown at each end of the therapy delivery portion 504, other embodiments may include multiple anchors at one or both ends to further resist movement, e.g., rotating or twisting, distal migration, and the like. FIG. 5B illustrates a section view through a seed 108 and the tube 512 taken along line 5B-5B of FIG. 5A.

After the desired dose of radiation has been delivered, the therapy device 102 (or any of the other therapy devices described herein, e.g., devices 402 or 502), may be removed in any number of ways. For example, the device 102 may be removed by first removing any dressing (e.g., bandage 2600 of FIG. 2E) and locking member(s) 120, and then simply applying a pulling force to one of the tail portions 106 that extends outside of the body 200. Alternatively, the devices 102 may be removed prior to or during excisional surgery of the tumor 202 via known methods, e.g., via methods similar to excision utilizing localization wires.

Where the therapy device 102 includes internal retaining elements, e.g., anchors 516 of device 502 (FIG. 5A), a removal catheter 550 as shown in FIG. 5C may be used. The removal catheter 550 is similar in most respects to the delivery cannulae and needles described herein, e.g., needle 114. The catheter 550 may be threaded over the tail portion 106 and advanced until it encompasses the therapy delivery portion 104. For example, the removal catheter 550 may be advanced until its distal end engages the distal retaining element(s), e.g., distal anchor 516 of FIG. 5A. Further advancement of the removal catheter 550 may bend the anchor sufficiently to permit the therapy delivery portion to slide into the removal catheter as shown in the broken line representation of FIG. 5C. The device 502 and the removal catheter 550 may then be withdrawn as a unit from the body.

With any of the methods described herein, the time that the brachytherapy devices remain implanted may vary according to the desired therapy regimen. While not wishing to be bound to any fixed period, implantations from about one hour up to about eight weeks or more are contemplated for therapy. However, for breast brachytherapy, implantation periods ranging from about one day to several weeks, e.g., four to ten days, are more likely. Moreover, because of the construction of the devices, e.g., devices 102, they may be removed over a range of timeframes subsequent to implantation. This is in contrast to the permanent placement typically associated with conventional LDR brachytherapy and the short exposure time associated with conventional HDR brachytherapy. As a result, intermediate activity radiation sources may be utilized with the methods and apparatus described herein, as well as conventional low and, as further described below, high activity sources.

FIG. 6 illustrates a brachytherapy kit or apparatus 600 in accordance with another embodiment. Unlike the apparatus 100 of FIG. 1, the apparatus 600 may include, among other components, at least a removably implantable brachytherapy treatment device (brachytherapy device 602), a pusher or pusher member 620, a catheter, e.g., cannula or cannula member 630, and a sharp obturator 640.

The therapy device 602, once again, may include a therapy delivery portion 604 and a removal or tail portion 606. The therapy delivery portion 604 may include one or more seeds 108 and optional spacers 110. The seeds 108 may be enclosed within a casing, e.g., heat-shrinkable tube or tube member 612, similar in most respects to the tube 112 described above.

The tail portion 606 in this embodiment, however, is formed by an elongate filament or wire, e.g., a non-dissolving surgical suture 614, coupled or otherwise attached to the therapy delivery portion 604. While most any method of attaching the suture 614 to the therapy delivery portion 604 is possible, one embodiment forms a knot 616 in the suture. The knot 616 may be captured when the tube 612 is heat-shrunk to the therapy delivery portion 604. In other embodiments, the suture 614 may be knotted around or otherwise attached directly to the therapy delivery portion 604. Such suture attachment methods are exemplary only, however, as most any other method of attaching the suture 614 to the therapy delivery portion 604 is possible. The suture 614, as with the tail portion 106 described above, may be made from a non-dissolving material, e.g., polypropylene, polyester, polyamide, and the like.

The pusher member 620 may include a lumen through which the therapy device 602 may pass as indicated in FIGS. 6 and 7. The pusher member may include a suture locking device 622, e.g., a luer hub, at a proximal end to assist with loading and securing of the therapy device 602. The locking device 622 may secure the suture 614 relative to the pusher 620, as further described below. While illustrated as a luer hub, the locking device 622 may include most any friction or clamping device known in the art. For example, the locking device may be an O-ring that may be selectively compressed to pinch the suture 614.

The cannula member 630 may also include a lumen through which the pusher member 620 may pass, as indicated in FIG. 6. The cannula member 630 may include a luer hub 632 at its proximal end that is operable to secure the cannula member relative to the either the sharp obturator 640 or the pusher member 620 when either is slid into the lumen of the cannula member, as further described below.

The sharp obturator 640 may include a handle portion with a hub 642 at a proximal end, and a sharp point 644 operable to pierce body tissue at its distal end. The handle portion may permit comfortable manipulation of the obturator 640. The external diameter of the obturator 640 may be sized so that it fits within the lumen of the cannula member 630, as indicated in FIG. 6.

The components of the apparatus 600 may be made from most any suitable biocompatible material. For example, the cannula member 630, the pusher member 620, and the sharp obturator 640 may be made from metal, e.g., stainless steel or Titanium, plastic, or composite materials.

FIG. 7 illustrates the apparatus 600 as it may be assembled before use. The sharp obturator 640 may be placed in the cannula 630 such that the sharp distal end 644 of the obturator protrudes from the distal end of the cannula 630, as illustrated. The therapy device 602, which includes the therapy delivery portion 604 and the suture 614 as described above, may be positioned within the pusher member 620 such that the therapy delivery portion 604 extends from its distal end and the suture 614 extends from the hub 622 at its proximal end. The suture 614 may be pulled from the proximal end of the pusher member 620 until the therapy delivery portion 604 is at or near the distal end of the pusher member 620, as shown. The locking device 622 may then be engaged to hold the suture 614, and thus the therapy delivery portion 604, in place relative to the pusher member 620.

FIGS. 8A-8E illustrate an exemplary method of using the system 600 for delivering brachytherapy to a portion of a body, e.g., breast 200. Once the target tissue region 202, e.g., tumor or tumor cavity, is identified, the combined cannula 630 and sharp obturator 640 (see FIG. 7) may be advanced into the target tissue region 202, as illustrated by arrow 802 in FIG. 8A. When the distal end of the cannula 630 reaches the desired depth, the sharp obturator 640 may be removed (moved in the direction 804) through the proximal end of the cannula, as shown in FIG. 8B, while leaving the cannula 630 in place.

The combined pusher member 620 and therapy device 602 (see FIG. 7) may then be inserted into the proximal end of the cannula 630, in the direction 806, as shown in FIG. 8C. The pusher member 620 and therapy device 602 may be inserted until the therapy portion 604 is at its desired location, e.g., at or near the distal end of the cannula 630. Location of the therapy portion 604 may be assisted by image guidance, e.g., stereotactic X-ray, ultrasound, CT, and the like.

Once the therapy portion 604 is positioned, the cannula 630 may be retracted (moved in the direction 808), exposing the therapy portion 604 to the target tissue region 202, as shown in FIG. 8D. The locking device 622 may then be unlocked such that the pusher member 620 and cannula 630 may be fully withdrawn (moved in the direction 810) from the body 200, as shown in FIG. 8E. The therapy delivery portion 604 remains implanted at the target tissue region 202 while the suture 614 extends outside the body.

These steps may be repeated for placement of each brachytherapy device 602, or multiple devices may be implanted substantially simultaneously as a group, as further described below.

Although not illustrated, a locking member, such as the locking member 120 illustrated in FIGS. 2E and 27, may be used to secure the therapy device 602, e.g., the tail portion(s) 606, at one or both (see FIG. 2F) ends. Alternatively, the therapy device 602 may include securing elements, such as the anchors 516 shown in FIG. 5. Still further, the therapy device 602 may be secured simply by folding and adhering the tail portions 606 to the breast 200 (see FIGS. 2E and 26).

After the desired dose of radiation has been delivered, the therapy delivery device 102 may be removed in any number of ways as already described herein, e.g., using a removal member, such as the tail portion 606, or a removal cannula.

FIG. 9A is an enlarged view of the therapy device 602 of FIGS. 6-7. As clearly illustrated in this view, the therapy device 602 may include the therapy delivery portion 604 and the tail portion 606. The therapy delivery portion 604 may include one, or preferably more, radioactive seeds 108 securely retained within the casing, e.g., heat-shrinkable tube 612. The tail portion 606 may be formed by the suture 614. The knot 616 of the suture 614 may be secured to the therapy delivery portion 604 by the heat shrinkable tube 612. While shown as utilizing spacers 110, they may not be required in some embodiments, e.g., the conformal properties of the casing, e.g., tube 612, may be sufficient to ensure proper seed 108 spacing and containment. FIG. 9B illustrates a section view of the seed 108 and tube 612 taken along line 9B-9B of FIG. 9A.

FIGS. 10A-10B illustrate a therapy device 1002 in accordance with another embodiment. The device 1002 is similar in many respects to the device 602 described above. For example, the device 1002 may include a therapy delivery portion 1004 and a tail portion 1006. A casing, e.g., heat shrinkable tube 1012, may be used to encase the seeds 108 and optional spacers 110. Like the device 602, the tail portion 1006 may be formed by a suture 614 having a knot 616 that may be heat shrinkable to the therapy delivery portion 1004. However, unlike the device 602 of FIGS. 9A-9B, the tube 1012 may include a radioabsorptive portion 1014 positioned along a part of the circumference of at least the therapy delivery portion 1004 (see FIG. 10B). The radioabsorptive portion 1014, which may be formed integrally or separately with the tube 1012, may limit radiation exposure to tissue blocked by the radioabsorptive portion. FIG. 10B illustrates a section view of the seed 108 and tube 1012 taken along line 10B-10B of FIG. 10A.

FIGS. 11A-11B illustrate a therapy device 1102 in accordance with yet another embodiment. The device 1102 is similar in many respects to the device 602 described above. For example, the device 1102 may include a therapy delivery portion 1104 and a tail portion 1106. A casing, e.g., heat shrinkable tube 1112, may be used to encase and constrain the seeds 108 and optional spacers 110. Like the embodiment illustrated in FIGS. 5A and 5B, the therapy device 1102 may incorporate an anchor member, e.g., anchor wire 1114, which extends along at least a part of the therapy delivery portion 1104 and protrudes from one or both ends. The anchor wire 1114 may be bent at one or both ends to form anchor 1116. When the therapy delivery portion 1104 exits the cannula 630 (see FIG. 8D), the anchor 1116 may extend and capture surrounding tissue, thereby assisting in preventing migration of the therapy device 1102. FIG. 11B illustrates a section view of the seed 108 and tube 1112 taken along line 11B-11B of FIG. 11A.

It is to be understood that any of the various components of the invention described herein may be used interchangeably with any of the described methods and systems. For example, any one of the devices 102, 152, 402, 502, 602, 1002, and 1102 could be used with the methods described in FIGS. 2A-2E, 2F, and 8A-8E without departing from the scope of the invention.

The embodiments described above utilize a therapy delivery portion (e.g., portion 104 of FIG. 1 or portion 604 of FIG. 6) formed primarily by the shrink fit tube (e.g., tube 612 of FIG. 9A) and seeds 108. However, other embodiments of the therapy delivery portion may include an additional support member. The support member may be any material that lends support to the therapy delivery portion, e.g., a strip of material such as stainless steel or superelastic nickel titanium alloy. In addition, to partially support the seeds 108, the material of the support member may divide the therapy delivery portion into a radiotransparent portion and a radioabsorptive portion. That is, it may partially surround at least a portion of the seeds 108 to provide some degree of attenuation or shielding of radiation to surrounding tissue. As a result, tissue on a side of the support member opposite the seeds 108 may receive a lower dose of radiation than tissue on the seed side. The support member may be enclosed within the casing, e.g., heat-shrinkable tube 112 or 612.

For example, FIGS. 12A and 12B illustrate a therapy device 1202 having a tail portion 1206 and a therapy delivery portion 1204 with a plurality of seeds 108 and a straight support member 1210 (see FIG. 12A). The support member 1210 may have a curved, e.g., arc-shaped, cross-section (see FIG. 12B). Alternatively, a relatively flat cross-section (not shown) may be provided. Other embodiments may utilize most any other cross-sectional shape, e.g., v-shaped. The support member 1210 may also have a variety of leading edge shapes including the shovel-tip shape illustrated in FIG. 12A. At least a portion of the support member 1210 may be encased within a casing, e.g., heat shrinkable tube 1212, as already described above.

While the support member 1210 of FIG. 12A is generally straight, other support members may be provided that are curved, e.g., have some degree of curvature. For example, FIG. 13A illustrates a therapy device 1302 having a therapy delivery portion 1304 with a curved support member 1310 that imparts an arc-shaped or otherwise curved-shape to the delivery portion 1304. The support member 1310 may be formed to have curvature in its relaxed state or may simply be sufficiently flexible to permit curved implantation. As with the support member 1210 of FIGS. 12A-12B, the support member 1310 may have most any cross-sectional shape, e.g., a flat shape, curved shape (as shown in FIG. 13B), v-shape, and the like. At least a portion of the support member 1310 may be encased within a casing, e.g., heat shrinkable tube 1312, similar to the casings already described above. FIG. 13B illustrates a section view taken along line 13B-13B of FIG. 13A.

While not illustrated herein, optionally, the support members may include one or more slots, e.g., along a centerline, so that seeds may be placed at least partially within the slot. As a result, a therapy delivery portion that offers more rigidity than the unsupported therapy delivery portions described herein may be obtained while ensuring tissue on both sides of the support member receives radiation treatment.

FIGS. 14A-14B illustrate another exemplary embodiment of a therapy delivery portion 1404. In this embodiment, the therapy delivery portion includes a catheter or casing, e.g., tube 1412, having one or more lumens. A first or main lumen 1408 may receive the seeds (not shown), while a second lumen 1414 may contain an attenuating or shielding element 1416 extending over a longitudinal length of the tube 1412. As a result, the tube 1412 may have a radiotransparent portion (that portion not blocked by the element 1416), and a radioabsorptive portion (that portion shielded by the element 1416). In one embodiment, the tube 1412 can be made by co-extruding plastic (e.g., fluoropolymer) with an attenuating material such as strands of fine metallic wire (e.g., stainless steel, gold). In another embodiment, the attenuating material may be a coextrusion of polymer loaded with an attenuating material such as Tungsten powder. The tube 1412 may or may not be heat-shrinkable. For versatility, the shielding element 1416 may be straight or preformed in a curve. FIG. 14B illustrates a section view taken along line 14B-14B of FIG. 14A.

FIG. 15 is a partial view of an exemplary brachytherapy apparatus 1500 having a therapy device 1502 and catheter, e.g., cannula 1501, wherein the device 1502 includes a curved therapy delivery portion 1504, and a tail portion 1506. Other components of the system, e.g., pusher member and sharp obturator, are not illustrated in this view merely for clarity. The curved therapy delivery portion 1504 may be formed by a curved support member, such as support member 13100 of FIG. 13A. The cannula 1501 preferably has a lumen diameter sufficiently large to accommodate the curved therapy delivery portion 1504 when the latter is constrained in a straightened configuration for delivery. Alternatively, the cannula 1501 may be sized to receive the therapy delivery portion 1504 in its curved configuration. In still yet other embodiments, the therapy delivery portion 1504 may be generally straight but flexible and the cannula 1501 used to deliver the therapy delivery portion may be curved.

Figure 16A:
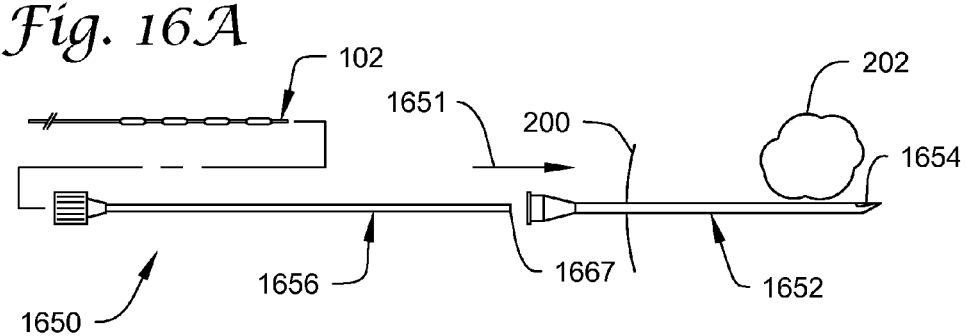
Figure 16B:
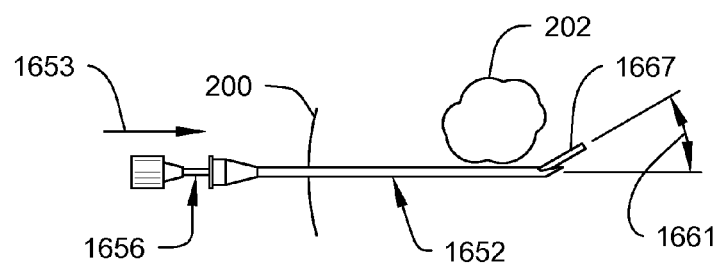

Non-linear (e.g., curved) catheters may also be used for delivering and/or placing the brachytherapy devices described herein to regions and positions inaccessible to straight catheters. For example, FIGS. 16A-16E illustrate an exemplary apparatus 1650 and method operable to implant a brachytherapy device, e.g., device 102 of FIG. 1, along a non-linear axis. FIG. 16A illustrates the apparatus 1650 including a first catheter member, e.g., needle 1652, a second catheter member, e.g., flexible catheter 1656, and a brachytherapy device 102. The needle 1652 includes an off-axis opening 1654 at or near a distal end of the needle. The needle 1652 may be inserted into the body 200, in the direction 1651, until the distal end is positioned past the target tissue region 202 as shown in FIG. 16A. The flexible catheter 1656 may then be inserted through the needle 1652 (in the direction 1653) until a distal end 1667 of the catheter 1656 protrudes from the opening 1654 of the needle 1652 at an angle 1661 as shown in FIG. 16B. That is, an axis of the catheter 1656 may intersect, or be otherwise nonparallel to, an axis of the needle 1652.

The angle 1661 between the axes may vary, but angles ranging from greater than about zero degrees to about ninety degrees (0-90°), and more preferably about five degrees to about thirty five degrees (5-35°), are contemplated.

Figure 16C:
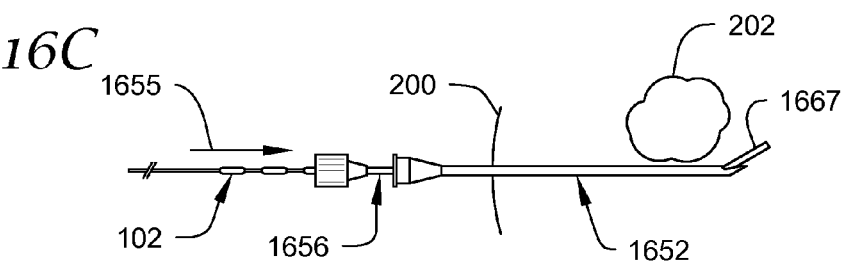

The device 102 may then be threaded through the catheter 1656 (in the direction 1655), as shown in FIG. 16C, until the therapy delivery portion of the device 102 is located at or near the distal end 1667 of the catheter 1656.

Figure 16D:
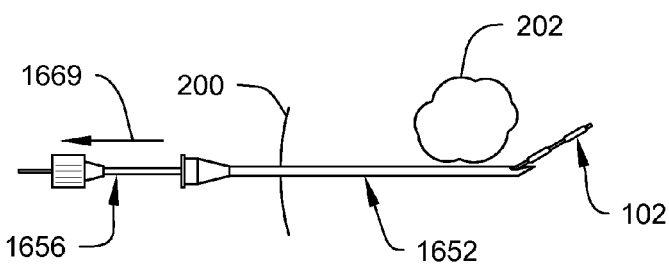
Figure 16E:
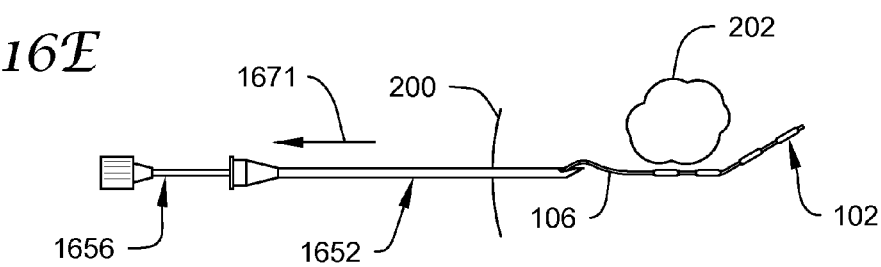

At this point, the catheter 1656 may be withdrawn slightly (in the direction 1669), as shown in FIG. 16D, exposing the therapy delivery portion of the device 102. The needle 1652 and catheter 1656 may then be withdrawn (in the direction 1671) from the body 200 together as shown in FIG. 16E. The device 102 is then implanted on a non-linear axis with its tail portion 106 extending outside the body as generally described above with reference to other embodiments (see e.g., FIGS. 2A-2F).

The ability to implant the device 102 along a non-linear axis may be beneficial in many applications. For example, where the target tissue region 202 is a breast lesion or a lumpectomy cavity in the breast, the non-linear device 102 may provide the capability to better focus radiation. Further, non-linear positioning may permit implantation around obstructions in the body. For example, in prostate brachytherapy, the region 202 could be a pubic arch around which the clinician desires to place radiation sources. While described above with respect to devices 102, the non-linear placement of FIGS. 16A-16E could also be used to implant individual radiation sources.

Figure 16F:
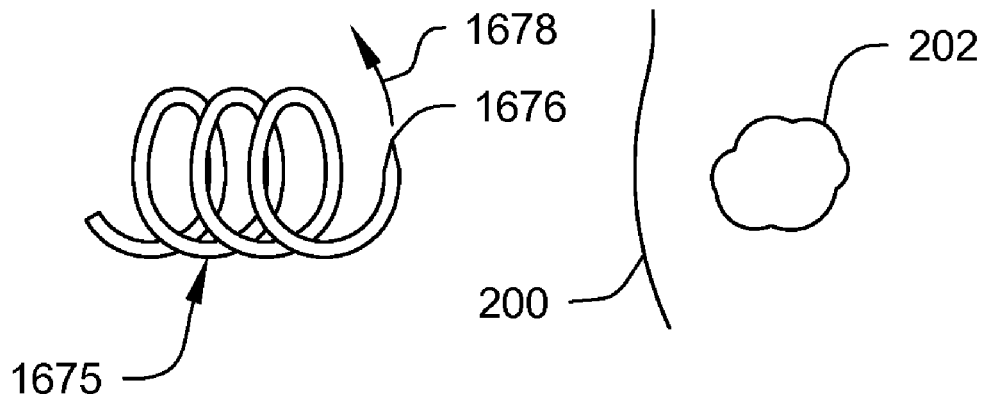
Figure 16G:
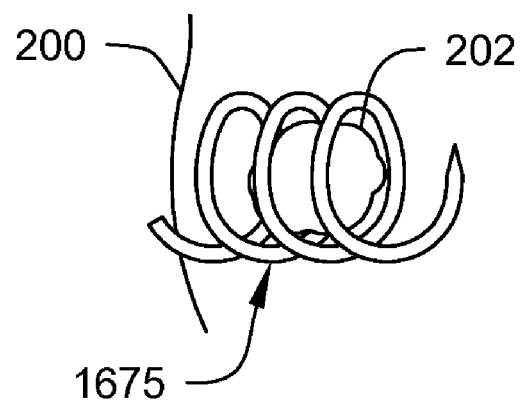

In yet other embodiments of non-linear placement apparatus and techniques, the needle 1652 of FIGS. 16A-16E may be replaced with a more spiral-shaped needle 1675 as shown in FIGS. 16F and 16G. While the actual needle size may vary depending on target tissue volume, needles having a helix diameter of about three centimeters (3 cm) are contemplated. The needle 1675 may be advanced into the body 200 in much the same way a corkscrew is inserted into a cork. That is, the needle 1675 may be rotated in a direction 1678 such that a sharp end 1676 penetrates the body 200 as indicated in FIG. 16F. FIG. 16G illustrates the needle 1675 once it is fully inserted. A flexible catheter (not shown) and therapy device (also not shown) may then be passed through the needle 1675 in much the same way as the catheter 1656 and device 102 are described with reference to FIGS. 16A-16E. The needle 1675 may then removed ("unscrewed"), leaving the therapy device in a spiral configuration around the target tissue region 202 (not illustrated).

When non-linear, e.g., off-axis, curved, and spiral, therapy delivery portions are used, the total number of therapy devices required to treat a given target tissue region may potentially be reduced as a result of the delivery portions conformance to the shape of the target tissue. For example, in the case of curved delivery portions, several devices may be placed to curve around the target tissue region, effectively focusing radiation on a central area. This may result in lower dose exposure outside of the target tissue area, and potentially improved dose coverage within the target tissue. In the case of a spiral therapy delivery portion, a single therapy device of sufficient length may deliver adequate treatment by spiraling (e.g., forming a helix) around or within the target tissue region.

FIGS. 17A-17B illustrate an apparatus 1600 similar in most respects to apparatus 600 of FIG. 6. For instance, it may include a therapy device 1602 having a therapy delivery portion 1604 with seeds 108, and tail portion formed by a suture 1614. The suture 1614 may pass through a pusher member 1620 and the combined pusher member 1620 and delivery device 1602 may be placed within a cannula 1630. Unlike the cannula 630, however, the cannula 1630 may have a cutout 1634, e.g., the cannula may have a C-shaped cross section, as shown more clearly in FIG. 17B, over at least a portion of its length. While shown as straight, the cannula 1630 may also be curved. The cutout configuration may protect certain surrounding tissues/organs, e.g., skin, chest wall, liver, heart, during implantation. FIG. 17B is a cross-section taken along line 17B-17B of FIG. 17A with the therapy delivery device 1602 also shown in broken lines.

Figure 18:
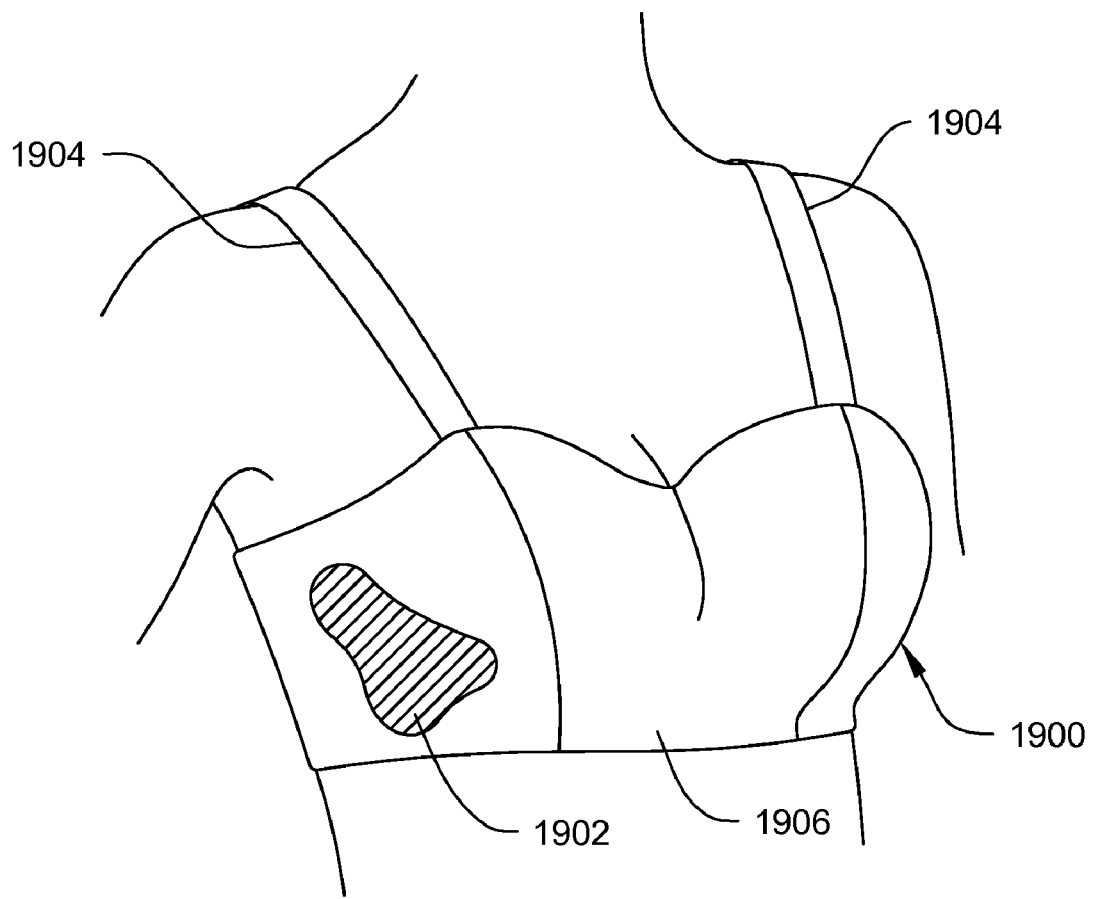
FIG. 18 is a view of a radiation attenuating garment, e.g., brassiere, in accordance with one embodiment.

During implantation of any of the devices described herein, the patient may optionally wear a protective garment, e.g., a chest covering brassiere or binder 1900, such as that illustrated in FIG. 18. The brassiere/binder 1900 may be similar in many respects to those garments described, for example, in U.S. Pat. No. 3,968,803 to Hyman; U.S. Pat. No. 5,152,741 to Farnio; and U.S. Pat. No. 5,538,502 to Johnstone, the disclosures of which are expressly incorporated by reference herein. For example, it may include a partial body covering that secures via fasteners, e.g., shoulder straps 1904, to cover a portion of the chest (or other area surrounding the target tissue region). However, in addition to a fabric portion 1906, the binder 1900 may include a lining made from a radiation attenuating material 1902, e.g., lead, stainless steel, Tungsten. Such a garment may offer an added degree of shielding and permit greater patient mobility, while the indwelling radioactive sources, e.g., seeds 108, are held in their proper position, in an out-patient setting. The garment 1900 may be provided separately, or as part of a brachytherapy kit, e.g., kit 100.

Although discussed above primarily with respect to LDR brachytherapy, the apparatus and/or methods described herein may also find use in HDR applications. For example, the tube 1412 of FIGS. 14A-14B may be used as a shielded delivery catheter for HDR treatment, e.g., the tube 1412 may be located in the body and a conventional HDR source (e.g., afterload HDR cable) of smaller diameter may be passed through the main lumen 1408. The attenuating element 1416 in the wall of the catheter (along a circumferential portion extending from about 10 o'clock to about 2 o'clock, for example) may attenuate the radiation exposure of regions vulnerable to radiation while the non-shielded section of the tube 1412 (along a circumferential portion extending from about two o'clock to about ten o'clock) may allow exposure to the target tissue.

Further, for example, HDR radiation sources may be passed through a catheter, e.g., the cannula 1630 of FIGS. 17A and 17B, whereby the HDR radiation sources may be partially shielded from surrounding tissue by the geometry of the cannula 1630, e.g., the cutout 1634.

FIGS. 19A-19C illustrate incorporation of a HDR shielded catheter on a balloon-type brachytherapy treatment device 1800. The device 1800 may be similar to the device disclosed in U.S. Pat. No. 5,913,813 to Williams et al., the disclosure of which is expressly incorporated by reference herein. For example, it may include a brachytherapy catheter assembly 1802 having a catheter shaft 1814 with a proximal end and a distal end. An inflatable balloon 1806 may be coupled to the catheter shaft 1814 between the proximal end and the distal end. An inflation lumen 1830 may extend along the catheter shaft 1814 between the inflatable balloon 1806 and the proximal end to allow inflation of the balloon. A dose delivery lumen 1804 (see FIG. 19B) may also be provided and extend along the catheter shaft 1814 from the proximal end towards and the distal end, e.g., extending between the inflatable balloon 1806 and the proximal end.

In use, the distal end of the catheter shaft 1814 may be placed into a cavity, e.g., a lumpectomy cavity 1808 of breast 200, and the balloon 1806 inflated. A radiation source (not shown) may then be passed through the dose delivery lumen 1804, where it delivers radiation along a dose delivery portion of the catheter shaft, e.g., along a portion surrounded by the inflatable balloon 1806. By incorporating a radioabsorptive portion (e.g., arc-shaped member 1811 clearly illustrated in FIG. 19C) over the dose delivery portion of the catheter shaft 1814, only a predetermined portion, e.g., a window 1817, of the dose delivery portion may be relatively radiotransparent. As a result, the device 1800 may attenuate the radiation exposure of select areas, e.g., those close to the skin or chest wall, while delivering higher radiation levels to target tissue not blocked by the radioabsorptive portion 1811. While the radioabsorptive portion is illustrated herein as a separate member 1811 extending along a portion of the catheter shaft 1814, other embodiments may incorporate the radioabsorptive portion into the catheter shaft 1814 itself (e.g., the catheters described elsewhere herein, such as the tube 1412 of FIGS. 14A-14B).

In some embodiments, the device 1800 may further include a vent system having one or more vents 1810 positioned around at least a portion of an outer surface of the balloon 1806. The vents 1810 may permit air and fluids within the cavity 1808 to escape as the balloon 1806 expands. One or more vent lumens 1812 (shown in FIG. 19B) associated with the catheter shaft 1814 may extend between the proximal end of the catheter shaft 1814 and the one or more vents 1810. The vents 1810 may fluidly communicate with one or more vent lumens 1812, thereby allowing the air and fluids to exit the body at the proximal end of the catheter shaft 1814 during and after balloon expansion.

In some embodiments, the external vents 1810 and vent lumens 1812 are formed by individual pieces of tubing 1816 attached to the balloon 1806 and catheter shaft 1814. In the vicinity of the balloon 1806, the tubing 1816 may be perforated to form the external vents 1810. The portion of the tubing 1816 located proximate the catheter shaft 1814 may or may not include perforations. The tubing 1816 may be formed of most any biocompatible material that can be securely attached to, or formed with, the balloon 1806 and catheter shaft 1814, e.g., silicone tubing.

Figure 20:
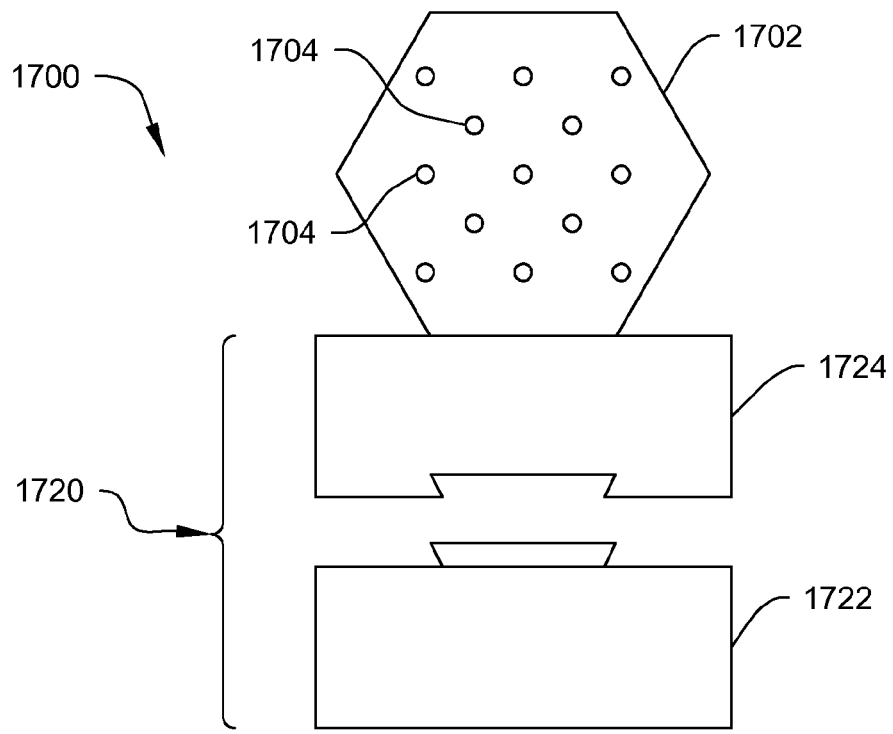
FIG. 20 is an exemplary embodiment of a delivery or implantation system for use with the brachytherapy methods and apparatus described herein.
Figure 21:
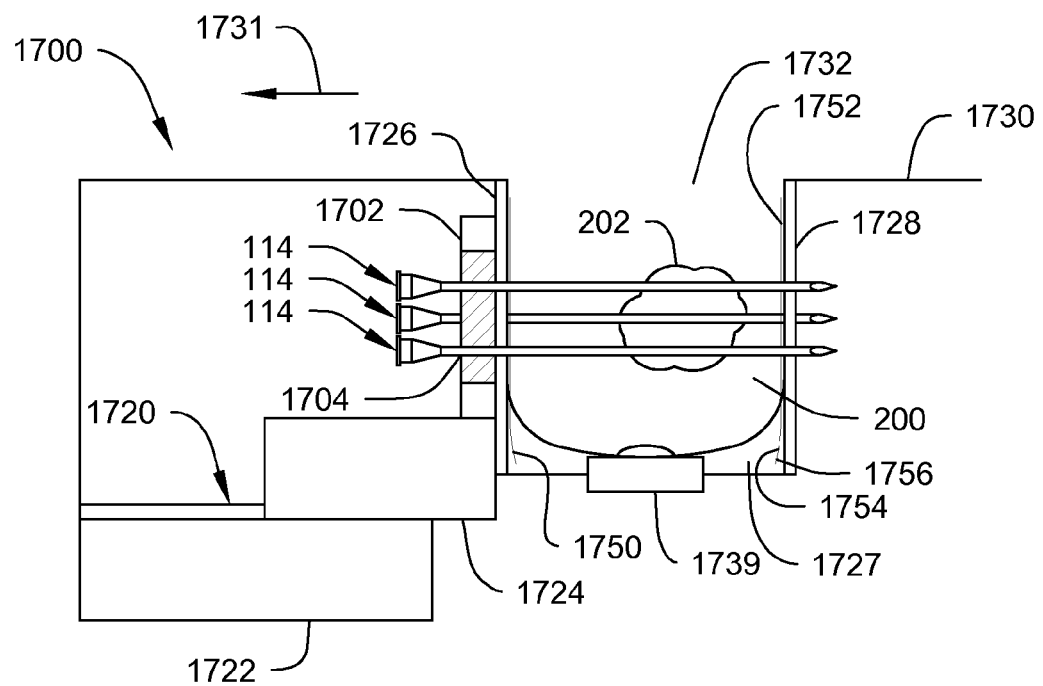
FIG. 21 is a diagrammatic view of the delivery system FIG. 20 as it may be used with the brachytherapy methods and apparatus described herein, e.g., the methods described in FIGS. 2A-2F and 8A-8E.
Figure 22:
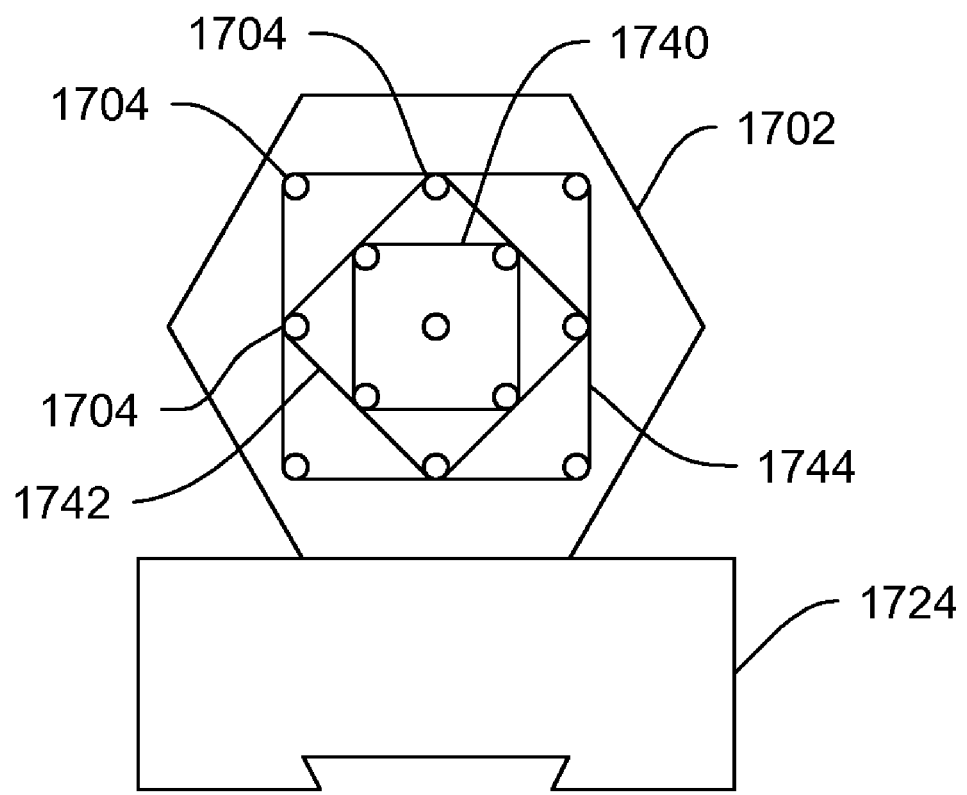
FIG. 22 is an enlarged view of an exemplary catheter, e.g., needle, guiding template for use with the delivery system of FIG. 21.

FIGS. 20-22 illustrate an exemplary system 1700 for implanting the LDR brachytherapy devices and their associated radiation sources described above to a target tissue region, e.g., the region surrounding a breast lumpectomy cavity. In the illustrated embodiment, the system includes a catheter or needle guiding template 1702 having a predetermined number and pattern (array) of openings 1704 as shown in FIG. 20. The template 1702 may form part of an adjustable catheter or needle guiding apparatus by coupling to a stereotactic table 1720, which is diagrammatically illustrated in the figures by base portion 1722, and translating portion 1724 (portions 1722 and 1724 shown exploded in FIG. 20). The stereotactic table 1720 is preferably coupled or attached to a patient locating or treatment surface 1730, e.g., patient table.

The template 1702 may be coupled to, or otherwise associated with, a first compression member 1726 located adjacent an opening 1732 in the treatment surface 1730. An opposing second compression member 1728 may be located on an opposite side of the opening 1732. The compression members 1726 and 1728 may be oriented about ninety degrees (90°) from a set of optional compression plates 1727 (only one plate 1727 shown).

One or both compression members 1726, 1728 may include a hole pattern similar to that of the template 1702, or may otherwise at least permit the passage of the needles/cannulae (e.g., needles 114 of FIG. 1), as illustrated in FIG. 21.

In use, a patient may lie on the treatment surface 1730, e.g., with the patient's head located in the direction 1731, such that the breast 200 passes through the opening 1732 of the treatment surface 1730. The optional compression plates 1727 may then be used to immobilize the breast 200.

Once the breast 200 is immobilized, the stereotactic table 1720, with the template 1702 attached, may be positioned, and the translating portion 1724 moved, until the compression members 1726 and 1728 contact the breast 200. The position of the stereotactic table 1720, and thus the needle guiding template 1702, may be aligned with the location of the target tissue region 202 via the use of various imaging techniques including, for example, X-ray, ultrasound and CT scan. In some embodiments, the template 1702 may be aligned relative to the target tissue region based upon input provided by an imaging device, e.g., a side viewing ultrasound apparatus 1739, located underneath the breast 200.

With the template 1702 aligned with the target tissue region 202 and positioned against the breast 200, one or more needles 114 may be inserted into the openings 1704. In the treatment of breast lesions, the needles 114 may be inserted completely through the breast 200 as illustrated in FIG. 21. Alternatively, and in the treatment of other cancers, the length of each needle 114 may be varied to ensure the correct depth penetration at each opening 1704, or the insertion depth of each needle 114 may simply be varied.

Certain embodiments of the system 1700 may optionally include an adhesive bandage member 1750 associated with the first compression member 1726, and/or an adhesive bandage member 1752 associated with the second compression member 1728. Preferably, the bandage members 1750 and 1752 are located between the respective compression members and the breast 200. The bandage members 1750 and 1752 may have adhesive on each side, e.g., a first side 1754 and a second side 1756, and include openings (not shown) that correspond generally to the openings 1704 of the template 1702. Alternatively, the bandage members 1750 and 1752 may be punctured by the needles 114 during needle insertion. When the compression members 1726 and 1728 are pressed against the breast 200, the bandage members 1750 and 1752 may adhere to the breast 200 and provide a dressing for the punctures created by the needles 114.

Once the needles 114 are inserted, the brachytherapy devices described herein, e.g., devices 102 or 602, may be inserted, and the needles 114 removed, in accordance with various methods as described and illustrated herein. For example, the brachytherapy devices 102 (or devices 602) may be inserted and the needles 114 (or the cannulae 630) removed in accordance with the methods described herein and illustrated in FIGS. 2A-2E and 2F (or 8A-8E).

With the needles 114 removed, the template 1702 and contact plates 1726 and 1728 may be withdrawn from the breast 200, leaving the bandage members 1750 and 1752 adhered to the breast by their respective first adhesive sides 1754. The tail portions 106 may then be anchored, e.g., by using locking members such as members 120 illustrated in FIGS. 2E and 27.

A liner (not shown) may then be removed from the respective second adhesive side 1756 of each bandage member 1750 and 1752. Once the second adhesive side 1756 is exposed, the flexible tail portions 106 may be folded against the second adhesive side, where they adhere thereto. A second, single-sided adhesive member (not shown) may be placed over each bandage member 1750 and 1752 to secure the tail portions and cover any exposed adhesive on the second adhesive side 1756. As a result, the flexible tail portions may be folded against the contours of the breast and secured.

In some embodiments, the openings 1704 of the template 1702 may be grouped according to a particular target tissue volume, e.g., lesion size, as shown in FIG. 22. For example, a small square, five-opening pattern 1740 may be utilized for small target tissue regions (e.g., those regions up to about one centimeter (1 cm) in diameter), while a larger nine-opening pattern 1742 may be utilized for larger target tissue regions (e.g., those regions up to about two centimeters (2 cm) in diameter). A still larger, thirteen-opening pattern may be utilized for even larger target tissue regions (e.g., those regions up to about three centimeters (3 cm) in diameter).

By aligning the center opening of the template 1702 with the center of the target tissue region, the template may indicate a standard number of seeds, e.g., a particular number of therapy devices 102, based upon the predetermined target volume. This could simplify, or possibly eliminate, the need for complex dose mapping calculations commonly associated with conventional brachytherapy methods.

It is noted that the patterns 1740, 1742, and 1744 are exemplary only. In other embodiments, the patterns may include most any number of openings 1704 in most any shaped pattern, e.g., a circular array of five to fifty (5-50) catheters. Moreover, the templates could accommodate more that one diameter catheter or needle (e.g., ten, fifteen, and twenty millimeter (10, 15, and 20 mm) diameters). Moreover, while shown with three patterns, templates having most any number are possible without departing from the scope of the invention.

Figure 23:
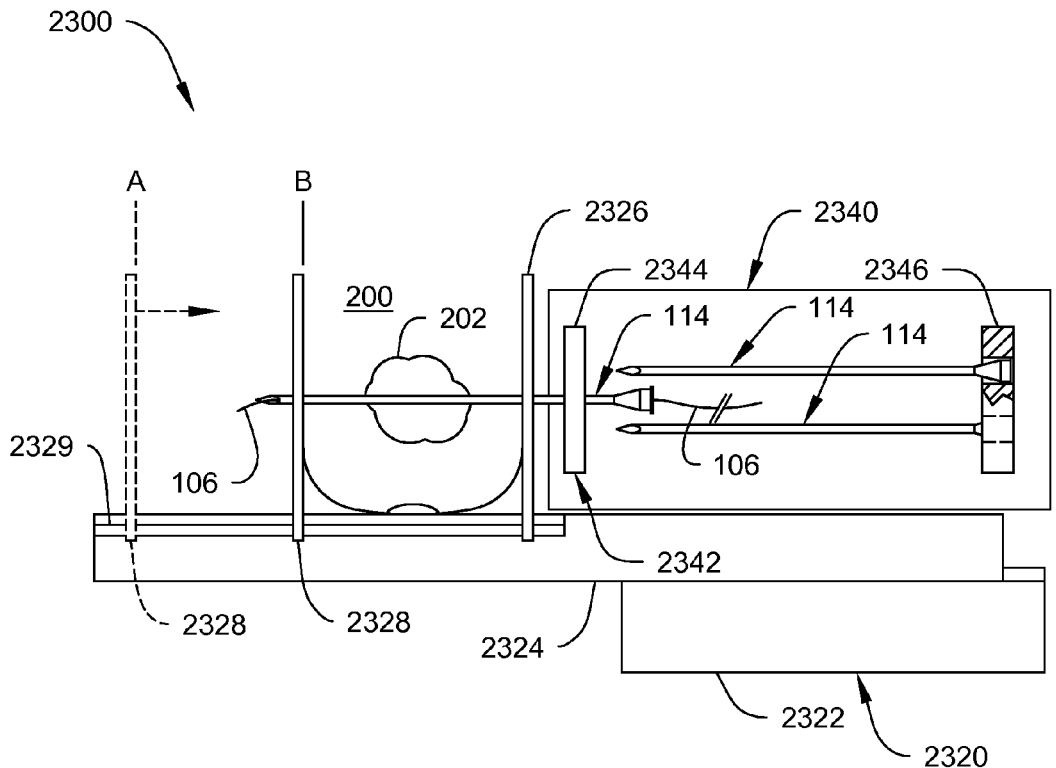
FIG. 23 is a diagrammatic view of another delivery or implantation system for use with the brachytherapy methods and apparatus described herein.
Figure 24:
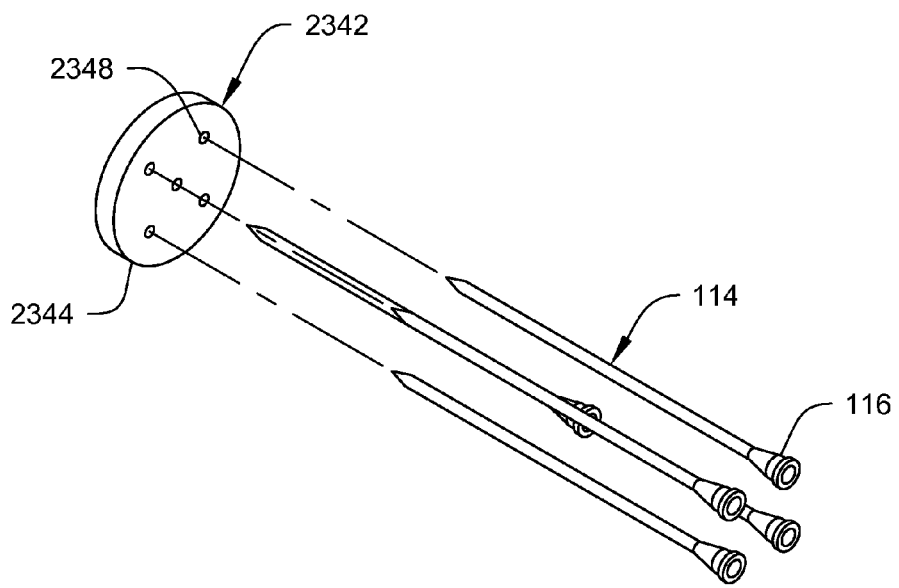
FIG. 24 is an exploded view of a portion, e.g., a cartridge, of the delivery system of FIG. 23.

FIGS. 23 and 24 illustrate another system for implanting brachytherapy devices. FIG. 23 illustrates a system 2300 similar in many respects to the system 1700 described above. For instance, the system 2300 may include a stereotactic table 2320 secured to treatment surface, e.g., patient table (not shown). The table 2320 may include a base portion 2322 and a translational portion 2324. The system 2300 may also include a first or proximal compression member 2326 and a second or distal compression member 2328. One or both compression members 2326 and 2328 may be movable relative to the other and/or the base portion 2322, e.g., along a slide rail 2329.

Unlike the system 1700, however, the system 2300 may also include a catheter or needle cartridge receiver 2340 operable to receive a pre-assembled needle cartridge 2342 having multiple needles 114 positioned in a predetermined array. The needle cartridge 2342 is shown in an exploded view in FIG. 24. The cartridge 2342 may include a first holder 2344 and a second holder 2346 (second holder 2346 not shown in FIG. 24). The holders 2344 and 2346 may include holes 2348 to hold and guide the multiple needles 114 in the desired predetermined array during insertion. Where needles 114 include a hub 116, the holes 2348 in the holder 2346 may be larger than the corresponding holes 2348 in the holder 2344 to permit the passage of the hub 116 (see FIG. 23).

During operation of the system 2300, the stereotactic table 2320 may be aligned as described above with respect to the system 1700. Once aligned, the breast 200 may be immobilized with the compression members 2326 and 2328. Based upon the particular volume of the target tissue region 202, a specific cartridge 2342 may be selected and pre-assembled with a corresponding number of catheters, e.g., needles 114. For instance, the cartridge in FIG. 24 is a 5 catheter configuration. However, other cartridges may utilize more or less catheters (e.g., 9 catheter and 13 catheter cartridges). The cartridge 2342, including the holders 2344 and 2346 and the catheters 114, may then be loaded into the cartridge receiver 2340. Portions of the holders 2344 and 2346 may be designed to contact one or more internal surfaces of the cartridge receiver 2340 so that the cartridge 2342 aligns with the cartridge receiver upon insertion.

Once the cartridge 2342 is loaded, each needle 114 may be independently and manually advanced through the proximal compression plate 2326 (which may include a hole pattern identical to the holder 2344), the breast 200, and the distal compression member 2328. The central needle 114 may be advanced first and its position within the target tissue region 202 confirmed (or repositioned) before the remaining needles are advanced. Brachytherapy devices, e.g., devices 102 of FIG. 1, may then be placed into the needles 114, as described in FIGS. 2A-2E. Alternatively, the devices 102 could be pre-installed in the cartridge 2342.

With the devices 102 inserted completely, the distal tips of the tail portions, e.g., similar to tail portion 106 of FIG. 1, may be temporarily secured relative to the distal compression member 2328. At this point, the needles 114 may be retracted and removed from the breast 200, and ultimately, withdrawn from the cartridge loader 2340. The proximal compression member 2326 may then be withdrawn and the proximal tail portions secured to the breast using, for example, the locking devices 120 described above and illustrated in FIGS. 2E and 27. The distal compression member 2328 may then be withdrawn and the distal tail portions secured relative to the breast 200 in a similar manner.

Figure 25A:
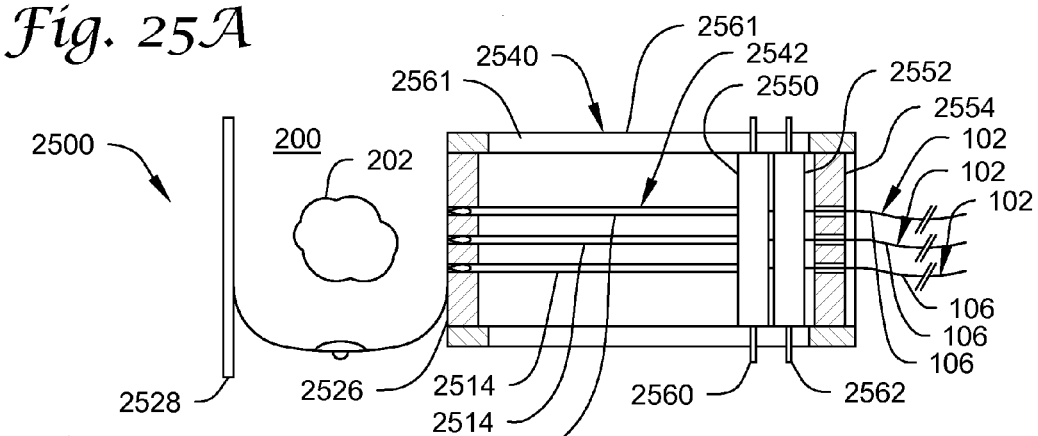
FIGS. 25A-25D are diagrammatic illustrations of a delivery or implantation system and method in accordance with yet another embodiment.

FIGS. 25A-25D illustrate yet another system and method for inserting the brachytherapy devices into a target tissue region. FIG. 25A illustrates a system 2500 similar in many respects to the systems 1700 and 2300 described above. For example, the system 2500 includes a stereotactic table (not shown) having a catheter or needle cartridge receiver 2540 coupled thereto. The stereotactic table is preferably coupled to the treatment table (also not shown). The system 2500 may also include a catheter or needle cartridge 2542. The needle cartridge 2542 may include a series of needles 2514, e.g., a five, none, or thirteen needle array, which are generally rigidly and orthogonally mounted to a first plunger member 2550. In this embodiment, the needles 2514 may be hubless as the proximal ends of the needles 2514 are secured (e.g., press fit, staked, adhered, etc.) to the first plunger member 2550.

The cartridge 2542 may also include a first or proximal compression member 2526 (which may form the needle guiding template) as well as a second plunger member 2552 and an optional backing plate 2554. In other embodiments, the backing plate 2554 may be part of the cartridge receiver 2540. As with the systems previously described herein, the system 2500 may also include a second or distal compression member 2528 to assist in immobilizing the breast 200.

During operation, the stereotactic table may be aligned such that the center of the needle cartridge receiver 2540 is centered relative to the target tissue region 202. The cartridge 2542 may then be loaded into the cartridge receiver 2540, and the breast immobilized by the first and second compression members 2526 and 2528. The brachytherapy devices, e.g., devices 102 of FIG. 1, may have been previously loaded into the needles 2514 of the cartridge 2542. The first plunger member 2550 may then be advanced toward the breast 200. Because the needles 2514 are rigidly coupled to the first plunger member 2550, the needles 2514 advance simultaneously into the target tissue region of the breast 200 in the pre-determined parallel array. The first plunger member 2550 may include a tab 2560 that rides along a slot or surface 2561 of the cartridge receiver 2540 so that the first plunger member 2550 may be manually or automatically advanced from outside the cartridge.

Figure 25B:
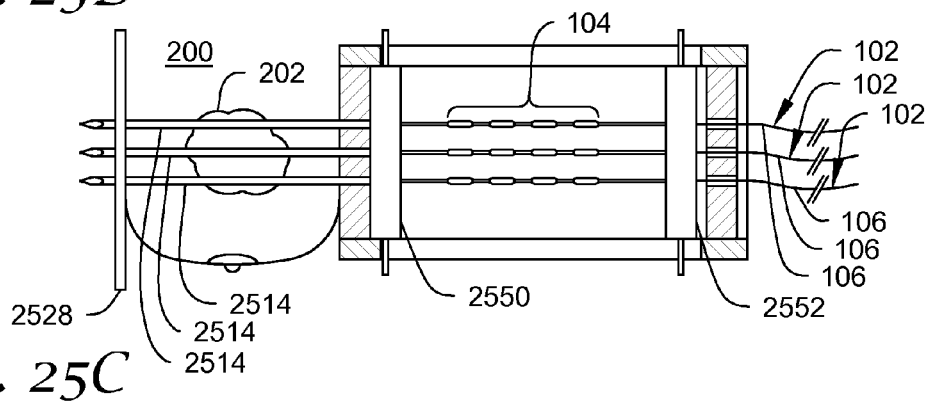
Figure 25C:
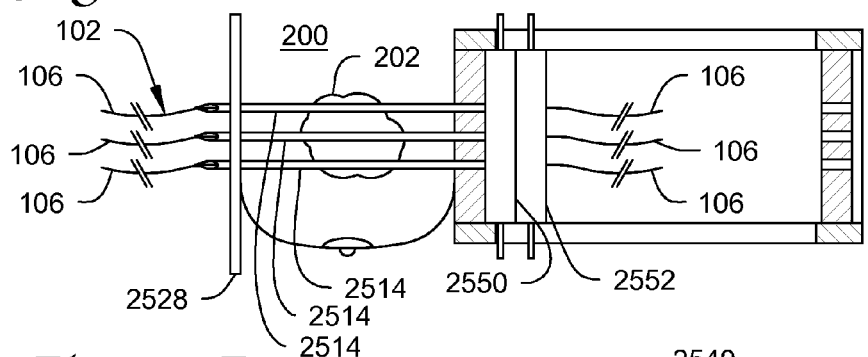

After the first plunger member 2550 has been fully advanced as shown in FIG. 25B, the second plunger member 2552 may be advanced toward the breast 200. The second plunger member 2552 has the proximal tail portions 106 of the brachytherapy devices 102 releasably secured thereto. Thus, advancing the second plunger member 2552 may advance one or more of the brachytherapy devices 102 into place such that the distal tail portions 106 emerge from the distal ends of the needles 2514 as shown in FIG. 25C.

Figure 25D:
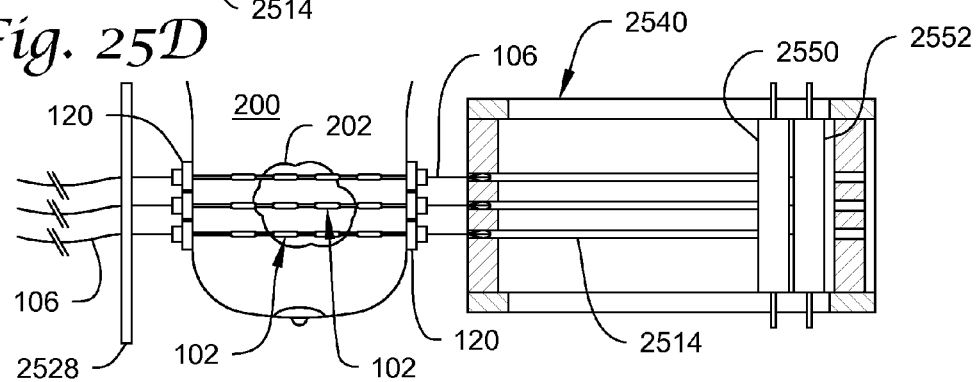

The distal tail portions 106 may temporarily be secured to the distal compression member 2528 to hold the brachytherapy devices 102 in place. Once the distal tail portions 106 are secured, the proximal tail portions 106 may be released from the second plunger member 2552 and the first and second plunger members 2550 and 2552 may be retracted as shown in FIG. 25D. The cartridge receiver 2540 may also be retracted so that the proximal tail portions 106 may be secured in accordance with methods already described herein (e.g., locking members 120). The distal tail portions 106 may then be disconnected from the distal compression member 2528 and the latter withdrawn. The distal tail portions 106 may then be secured relative to the breast 200.

Thus, the system 2500 provide an apparatus for simultaneously implanting, in a two dimensional array, multiple brachytherapy devices into the body. Moreover, the systems described herein allow simultaneously advancing a two-dimensional array of catheters into a target tissue region, and then delivering or implanting one or more radiation sources through at least one of the catheters of the array. Once the radiation sources are implanted, sequential or simultaneous removal of the catheters of the array of catheters from the target tissue region may be accomplished.

Each radioactive source, e.g., seed 108, of the devices described herein may have substantially the same radioactivity level as the other seeds within the same device. However, any of the embodiments described herein may vary brachytherapy by utilizing seeds that have differing levels of radioactivity within the same brachytherapy device. Stated another way, a first radioactive source (e.g., first seed) of the device may have a first radioactivity level (e.g., about five millicuries (5 mCi)), while a second radioactive source (e.g., second seed) of the same device may have a second radioactivity level that is less than the first radioactivity level (e.g., about one millicurie (1 mCi)). Likewise, in multi-device applications, each seed within a given device could have identical radioactivity levels, but different devices within the array could contain seeds of different radioactivity levels.

Figure 26:
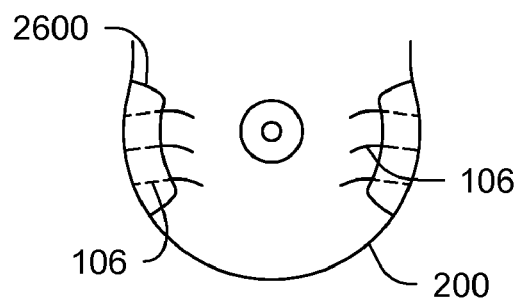
FIG. 26 is a view of a portion of a human body, e.g., a female breast, after the brachytherapy devices as described herein have been implanted and secured.

As already described above, some embodiments may permit the tail portions 106 to be secured to the breast using an adhesive pad or bandage 2600 as illustrated in FIG. 26. Here, the bandage may be used in conjunction with, or as an alternative to, the locking members 120.

To assist the healthcare provider in securing the distal and/or proximal tail portions 106, the compression members 2526, 2528 may be configured as generally illustrated in FIG. 27. For example, openings 2570 in the plate (e.g., plate 2528) through which the tail portions 106 pass may include a recess 2572 that holds the locking member 120 against the skin. As a result, when the compression plate 2528 is withdrawn, the locking member 120 may already be threaded over the tail portion 106. The healthcare provider may then quickly crimp the locking member 120, e.g., along a deformable portion 2576.

While many of the devices and apparatus described herein are directed to linear placement, it may be of benefit to locate radioactive sources within a tumor or lumpectomy cavity in a more sophisticated geometry. For instance, devices may be implanted in a non-linear manner as described above with reference to FIGS. 16A-16G. Geometries that are curved rather than straight may allow better conformance to the target tissue (e.g., better conformance to the tissue surrounding the curvilinear volume of a lumpectomy cavity).

Moreover, apparatus, devices, and systems in accordance with other embodiments described herein may permit implantation of brachytherapy devices in a first or collapsed, e.g., substantially straight, configuration, after which they may be externally actuated to a second or deployed, e.g., curvilinear, configuration once located within the target tissue region, e.g., within a lumpectomy cavity. Stated alternatively, such embodiments may provide a brachytherapy treatment apparatus for insertion into the target tissue region of a body, e.g., breast, wherein the apparatus includes one or more brachytherapy devices having one, and preferably more, radioactive sources such as those already described herein (e.g., see device 102). The brachytherapy device may be inserted into the target tissue region in a generally linear configuration. However, it may then be subsequently reconfigured to produce a curvilinear array of radioactive sources, e.g., as further described below.

Such apparatus and devices may permit implantation through a single, minimally-sized incision, yet may subsequently deploy in-situ to provide a dose delivery region that is geometrically better suited to the curvilinear shape of the target tissue (e.g., the region of tissue surrounding the lumpectomy cavity). In addition, the deployed configuration may provide a broader array from which radiation sources may deliver their desired dose, as compared to the first collapsed configuration.

Additionally, in-situ deployable apparatus, devices, and systems as described herein may enhance fixation of the radiation sources within a specific location of the lumpectomy cavity. Fixation is beneficial in that it provides a substantially fixed geometry between the implanted radiation sources and the surrounding target tissue. By minimizing movement of the radiation sources (relative to the target tissue) during subsequent patient activity, brachytherapy exposure may more closely follow pre-implant dose planning regimens.

One embodiment of such a deployable apparatus is diagrammatically illustrated in FIGS. 28A-28D by an expanding cage-type apparatus 2800. Generally, the intracavitary apparatus 2800 includes a therapy delivery portion 2800a, which may be deployed within a target location of a patient's body, e.g., tumor or cavity within a breast or other body structure 200, and a tail portion 2800b, which extends from the therapy delivery portion 2800a, e.g., such that the tail portion 2800b protrudes outside of the body structure 200. As shown in FIGS. 28A-28D, the therapy delivery portion 2800a may be movable between a collapsed configuration, e.g., for introduction through a tissue tract to a target location, and an expanded configuration, e.g., for providing a three dimensional array of pathways at the target location 2802, as described further below.

Optionally, the apparatus 2800 may include a sheath or other cover (not shown), which may overly the therapy delivery portion 2800a, e.g., until deployment. In addition or alternatively, a tubular delivery device, such as catheter, cannula, or needle 2804, may be provided for introducing the apparatus 2800 into the target location. A trocar or other instrument (not shown) may be disposed within the needle 2804 such that a sharpened tip (also not shown) of the trocar extends beyond a distal end 2804a of the needle 2804 to facilitate insertion of the needle 2804 through tissue, e.g., to create a tissue tract from the patient's skin to the target location. The trocar may be removed after creating the tract, thereby allowing the apparatus 2800 to then be introduced into the needle 2804.

Alternatively, the needle 2804 may include a sharpened distal tip (not shown). In this alternative, the trocar may be eliminated, and, optionally, an obturator or other instrument (also not shown) may be initially provided to occlude the lumen while the needle 2804 is advanced through tissue. After removing the obturator, the apparatus 2800 may be introduced into the needle 2804, e.g., directly or carried within a sheath or cover (not shown).

In a further alternative, the apparatus 2800 may include a sharpened distal tip (not shown), e.g., similar to other embodiments described below. The distal tip may extend beyond the distal end 2804a of the needle 2804, thereby creating the tract when the needle 2804 and apparatus 2800 are advanced together through tissue. In yet another alternative, the apparatus 2800, with a sharpened distal tip, may be advanced directly through tissue to create the tissue tract, and the needle 2804 may be eliminated.

Figure 28A:
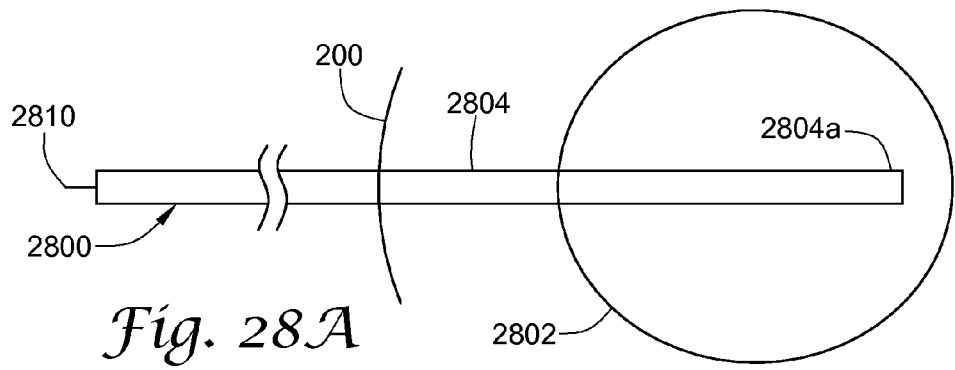

FIG. 28A illustrates the brachytherapy apparatus 2800 after insertion through an incision in the body. The apparatus 2800 is positioned such that the therapy delivery portion 2800a is located within a hollow target region, e.g., lumpectomy cavity 2802. As illustrated in FIG. 28A, a catheter or needle 2804 has been inserted through the body structure, e.g., breast 200, and into the cavity 2802. Once the apparatus 2800 is in place, the needle 2804 may be retracted or removed, exposing the therapy delivery portion 2800a.

Figure 28B:
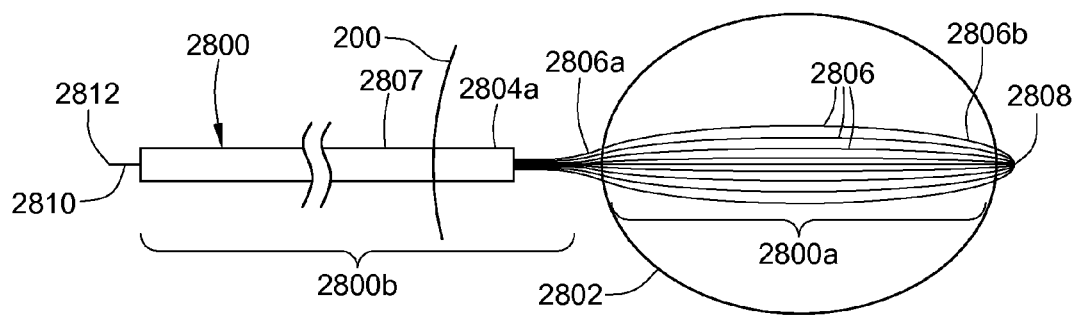

As shown, the therapy delivery portion 2800a includes a plurality of radioactive brachytherapy devices, e.g., flexible, elongate members 2806 including proximal and distal ends 2806a, 2806b and configured for carrying one or more radiation sources. The apparatus 2800 includes a hub or outer body member 2807 to which the proximal ends 2806a of the elongate members 2806 are secured, as shown in FIG. 28B. The distal ends 2806b of the elongate members 2806 may be fixed or otherwise retained at a distal end 2808 of a core member 2810. As shown, the core member 2810 extends through the body member 2807 such that a proximal end 2812 of the core member 2810 extends out of the body structure 200. Alternatively, a handle (not shown) may be coupled or otherwise extend proximally from the core member 2810.

Figure 28C:
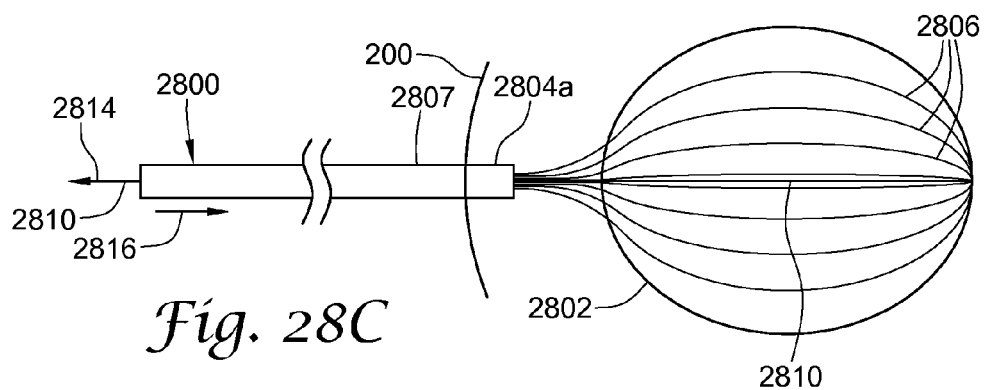
Figure 28D:
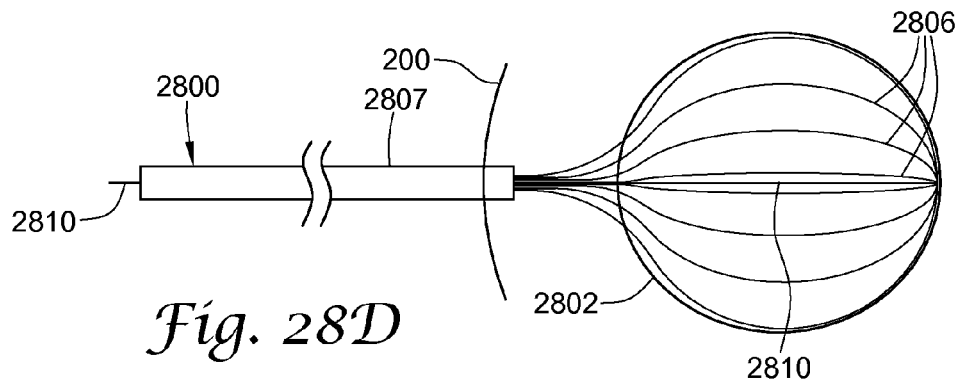

The hub and core member 2810 may be movable axially relative to one another to expand and/or collapse the therapy delivery portion 2800a. For example, by manipulation of the proximal end 2812 of the core member 2810 and the body member 2807, e.g., by displacing the core member 2810 in a first (proximal) direction 2814 and/or the body member 2807 in a second (distal) direction 2816, the elongate members 2806 may be expanded within the volume of the cavity 2802, as shown in FIG. 28C. When fully expanded, the elongate members 2806 may contact walls of the cavity 2802, as shown in FIG. 28D, and/or push into tissue surrounding the walls of the cavity 2802, as described further below.

Figure 29B:
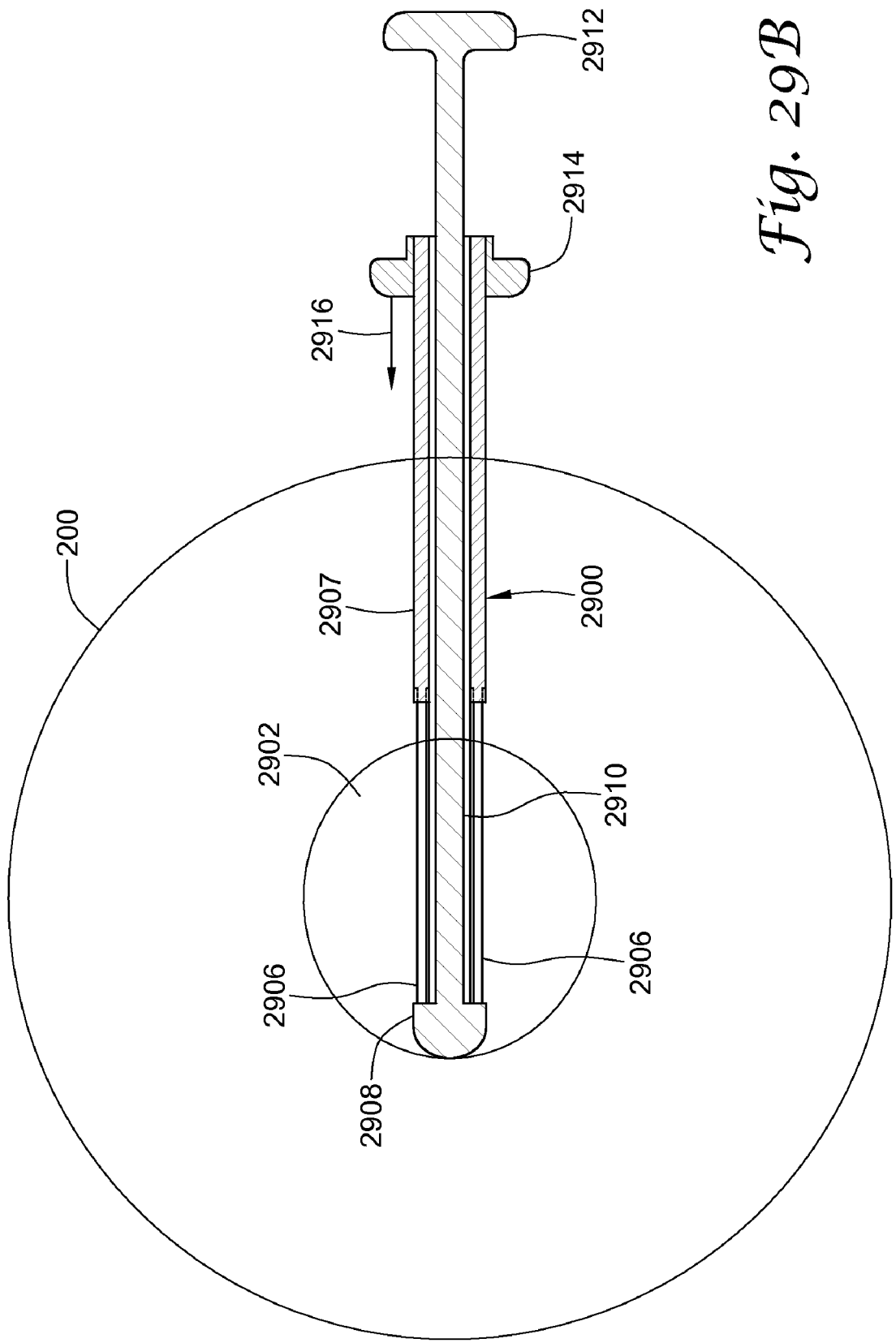

FIGS. 29A-29F illustrate another embodiment of an in-situ deployable brachytherapy apparatus 2900. The apparatus is similar in many respects to the apparatus 2800 described above. For example, the apparatus 2900 may include an expandable cage of radioactive brachytherapy devices, e.g., flexible, elongate members 2906. Each elongate member 2906 may, at a distal end 2906b, couple to a hub 2909 and, at a proximal end 2906a, couple to a body member 2907. A flange 2914 may be provided at a proximal end of the body member 2907, as shown in FIG. 29A. A core member 2910, also coupled to the hub 2909, may extend through the body member 2907 and past the flange 2914, terminating at a button or other handle 2912.

The elongate members 2906 may terminate, at their proximal ends 2906a, within the body member 2907. However, as explained further below, other body member embodiments may include passageways that provide access to lumens formed in the elongate members 2906 from a proximal side of the flange 2914.

The apparatus 2900 may be moved from a first collapsed configuration, wherein the elongate members 2906 are generally straight and parallel to a central axis of the core member 2910 (see FIG. 29B), to a second deployed configuration, as shown in FIGS. 29A and 29C, wherein the elongate members 2906 are curvilinear. For example, movement to the deployed configuration may be achieved by moving the flange 2914, and thus the body member 2907, away from the button 2912 (i.e., in the distal direction 2916). Similarly, the apparatus 2900 may be collapsed by moving the flange 2914 towards the button 2912 (i.e., in the proximal direction 2918).

It will be appreciated that other actuators may be provided in addition to the flange 2914 and button 2912. For example, the core member 2910 and body member 2907 may include mating threads (not shown), e.g., on an inner surface of the body member 2907 and an outer surface of the core member 2910 within the body member 2907. Rather than axial movement of the button 2912, the button 2912 may be rotated in a first direction, thereby causing the body member 2907 to move axially, i.e., distally, over the core member 2910 to expand the elongate members 2906 to the expanded configuration. The button 2912 may be rotated in a second opposite direction to collapse the elongate members 2906 back to the collapsed configuration.

Optionally, in any of these embodiments, the button 2912 and/or portion of the core member 2910 beyond the flange 2914 may be detachable from the rest of the core member 2910 (within the body member 2907 and extending to the hub 2909), e.g., to reduce a profile of the apparatus 2900 after implantation. For example, the core member detachable portion and remaining portion (not shown) may include mating male/female ends, e.g., connected by threads or other releasable connectors (also not shown). Alternatively, a barrel or other structure may be disposed within the body member 2907 that is coupled to the proximal ends 2906a of the elongate members 2906 such that axial movement of the barrel relative to the body member 2907 causes expansion or collapse of the elongate members 2906.

In another option, the core member 2910 (and/or actuator) may include one or more stops (not shown) to limit movement of the body member 2907, e.g., to limit expansion of the elongate members 2906. The stops may provide a maximum size for the expanded configuration or may provide a range of sizes through which the elongate members 2906 may be expanded and fixed. For example, ratchets or detents (not shown) may allow the body member 2907 to be moved, yet maintained at a position to which the body member 2907 is moved relative to the core member 2910.

FIGS. 29B and 29C illustrate the brachytherapy apparatus 2900 after insertion through an incision in the body structure, e.g., breast 200. The apparatus 2900 may be positioned such that its distal end, e.g., hub 2908, is located within the lumpectomy cavity 2902. In the illustrated embodiment, the apparatus 2900 is inserted through an existing incision. However, the apparatus 2900 may have features (e.g., a sharp distal tip) that permit it to make its own incision, as described above. The sharp distal tip may enable the tip of the apparatus 2900 to be positioned beyond the edge of the cavity, e.g., in order to position the expanded elements in an optimal position within the cavity.

In some embodiments, the apparatus 2900 may include a tear-away sheath (not shown) that covers the elongate members 2906 during handling and/or implantation. After the apparatus 2900 is positioned as shown in FIG. 29B, the sheath may be removed (e.g., using a tear-strip positioned outside the body and/or one or more weakened seams or regions extending along the sheath) to expose the elongate members 2906.

Once the apparatus 2900 is in place, e.g., as shown in FIG. 29B, the physician may displace the flange 2914 towards the body (in the distal direction 2916). Similarly, the button 2912 may be displaced proximally away from the flange 2914. This motion causes the elongate members 2906 to deploy, as shown in FIG. 29C, within the volume of the cavity 2902. When further expanded, the elongate members 2906 may contact the walls of the cavity and, when fully expanded, may press into the surrounding tissue sufficiently to cause the cavity walls to reconfigure in an interdigitating manner between the members 2906 (see, e.g., FIGS. 32D-32G, as described further below). This interdigitation or invagination of the walls results in generally fixing the apparatus 2900 relative to the tissue surrounding the cavity 2902.

As used herein, the terms "invagination" and "interdigitation" refer to pressing of one or more portions or elements of the apparatus 2900 outwardly from within a cavity 2902, into the tissue surrounding the cavity 2902, such that tissue adjacent the elements flows, folds, or extrudes inwardly between the elongate members 2906. FIGS. 32D-32H, for example, illustrate this concept. In addition to being substantially surrounded by tissue, one or more of the elongate members 2906 may penetrate into the surrounding tissue, e.g., such that the elongate member(s) 2906 may be completely surrounded by tissue, as described further below.

Figure 29D:
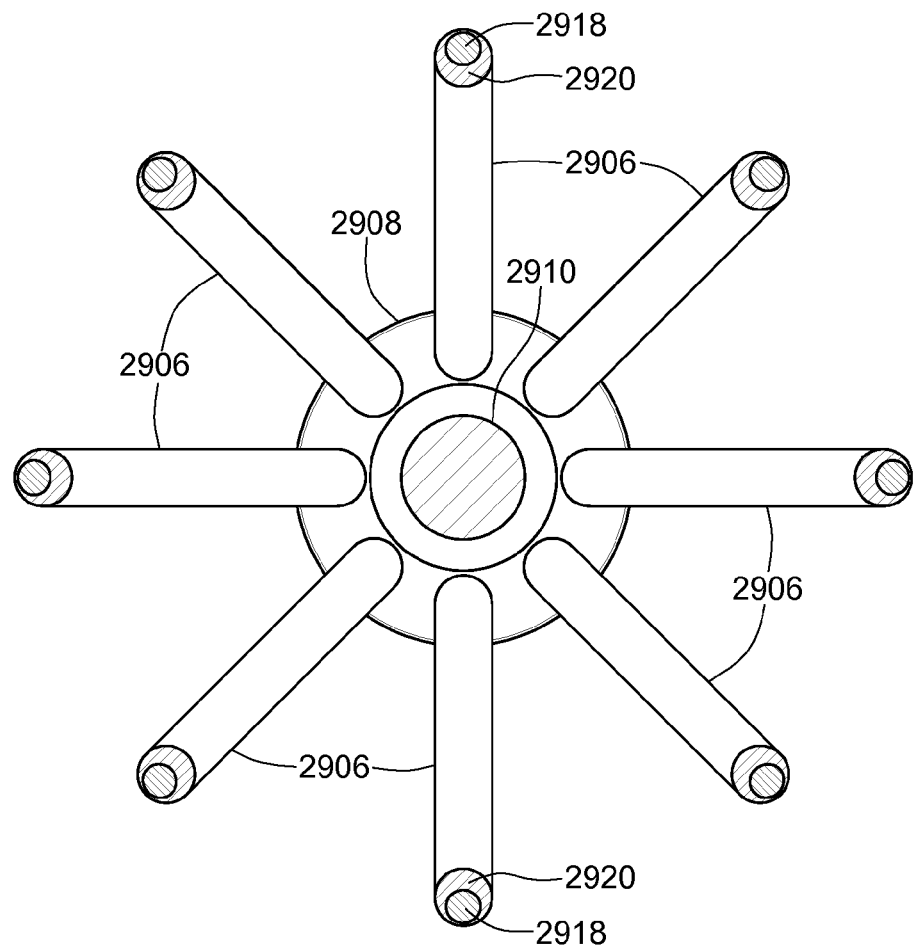

FIG. 29D is a cross-sectional view of the apparatus 2900, taken along line 29D-29D of FIG. 29C. As shown in this view, the elongate members 2906 may be tubular members including one or more lumens, e.g., a first lumen 2918 and a second lumen 2920. The first lumen 2918 may be sized to receive a brachytherapy device, e.g., similar to the devices 102, 152, 402, 502, and 602 already described elsewhere herein. The second lumen 2920 may, on the other hand, be configured to hold a stiffening member (not shown). The stiffening member may assist in maintaining the proper orientation of the elongate members 2906, e.g., may assist in ensuring that the lumens 2918 (and, thus, the brachytherapy devices) are sufficiently stiff so as to prevent their deflection during expansion into the surrounding tissue and/or ensure that the elongate members 2906 expand substantially in a predetermined configuration.

Figure 29E:
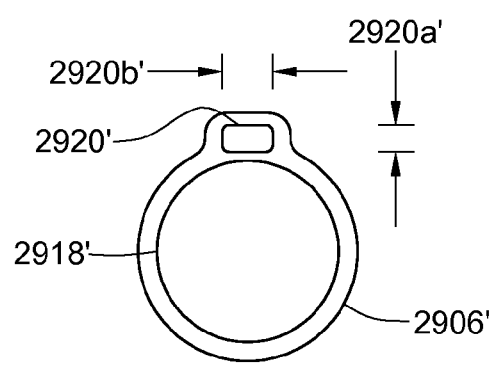

While illustrated in FIG. 29D as round in cross section, one or both of the first and second lumens may have other shapes. For example, FIG. 29E illustrates a cross section of an alternate member 2906' having a round first lumen 2918' and a second lumen 2920' that is rectangular or otherwise elongate in cross section. The rectangular cross section lumen 2920', when occupied by a stiffening member of matching shape (e.g., a nitinol wire or band of rectangular cross section), may reduce rotational deflection (as well as other forms of deflection) of the elongate members 2906 during deployment. For example, because of the lesser moment about the minor dimension 2920a' compared to the major dimension 2920b', the elongate members 2906' may preferentially bend outwardly during expansion, rather than laterally, e.g., towards an adjacent elongate member.

While FIGS. 29D and 29E illustrate the members 2906 as dual lumen tubing, the elongate members 2906 may also be made with a single lumen, such as polymer or other flexible tubing. The polymer tubing, while flexible enough to be deployed into a curved configuration, may also be sufficiently stiff so as not to require a secondary stiffening member. Such tubing may be fabricated from high durometer polymers, such as nylons, polyetheretherketones (PEEK), polyimides, and the like. Optionally the tubing cross section may be non-circular in cross section (e.g. trapezoidal, rectangular) to facilitate the proper orientation of bending during device expansion and also to increase lateral stability of the elements while in the expanded position. Additionally, the tubing may include reinforcing elements (e.g., flat wire braid, not shown) within its wall to provide enhanced torsional and flexural stiffness.

In further alternatives, the elongate members 2906 may include other features providing pathways extending between the proximal and distal ends 2906a, 2906b. For example, the elongate members may include grooves or tracks (not shown), which may receive one or more sources of radiation (also not shown), as described further below. The features may include any other interlocking features that restrict movement of one or more sources of radiation, e.g., to axial movement along the elongate members. Thus, as used herein, "pathway" may include a lumen, track, rail, or other feature on an elongate member configured for guiding one or more radiation sources along the elongate member.

Figure 29F:
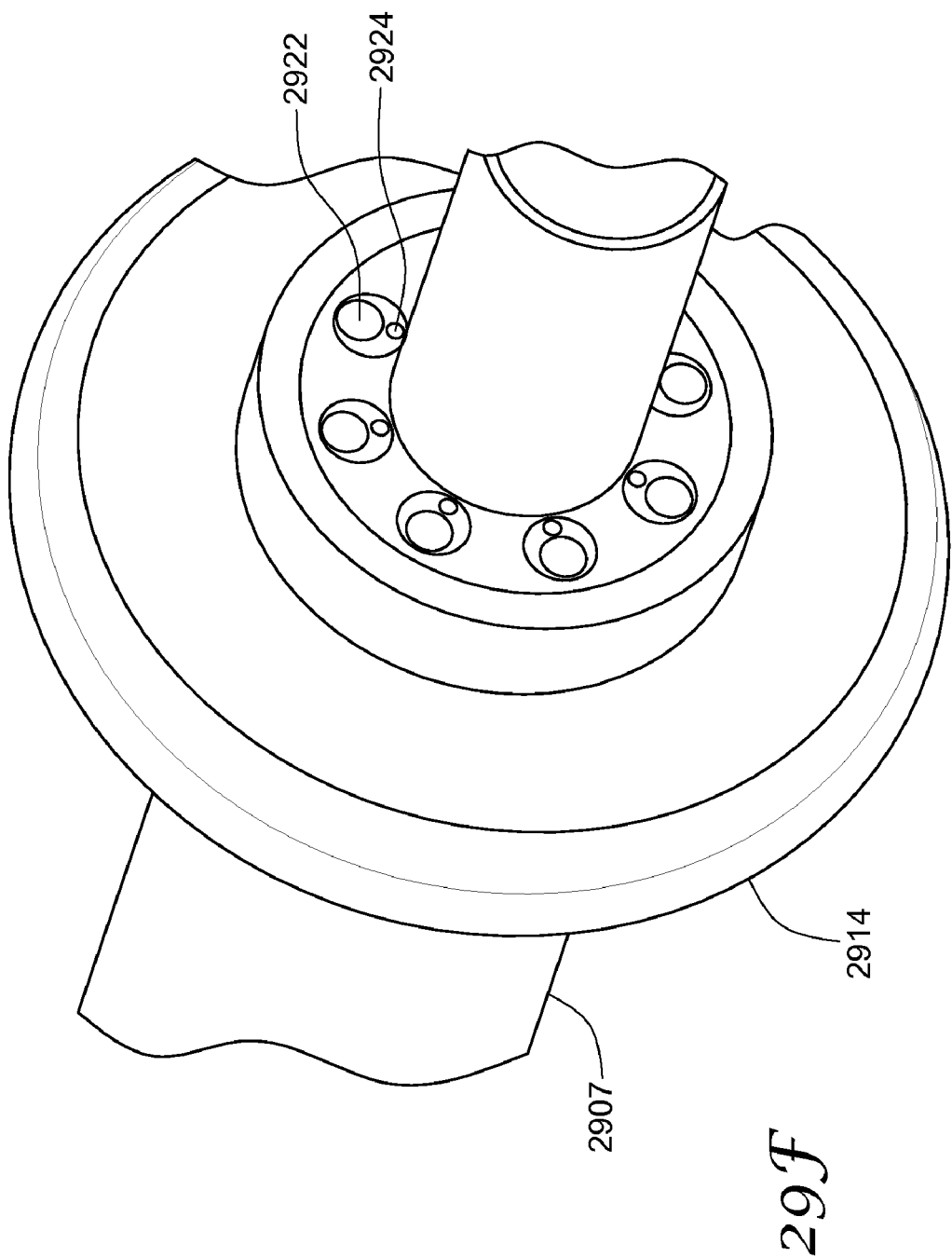

FIG. 29F illustrates a proximal side of the flange 2914 as it may be configured in one embodiment. The flange 2914 may include a series of openings 2922 and 2924 that provide access to the lumens 2918 and 2920 of the members 2906. For example, the opening 2922 may be coupled to the lumen 2918 (see FIG. 29D) in a respective elongate member 2906 via a respective lumen (not shown) extending through the body member 2907, while the opening 2924 may be coupled to the lumen 2920. As a result, a brachytherapy device and stiffening member (not shown) may be inserted into their respective lumens 2918 and 2920 either before or after the apparatus 2900 is implanted into a target location, as described elsewhere herein. Optionally, the flange 2914 may further include a locking member or ring (not shown) that may secure one or both of the brachytherapy devices and stiffening members relative to the flange 2914.

While not illustrated, the flange 2914 may include indicia (such as alphanumeric symbols, e.g., consecutive numbers like a clock) to identify the respective openings 2922/2924 around the circumference of the flange 2914. As a result, the physician/oncologist may know which opening 2922 is to receive a particular brachytherapy device in accordance with a desired dose plan, e.g., before or after introducing the apparatus 2900 into a target location. For example, the dose plan may call for a low activity device (device no. "1") to be placed in an area that is proximate the patient's skin. The corresponding opening 2922/2924 may include the same number (no. "1"), or otherwise identify it as the correct opening 2922/2924 to receive the particular low activity device. Thus, with the apparatus 2900 properly oriented within a target location (e.g., with the low activity pathway of elongate member "1" oriented towards the skin), the low activity device may be placed along the low activity pathway, which may reduce the risk of damaging the skin. Correspondingly, higher activity brachytherapy devices may be placed in other specified openings in accordance with the desired dose plan.

Dose planning may be accomplished with the aid of current imaging methods (e.g., CT or ultrasound) and with commercially available dose planning software for either HDR or LDR applications. The timing and general scenario of the dose planning process is at the discretion of the clinical physicist/oncologist. However, one such scenario may include placing the apparatus 2900 into the target tissue region and activating the elongate members 2906 into a deployed configuration. Then, with the aid of imaging (e.g., CT), both the target tissue region and the position of the elongate members 2906 may be delineated. A dose plan may then be developed and, if desired, modified as configuration adjustments are made to the apparatus 2900 and the elongate members 2906.

When the dose plan is optimized, the characteristics of the radioactive sources (e.g., brachytherapy devices) are chosen (e.g., LDR seed activity levels, HDR dwell positions, etc.), and prepared for placement into the apparatus 2900 via the access openings 2922/2924. For example, during LDR brachytherapy, individual pods or other radiation sources may be loaded into respective elongate members 2906 simultaneously or sequentially, thereby providing a three dimensional array of seeds or radiation sources that may remain in the target location for an extended period of time. The seeds may be spaced apart on each pod or have different radioactive intensities, according to the dose plan. For example, the seeds in different portions of the array may also have different lengths and/or spacing along respective elongate members 2906 such that the array is substantially asymmetrical, e.g., radially and/or axially relative to a central axis of the apparatus 2900. Alternatively, during HDR brachytherapy, an individual radiation source may be positioned sequentially along each pathway of the elongate members 2906 for specified exposure times. Optionally, more than one HDR radiation source may be directed along the pathways simultaneously.

While described herein as utilizing separate components, in other embodiments of the apparatus 2900, the elongate members 2906 may extend from the distal hub 2909 proximally all the way to the flange 2914. Thus, the elongate members 2906 may define one or more lumens extending from their respective distal ends 2906a to the flange 2914. The lumens may then receive a brachytherapy device (not shown) having its own stiffening member incorporated therein, see, e.g., device 1202 described elsewhere herein. Alternatively, the elongate members 2906 may already include stiffening members, e.g., within the lumens 2920 or otherwise secured along the elongate members 2906.

Optionally, the stiffening members may provide shielding, similar to other embodiments described elsewhere herein. For example, with generally spherical arrays or radioactive sources, a central region of the array tends to receive greater radioactive exposure than peripheral regions of the array. Shielding placed along inner regions of the elongate members 2906 may reduce overdosing in the central region. For example, FIGS. 32F and 32G show stiffening/attenuating members extending along inner regions of the elongate members 3106 for this purpose.

Figure 30A:
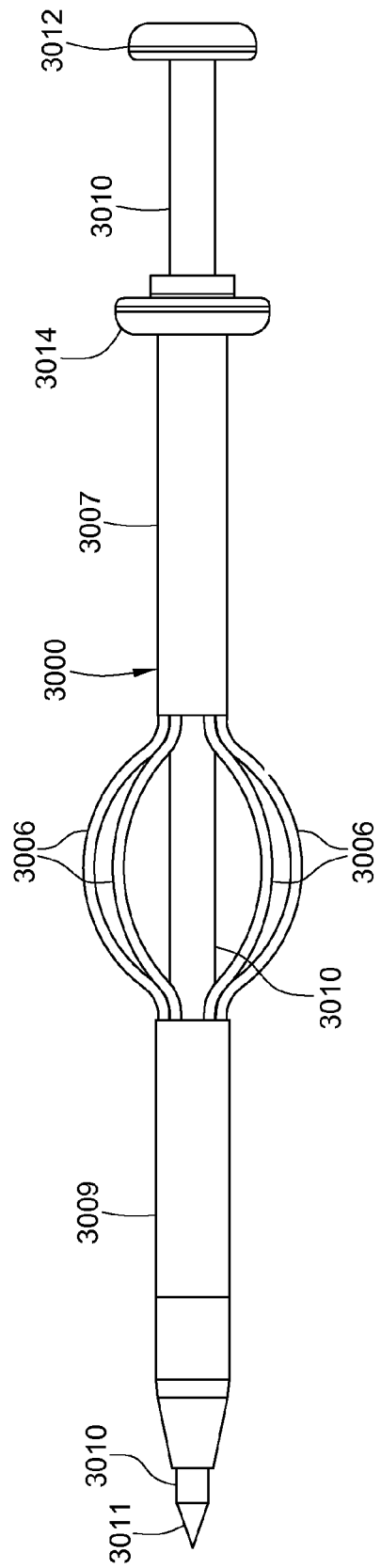
Figure 30B:
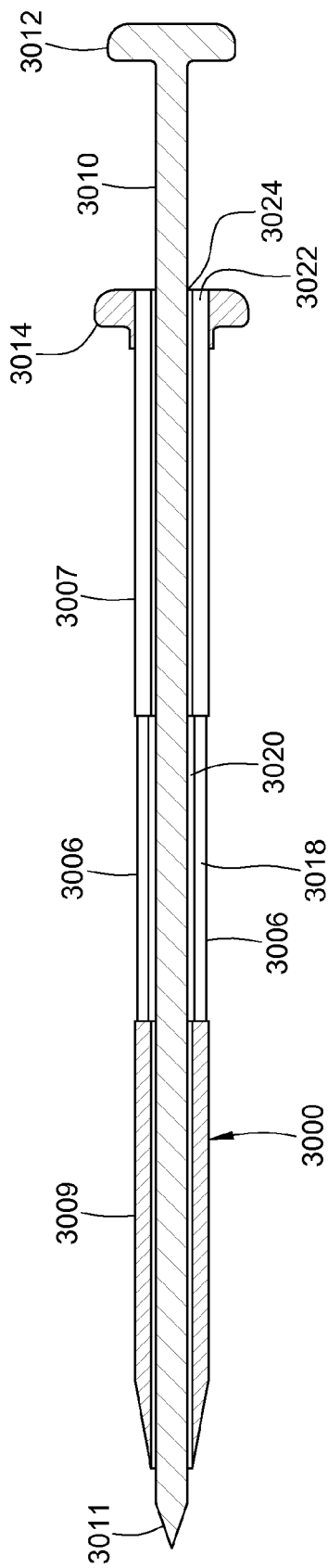
Figure 30C:
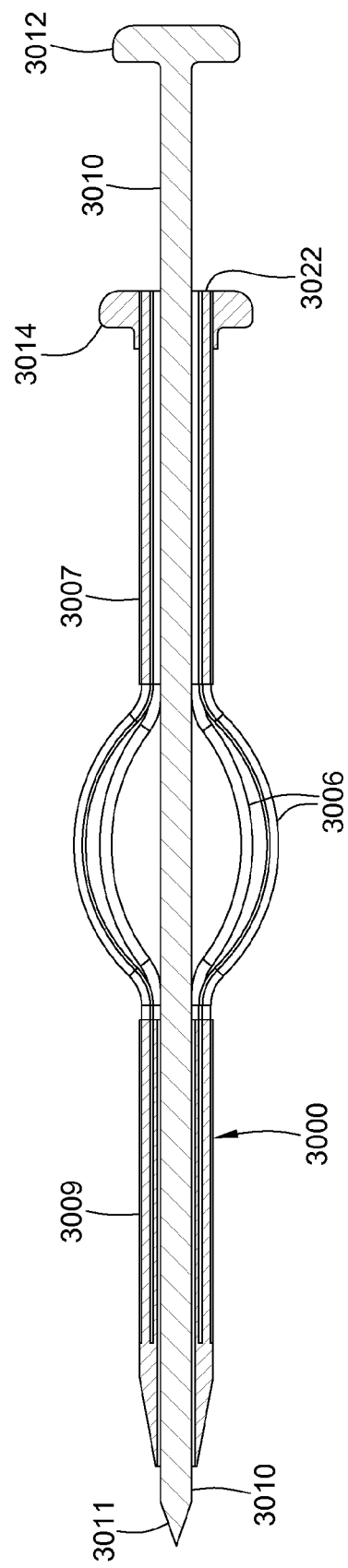

FIGS. 30A-30C illustrate a brachytherapy apparatus 3000 similar in many respects to the apparatus 2900 described above. The apparatus 3000 differs however, in that it is designed to penetrate entirely through a body or tissue structure, e.g., through a breast (not shown). As a result, a distal end of the apparatus 3000 is modified somewhat from the apparatus 2900 to accommodate this application.

FIG. 30A illustrates a side elevation view of the apparatus 3000. Like the apparatus 2900, the apparatus 3000 includes radioactive and flexible elongate members 3006 that are coupled at a proximal end 3006a to a body member 3007 and, at a distal end 3006b, to a hub 3009. A core member 3010, having a button 3012 at one end and a sharp distal tip 3011 at the other, may extend through the body member 3007 and the hub 3009. The sharp distal tip 3011 may permit penetration of tissue by the apparatus 3000 during implantation. Unlike the apparatus 2900, the core member 3010 is not permanently fixed to the hub 3009. Rather, it may slide relative to the hub 3009 and the body member 3007. Optionally, the core member 3010, body member 3007, and/or hub 3009 may include one or more connectors (not shown) for releasably securing the core member 3010, e.g., during implantation, but allowing the core member 3010 to be removed after implantation.

FIG. 30B illustrates a cross-sectional view of the apparatus 3000 in a first collapsed configuration. As illustrated in this view, the elongate members 3006 include lumens 3018, 3020 (e.g., similar to lumens 2918 and 2920 illustrated in FIG. 29D) that either extend through the body member 3007, or that communicate with separate lumens 3022 and 3024 that extend through the body member 3007. As a result, brachytherapy devices, e.g., device 102, 152, 402, 502, and 602 described above, may be threaded into the elongate members 3006 either before or after implantation of the apparatus 3000.

FIG. 30C illustrates a cross-sectional view of the apparatus 3000 in the second expanded configuration. This configuration is achieved by displacing the hub 3009 and body member 3007 towards one another, e.g., using an actuator, such as the button 3012 and flange 3014, or other embodiments described herein.

In use, while in the collapsed configuration shown in FIG. 30B, the apparatus 3000 may be inserted into the body, e.g., breast or other tissue structure (not shown), until the elongate members 3006 are disposed within a cavity or other target location (also not shown). The apparatus 3000 may be inserted until the hub 3009 extends out the opposite (distal) side of the breast. The sharp tip 3011 of the core member 3010 may be used to penetrate tissue on either side of the cavity during implantation. Optionally, once the apparatus 3000 is passed entirely through the breast, the core member 3010 may be removed from the apparatus 3000, e.g., by pulling the core member 3010 out the proximal end of the apparatus 3000. At this point, the physician may grasp the body member 3007 and the hub 3009 and push the two components 3007, 3009 towards one another. As this occurs, the elongate members 3006 expand radially outwardly towards the cavity walls, e.g., towards the expanded configuration illustrated in FIG. 30C.

When fully deployed, the body member 3007 and the hub 3009 may be secured to the body, e.g., to the skin, with tape, sutures, or the like. Alternatively, a locking member (not shown) may be inserted through the body member 3007 and/or the hub 3009 that holds the two components relative to one another (e.g., a long plastic threaded bolt with nut, not shown). In another alternative, movement of the body member 3007 and/or hub 3009 may be limited, e.g., using ratchets, detents, and the like (not shown) that may fix the body member 3007 and hub 3009 relative to one another, but may be overcome to move the body member 3007 and/or hub 3009, as described elsewhere herein.

The brachytherapy devices (not shown) may be carried by the elongate members 3006 when the apparatus 3000 is introduced or the apparatus 3000 may be introduced without the brachytherapy devices. If the brachytherapy devices are not included in the apparatus 3000 at implantation, a radiation oncologist or similarly trained clinician may then insert the brachytherapy devices through the lumens 3022 or other pathways along the elongate members 3006. Alternatively, automated systems may be provided for delivering one or more radiation sources along the pathways. In other embodiments, the brachytherapy devices may be preloaded into the apparatus 3000 before implantation, either removably or permanently carried by the elongate members 3006.

FIGS. 31A-31F illustrate an in-situ actuatable brachytherapy treatment apparatus 3100 in accordance with yet another embodiment. The apparatus 3100 includes a series of radioactive and elongate flexible members 3106, that are deployable from a first collapsed, e.g., straight, configuration (shown in FIG. 31A), to a second deployed e.g., curvilinear, configuration (shown in FIG. 31B). In the collapsed configuration, the members 3106 may be collapsed against the apparatus 3100 (e.g., are generally parallel to a central longitudinal axis of the apparatus 3100), e.g., to minimize size for implantation. However, in the deployed configuration shown in FIG. 31B, at least a portion of the elongate members 3106 expand radially towards and/or into the outer walls of a body cavity, e.g., a lumpectomy cavity (see, e.g., FIGS. 32D-32G). As a result, the apparatus 3100 is generally fixed within the tissue surrounding the cavity.

In the illustrated embodiment, the elongate members 3106 may be configured in two distinct groups best viewed in FIG. 31B. The first or outer group includes elongate members identified by reference numeral 3106a and forms a football or watermelon-shaped boundary, as shown in FIG. 31B. The second or inner group includes elongate members identified by reference numeral 3106b and defines a similar, but smaller, watermelon shape. In the illustrated embodiment, the outer group includes seven separate members 3106a, while the inner group includes three separate members 3106b. However, other embodiments may vary the number of elongate members 3106 in either group. The elongate members 3106a and 3106b may be referred to generically, or collectively, as elongate members 3106.

The elongate members 3106 may be attached at a first (e.g., proximal) end to a body member 3107. However, the elongate members 3106a may be attached at their respective second (e.g., distal) ends to a distal hub 3109, while the distal ends of the members 3106b may be attached to a separate floating hub 3108.

The apparatus 3100 may further include a core member 3110 that is attached to the distal hub 3109 and extends out the proximal side of the body member 3107. The core member 3110 may be fixed to the distal hub 3109, yet pass with clearance through openings in both the body member 3107 and the floating hub 3108. As a result, the body member 3107 and the floating hub 3108 may slide along the core member 3110, as further described below. The core member 3110 may function as a tension member. As a result, it may be generally rigid or, alternatively, a tension-only member such as a cable or a suture.

Each of the elongate members 3106 may include a stiffening member, which in the illustrated embodiments, is an elastic flat wire 3112. The wire 3112 ensures that the elongate members 3106 expand and contract in the desired orientation (e.g., without twisting). The wire 3112 may also provide some integrity to the elongate members 3106, e.g., to ensure that the elongate members 3106 may be forced outwardly into the cavity walls with sufficient radial and lateral stability. While not wishing to be bound to any particular material, the wires 3112 may, in one embodiment, be made from tempered stainless steel or a shaped memory alloy such as nitinol or the like. Such materials may permit the apparatus 3100 to invaginate the lumpectomy walls and/or remain in a substantially secure geometry (see FIGS. 32D-32G), while also permitting collapse of the apparatus 3100 to its pre-deployed configuration at therapy completion.

Individual tubes 3114 may be attached to respective flat wires 3112. The tubes 3114 are operable to receive a brachytherapy device (not shown), as already described herein, e.g., devices similar to devices 102, 152, 402, 502. Alternatively, the tubes 3114 may be made to receive individual radioactive sources, e.g., seeds 108 described elsewhere herein, and spacers, which may be loaded into the tubes 3114 during or before a treatment. Thus, the tubes 3114 may form the outer surface of the actual brachytherapy devices. The tubes 3114 may be made from most any biocompatible material that is capable of retaining the radioactive sources or a pre-assembled brachytherapy device, e.g., fluoropolymers, such as fluorinated ethylene-propylene (FEP), nylon, and polyurethane.

Figure 31A:
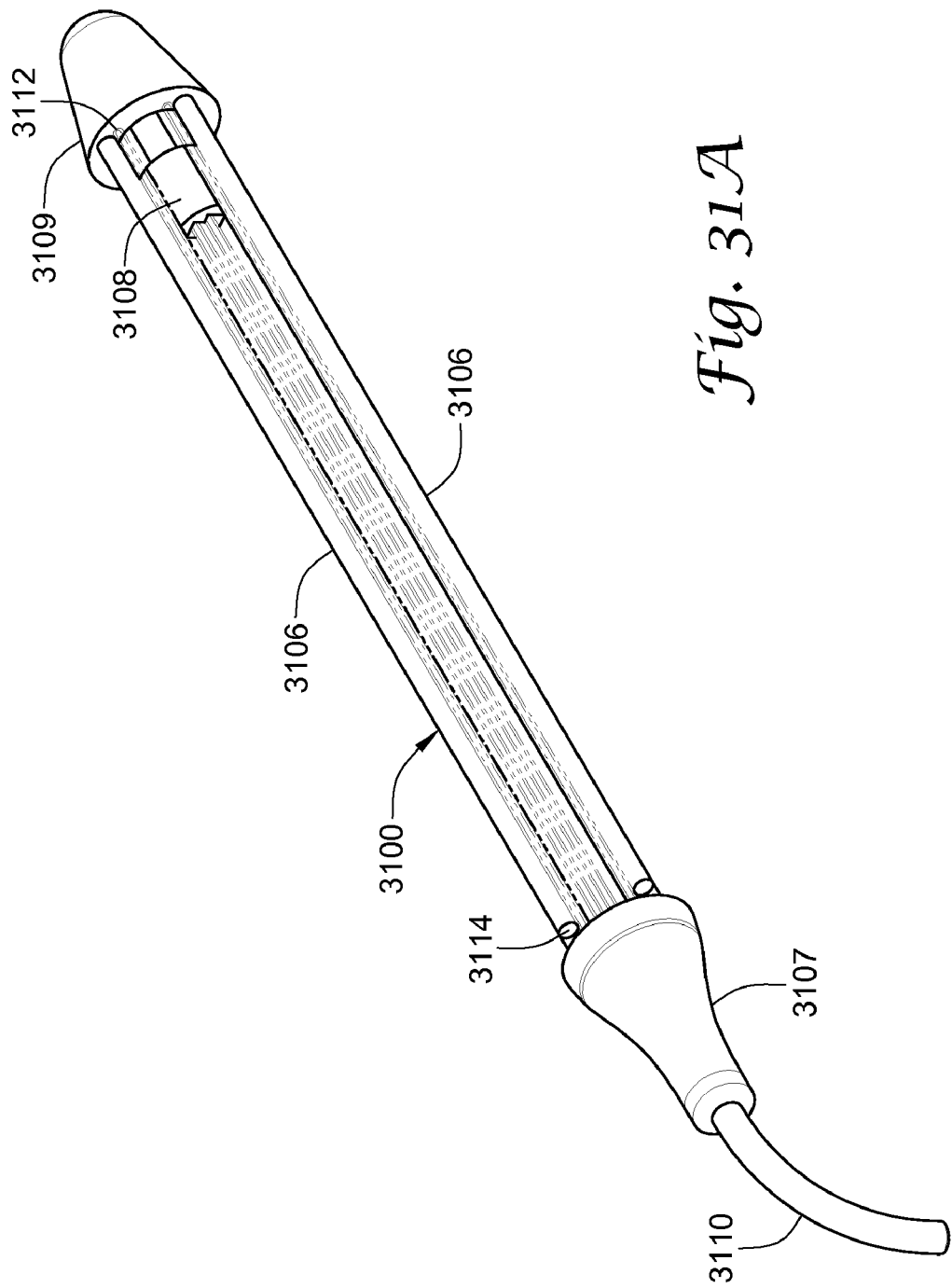
Figure 31C:
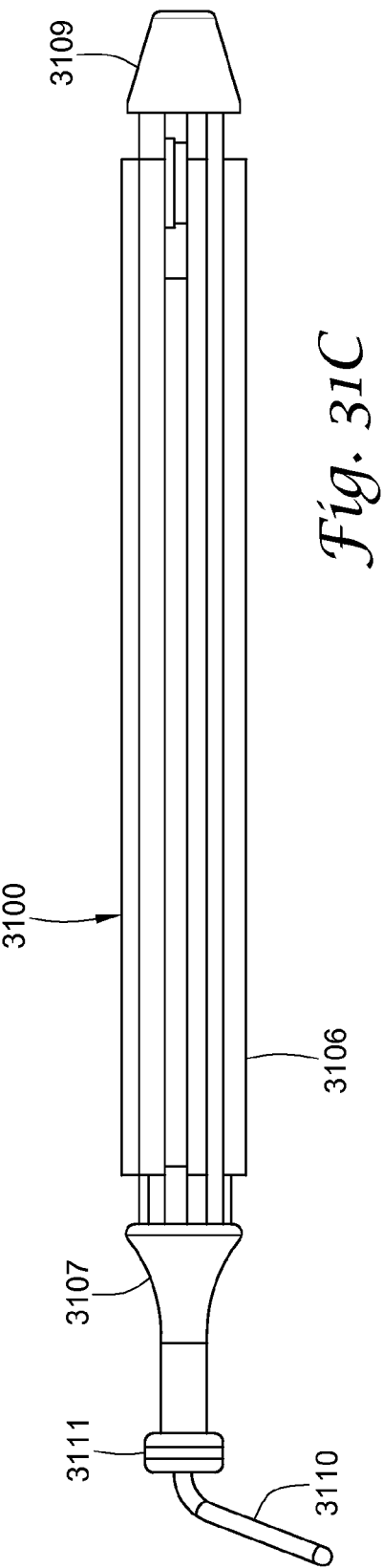
Figure 31D:
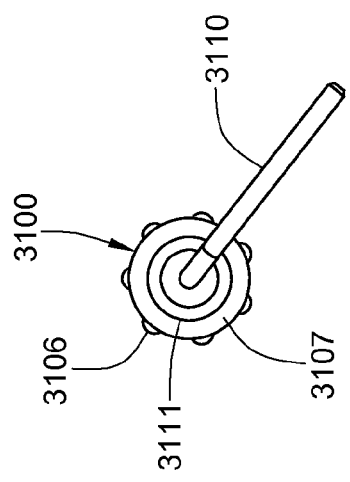

FIG. 31C illustrates a side elevation view of the apparatus 3100, while FIG. 31D illustrates an end view. These two views illustrate a variation of the body member 3107 that includes a flange 3111 formed thereon or attached thereto. This optional flange 3111 may be beneficial to the physician during the implantation and/or removal process, by providing a location to be gripped during positioning of the core member 3110.

Figure 31E:
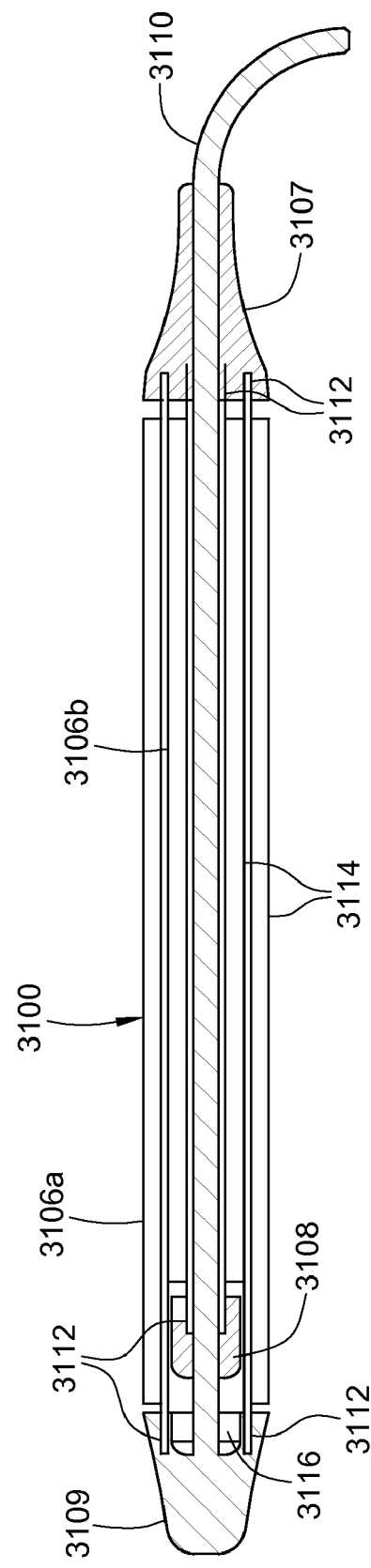

FIG. 31E is a staggered longitudinal cross-sectional view of the apparatus 3100 in the collapsed configuration (by staggering the cross-section, this figure illustrates sections of two elongate members 3106a and two elongate members 3106b that would not otherwise appear in a straight cross-section). In this view, the attachment of the core member 3110 to the distal hub 3109 is clearly shown, as is the fixation of the flat wires 3112 with the distal hub 3109, the floating hub 3108, and the body member 3107.

FIG. 31E further illustrates a pocket 3116 formed within the distal hub 3109. The pocket 3116 provides a stop surface that limits axial movement of the floating hub 3108 when the apparatus 3100 is in the deployed configuration. While illustrated as a pocket 3116, another embodiment could be configured to have the floating hub 3108 merely contact a flat inside face of the distal hub 3109.

FIG. 31F is a staggered longitudinal cross-sectional view, similar to FIG. 31E, with the apparatus 3100 in the deployed configuration. As shown in this view, the deployed configuration may be achieved by applying a tensile force to the tail portion of the core member 3110 while holding the body member 3107 in place. Applying such a tensile force causes the distal hub 3109 to move towards the body member 3107. As this movement occurs, the elongate members 3106a begin to bow outwardly as illustrated. Once the floating hub 3108 contacts the pocket 3116, the members 3106b also begin to bow outwardly. Further tensioning of the core member 3110 may result in outward movement of both the elongate members 3106a and 3106b. By changing the axial position of the core member 3110 relative to the body member 3107, a variety of deployed diameters are possible. When the apparatus 3100 is deployed to the desired diameter, a clamp or similar device (not shown) may be crimped around the core member 3110 immediately adjacent the body member 3107 to prevent the core member 3110 from sliding relative to the body member 3107.

Other methods for securing the apparatus 3100 in the desired diameter may include a threaded nut and bolt assembly (not shown). For example, the body member 3107 may be split and externally threaded like a conventional machinist's collet (not shown). A nut (not shown) may be threaded around the collet and tightened to hold the core member 3110, thereby holding the apparatus 3100 at the desired degree of expansion. Alternatively, the core member 3110 may include a series of closely spaced holes or pockets (not shown) residing along the region where the core member 3110 protrudes from body member 3107. A cotterpin or the like (not shown) may be placed at the desired hole or pocket to hold the apparatus 3100 with the desired degree of expansion.

Figure 32A:
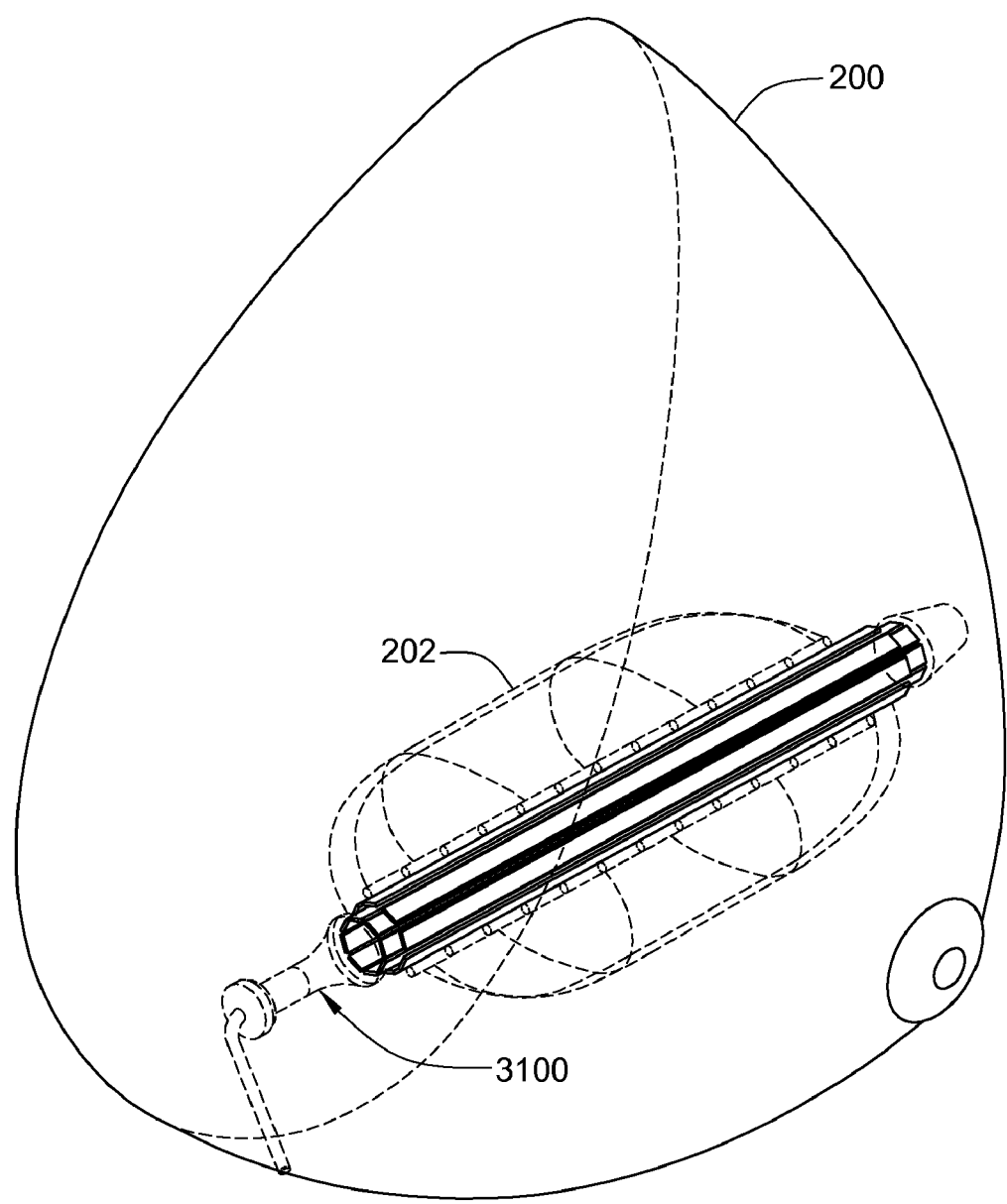
Figure 32B:
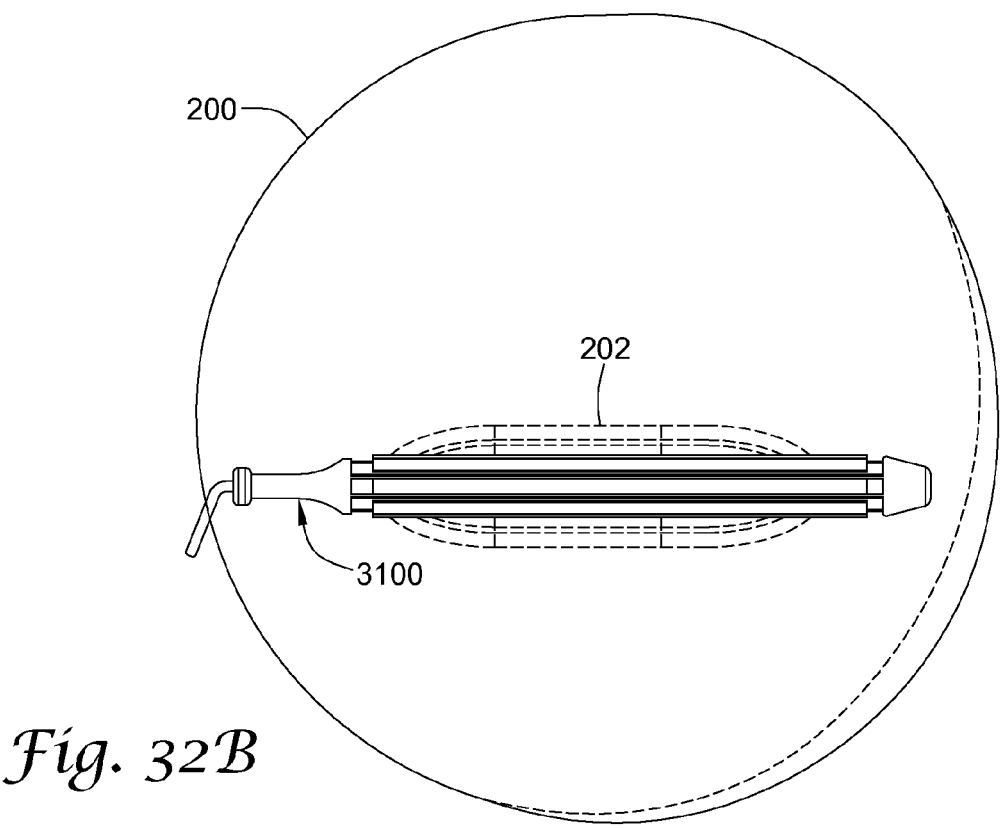
Figure 32C:
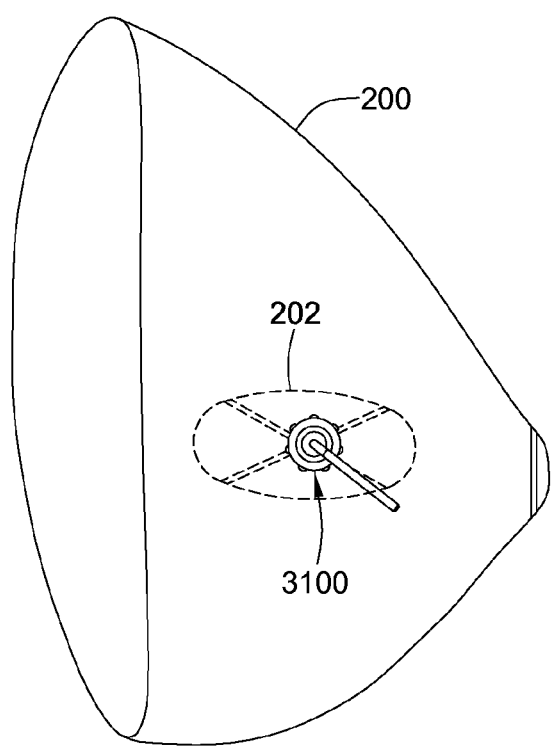
Figure 32D:
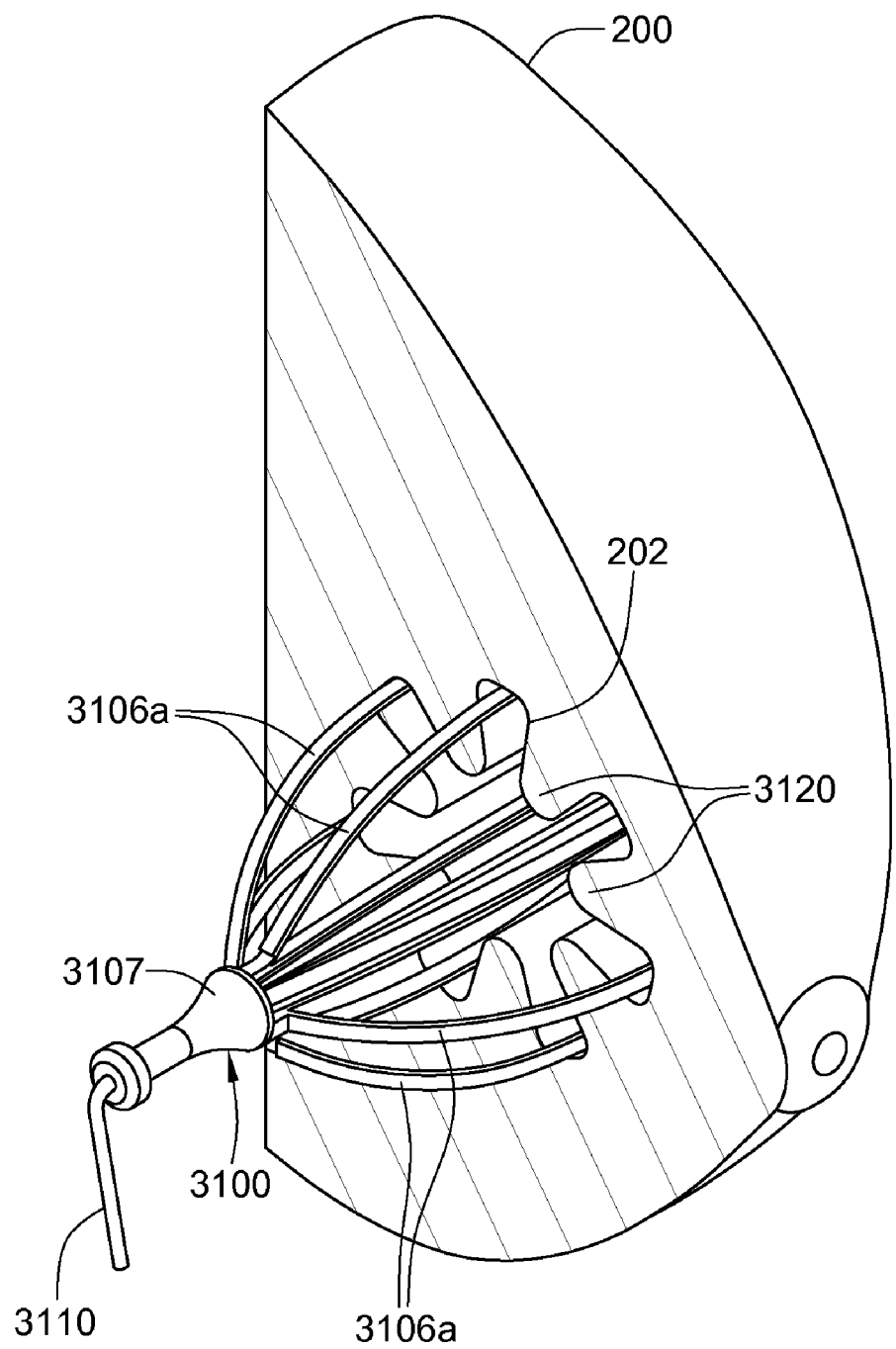
Figure 32E:
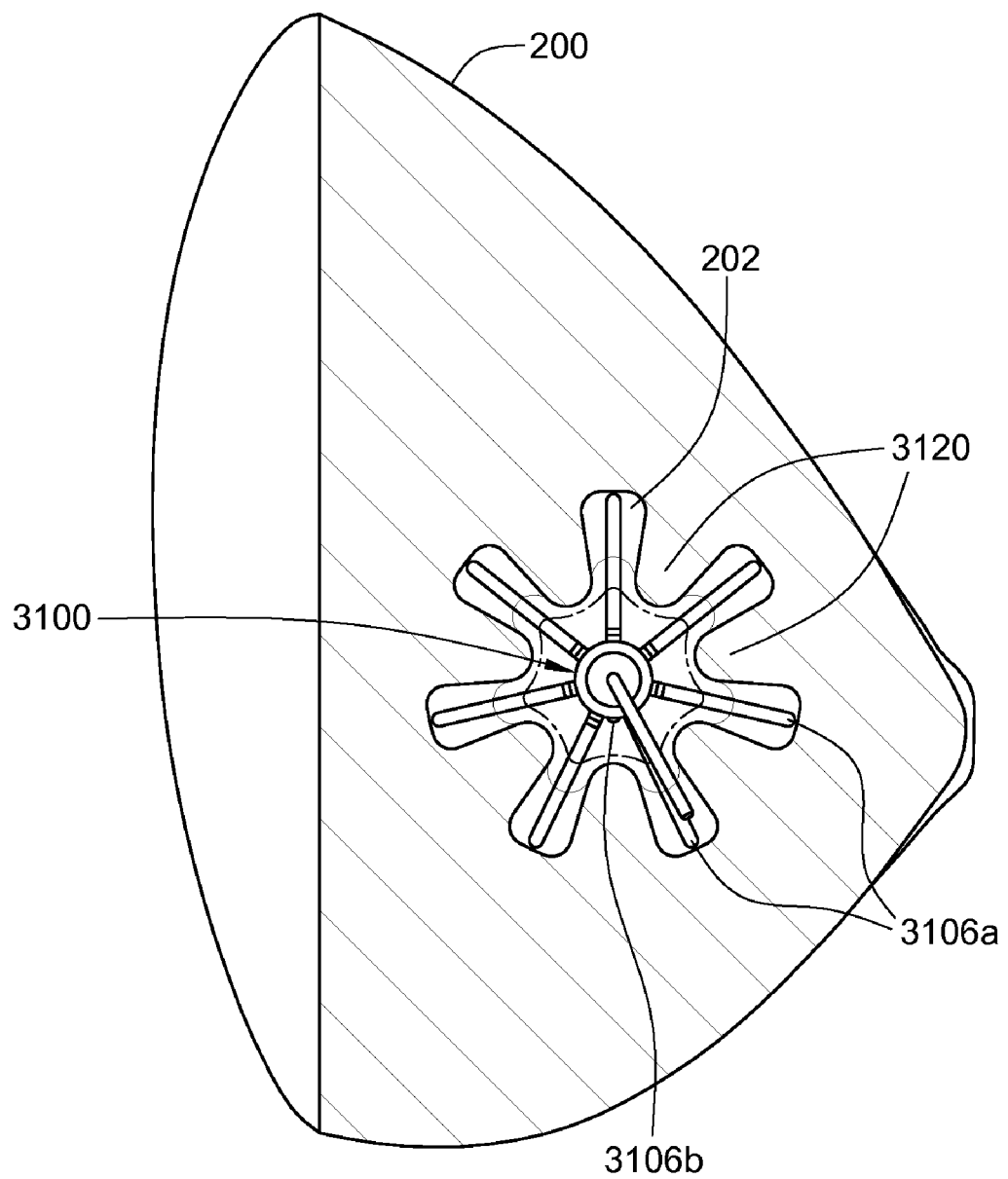
Figure 32F:
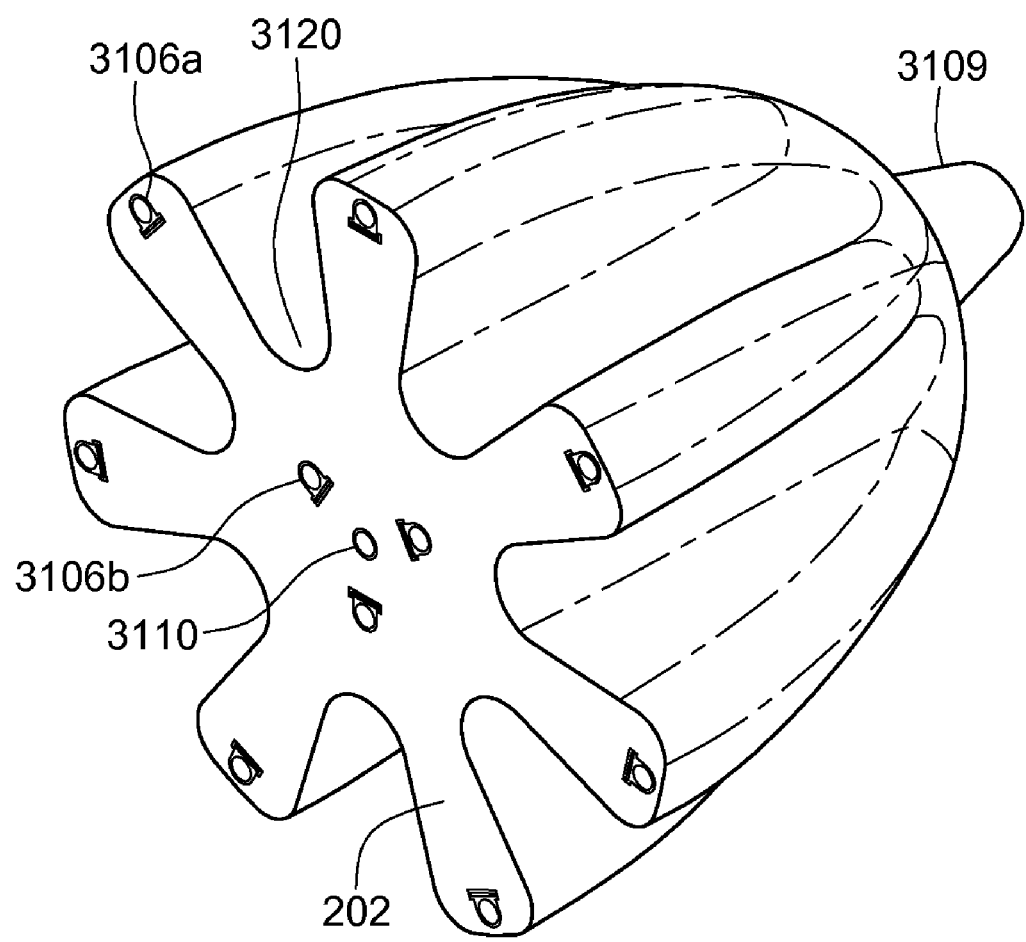
Figure 32G:
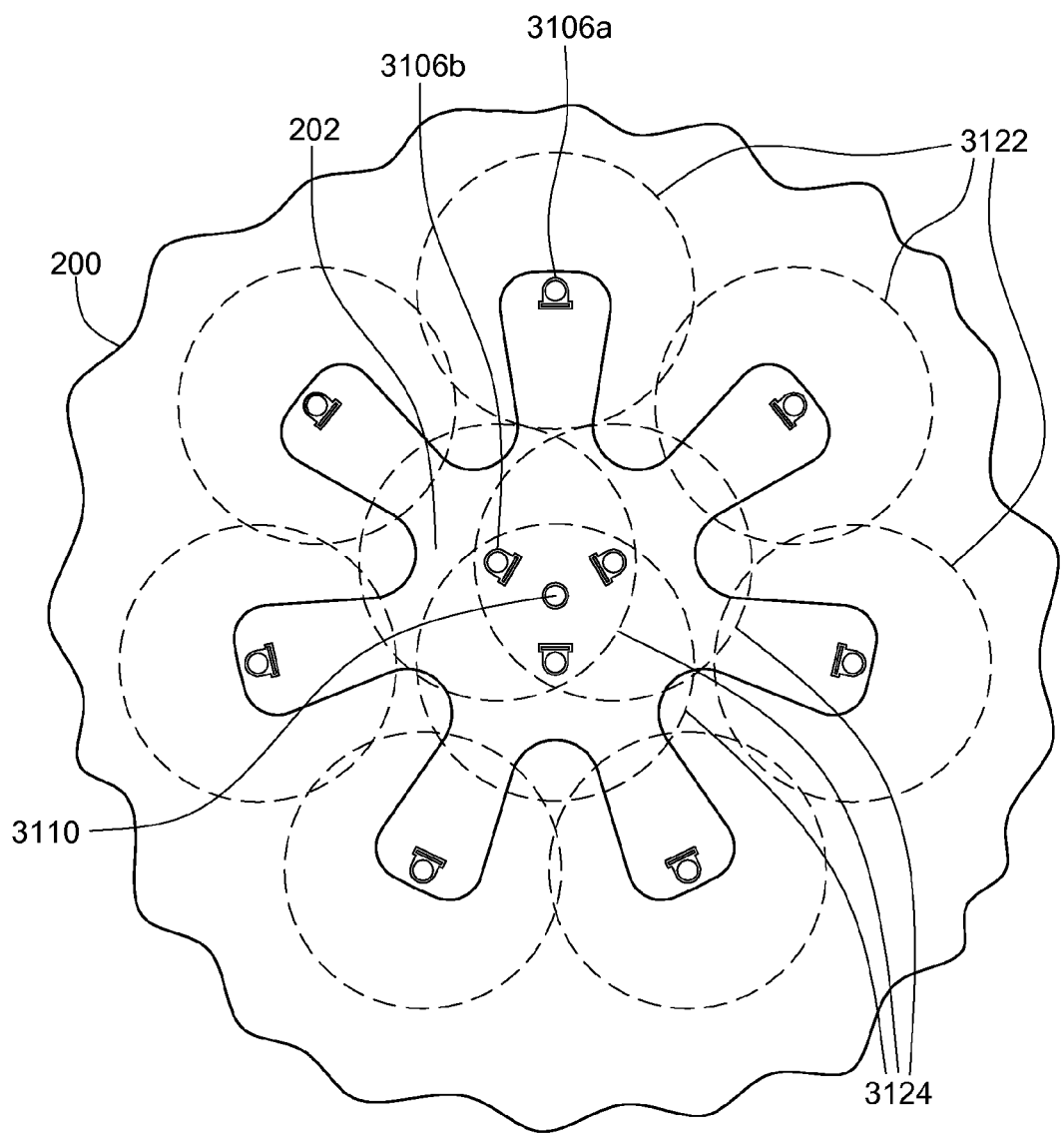

FIGS. 32A-32F illustrate a method for using the apparatus 3100 of FIGS. 31A-31F. FIG. 32A illustrates a perspective view of a portion of a body (e.g., a breast 200) having a cavity (e.g., a lumpectomy cavity 202) formed therein by removal of cancerous tissue. The apparatus 3100 is shown inserted and in its collapsed position. The apparatus 3100 may be inserted via an existing incision, e.g., the incision used to perform the lumpectomy, or via a new incision created for delivering the apparatus 3100. FIGS. 32B and 32C illustrate a front and side view of the breast 200, respectively, with the collapsed apparatus 3100 shown in place within the cavity 202.

Once the apparatus 3100 is in the desired position, the core member 3110 may be pulled by the physician while the body member 3107 is held against the breast incision. The length of the body member 3107 may be sufficient to extend to the skin surface, regardless of the distance from the skin to the lumpectomy cavity 202. As the apparatus 3100 deploys, it may tend to center itself within the cavity 202, e.g., as shown in FIGS. 32D-32F.

Figure 32H:
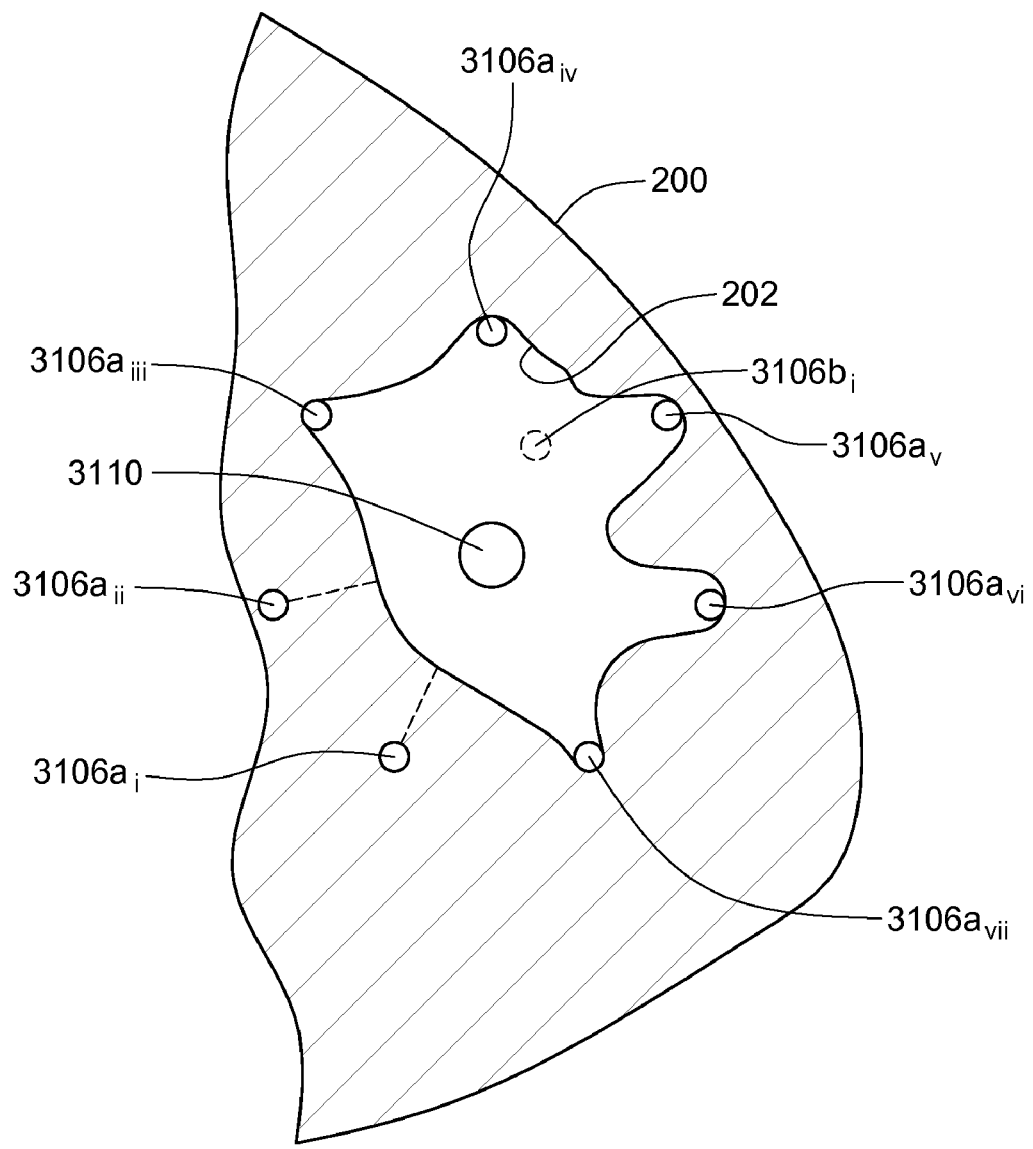
FIG. 32H is a cross-sectional view of an apparatus deployed within a lumpectomy cavity within a tissue structure, showing penetration of elongate members of the apparatus into surrounding tissue.

Alternatively, the apparatus 3100 may also move within the cavity during expansion of the apparatus 3100 due to varying amounts of penetration of the elongate members within the adjacent tissue. For example, as shown in FIG. 32H, the region adjacent the skin is less prone to penetration by the elongate members 3106 than the tissue underlying the cavity 202. As shown in FIG. 32H, the elongate members 3106 may be sufficiently small such that at least some of the elongate members (e.g., elongate members $3106_i$, $3106_{ii}$) may cut, tear, or otherwise penetrate through tissue surrounding the cavity 202, thereby allowing radiation to be delivered deeper into tissue than if there was no penetration of the elongate members 3106 into the adjacent tissue. This ability of the elongate members 316 to penetrate the tissue and, in some cases be circumferentially surrounded by adjacent tissue (e.g., as shown in FIG. 32H), effectively provides an interstitial form of radionuclide placement for the apparatus 3100.

FIG. 32D illustrates a perspective cross section of the breast 200 and cavity 202 with the apparatus 3100 shown in its full expanded configuration therein. As illustrated in this view, the elongate members 3106a may push beyond the walls of the cavity 202, resulting in invagination of the tissue around the members 3106a, e.g., portions of wall tissue 3120 may flow, extrude, or extend inwardly between the elongate members 3106a to substantially surround the elongate members. In one embodiment, the wall tissue 3120 may extend radially inwardly about 0.7 centimeter from the outermost elongate members 3106a. However, actual invagination distances may vary based on several variables, including, for example, apparatus size and shape, cavity size and shape, and tissue properties. The elongate members 3106b preferably remain within the diameter defined by the innermost portions of the extruded wall tissue 3120. As can be appreciated from this view, invagination results in substantial fixation of the apparatus 3100 relative to the surrounding tissue, and may distort the cavity 202 until it generally conforms to the shape of the apparatus 3100.

In one embodiment, a vacuum system (not shown) may be coupled to the apparatus 3100. The vacuum system may apply a vacuum pressure to the cavity 202 to increase the degree of tissue invagination. Such a vacuum may be left active during all or part of the implantation period, or may be disconnected immediately following treatment, e.g., for HDR therapy.

In still other embodiments, the elongate members 3106a may be conductive or otherwise excitable, such as by radio frequency (RF). Such activation of the elongate members 3106a after deployment may allow the elongate members 3106a to cut into the cavity walls, and therefore penetrate deeper into the surrounding tissue, which may further increase the degree of invagination.

FIG. 32E illustrates a section view of the apparatus 3100 implanted and fully deployed. The inwardly extending wall tissue 3120 is clearly visible in this view. FIG. 32F illustrates a partial perspective section view of the cavity 202 with diagrammatic representations of the elongate members 3106 shown therein in their deployed configuration.

FIG. 32G illustrates a cross-sectional view of the cavity 202 with the apparatus 3100 in its deployed configuration (and with some structure of the apparatus 3100 removed for clarity). This view further illustrates exemplary dose clouds provided by the brachytherapy devices contained within the elongate members 3106. For example, each of the elongate members 3106a may yield a dose cloud generally represented by circles 3122, while each of the elongate members 3106b may yield a simplified dose cloud generally represented by circles 3124. The circles 3122 and 3124 represent the effective two-dimensional cloud boundaries at a particular cross section, i.e., the dose clouds may create two layers of radiation, an outer layer around elongate members 3106a and an inner layer around elongate members 3106b. The actual cloud produced by each of the elongate members 3106 would be generally in the form of a curvilinear cylinder.

The three-dimensional cumulative effect of all the radiation sources in each of the two layers of elongate members 3106 is a therapeutic dose cloud shell that extends over the volume of tissue that immediately surrounds the cavity 202. With proper dose mapping and dose selection, the three-dimensional dose cloud shell may typically expose an adequate margin of tissue (e.g., one centimeter (1 cm) or more beyond the wall of the cavity 202) to the proper therapeutic dose. Because of the interstitial nature of many of the radionuclide sources, a therapeutic dose may be delivered to the desired region of tissue with lower risk of overdose effects that might be obtained if all the radionuclide sources resided within or at the edge of the cavity 202 (e.g., as may occur with a balloon applicator or other intracavitary applicator).

In addition, unlike a balloon applicator, individual elongate members 3106 may apply local discrete radial forces to surrounding tissue. A balloon applicator has a continuous surface and, consequently, applies a relatively continuous radial force along its surface to the adjacent cavity surface. In contrast, because the elongate members 3106 are intermittently spaced with voids therebetween, each elongate member 3106 may apply highly localized radial forces against the cavity surface, leading to invagination of tissue within the elongate members during expansion.

Turning to FIG. 32H, in some applications, one or more of the elongate members $3106a_{iv}$, $3106a_v$ may be located towards a relatively thin region of tissue adjacent the cavity 202, e.g., adjacent the patient's skin. If pods or other radiation sources having uniform radiation intensities are introduced into each of the elongate members 3106, there is a risk of overexposing or "burning" such thin tissue regions or the skin itself. For this reason, a dose plan may recommend introducing a radiation source into the elongate members $3106a_{iv}$, $3106a_v$ that has a relatively lower radiation intensity, or may even have one or more seeds "turned off" (i.e., by providing nonradioactive spacers between sources along at least a portion of one or both of the elongate members $3106a_{iv}$, $3106a_v$).

Optionally, the dose plan may recommend delivering radiation to the thin region from an inner layer of elongate members. For example, as shown in FIG. 32H, a single elongate member $3106b_i$ may be provided that is disposed between the elongate members $3106a_{iv}$, $3106a_v$ and closer to the central axis of the core member 3110. A radiation source may be introduced into the single elongate member $3106b_i$ to deliver radiation past the elongate members $3106a_{iv}$, $3106a_v$ and into the thin region of tissue. Thus, an inner layer of elongate members may be provided to enhance delivering radiation locally according to a desired dose plan.

In the embodiment illustrated in FIGS. 32D-32H, the elongate members 3106a may be configured to be spaced about one centimeter (1 cm) from each other (when fully expanded) at their largest diameter (which may be up to about three centimeters (3 cm)). Moreover, the radioactive sources, e.g., seeds 108 as described elsewhere herein, may yield a therapeutic dose cloud (circle 3122 and 3124) about the wires of approximately one centimeter (1 cm). As a result, the apparatus 3100 may provide radiation to all, or substantially all, of the cavity wall and surrounding tissue as represented by the circles 3122 and 3124 in FIG. 32G. It is noted that the radiation sources used with the apparatus 3100 may be low dose rate sources or, alternatively, high dose rate sources (such as Iridium or Ytterbium) that are delivered intermittently.

At the completion of brachytherapy treatment, the apparatus 3100 may be returned to its collapsed configuration, and the apparatus 3100 removed from the breast 200 via the insertion incision.

FIGS. 33A-33G illustrate an intracavitary brachytherapy apparatus 3600 in accordance with still yet another embodiment. The apparatus 3600 may include a brachytherapy device 3602 having a therapy delivery portion 3604 and external, e.g., tail, portions 3606.

Figure 33A:
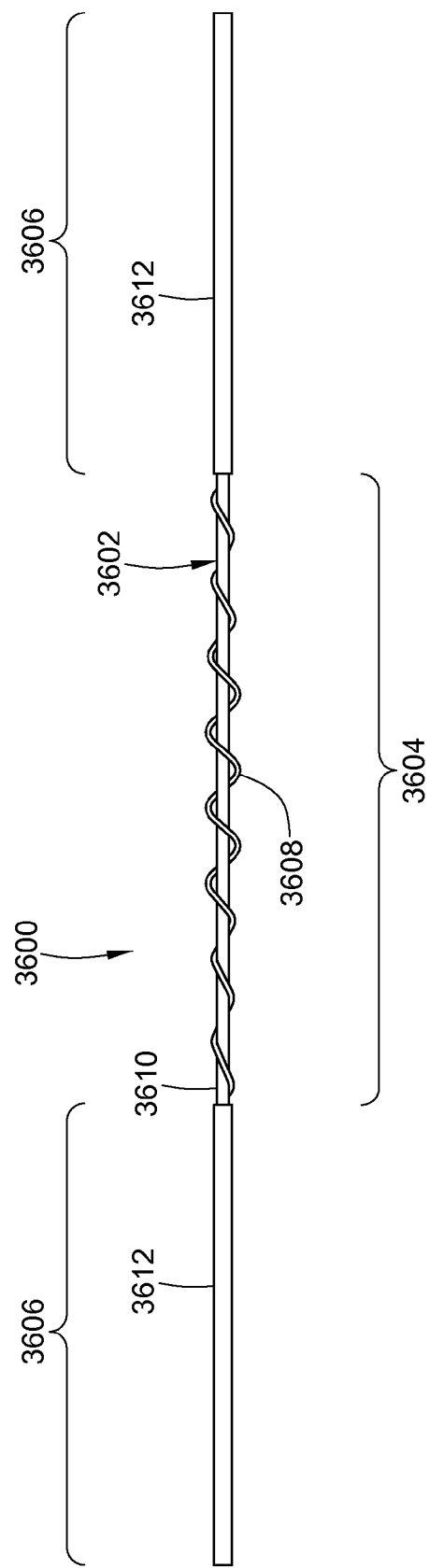
Figure 33B:
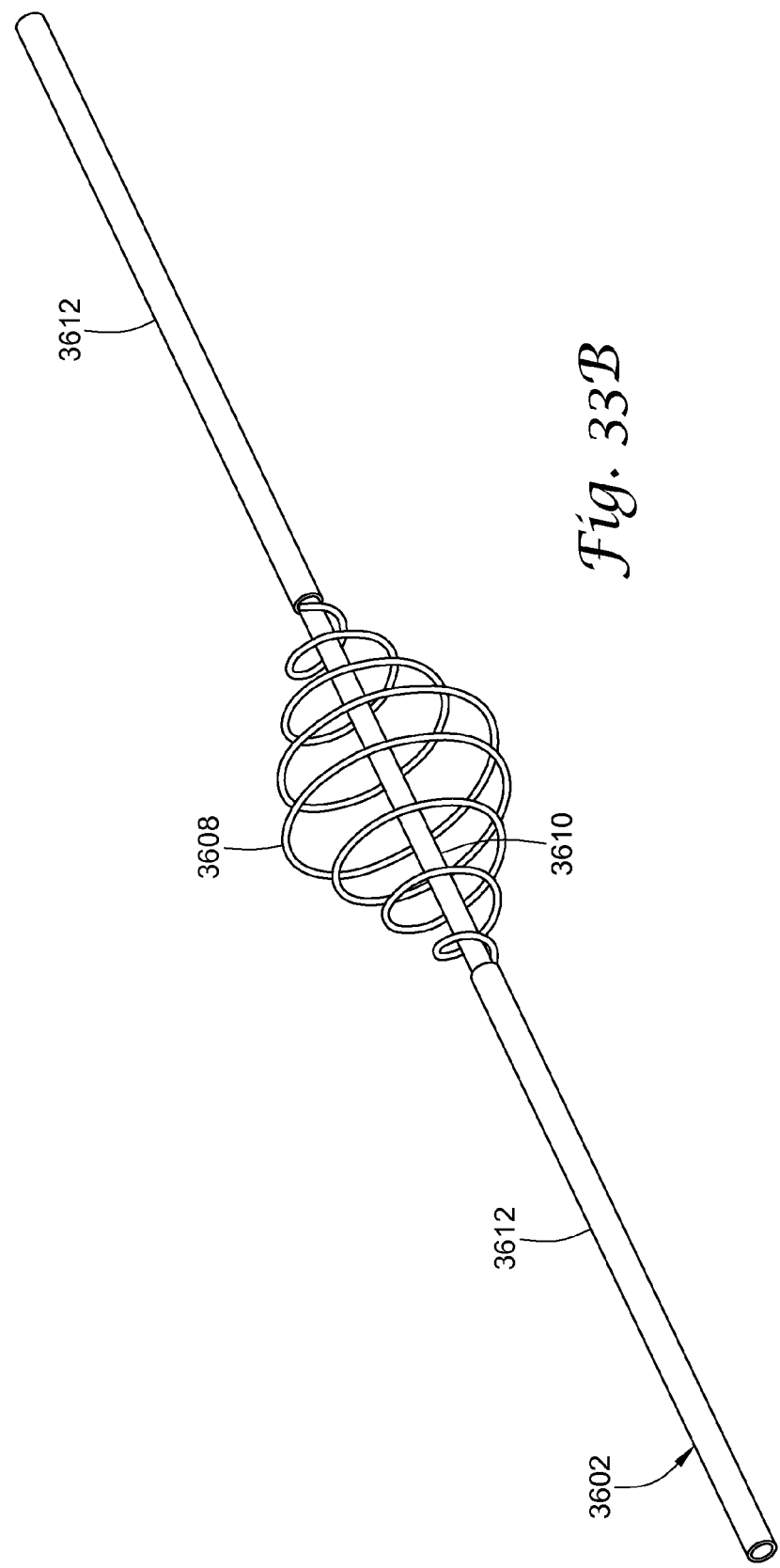

As FIG. 33A illustrates, the therapy delivery portion 3604 may be formed by a deformable and elongate radioactive source, e.g., coil member 3608. The coil member 3608 may form a helical coil wound about an elongate core member 3610. At least one end of the coil member 3608 (e.g., a proximal end) may be secured to an attachment member (e.g., a sleeve 3612) that translates and/or rotates about the core member 3610. This configuration provides a low profile device that may be inserted into a target region, e.g., lumpectomy cavity (not shown), via a relatively small incision. Once in place, however, the coil member 3608 may be deployed to form a spiral pathway within the cavity as shown in FIG. 33B. To deploy the device 3602, the sleeves 3612, which may extend outside of the body after implantation, may be rotated about the core member 3608 relative to one another. Relative rotation of the sleeves in one direction may cause the coil member 3608 to expand, i.e., move away, from the central core member 3610. Relative rotation of the sleeves 3612 in the opposite direction may similarly cause the coil member 3608 to contract around the core member 3610. The greater the expansile rotation, the more radial force may be exerted against the walls of the lumpectomy cavity. Greater force exerted against the walls of the lumpectomy cavity may result in a higher degree of invagination of the breast tissue within the turns of the expanded coil member 3608.

In addition to rotational movement of the sleeves 3612, the sleeves may also translate axially relative to the core member 3610. Axial translation permits adjustment in length of the coil member 3608 when in its expanded configuration. Due to the ability to independently control the axial length and the diameter (and hence the expansile force against the cavity walls) of the coil member 3608, the apparatus 3600 may be utilized to treat a variety of sizes and shapes of lumpectomy cavities.

Figure 33C:
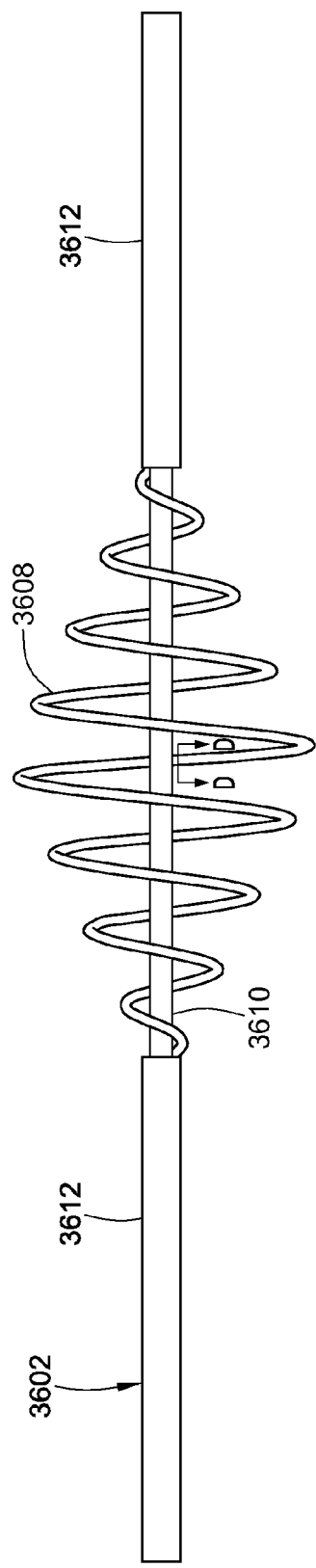
Figure 33E:
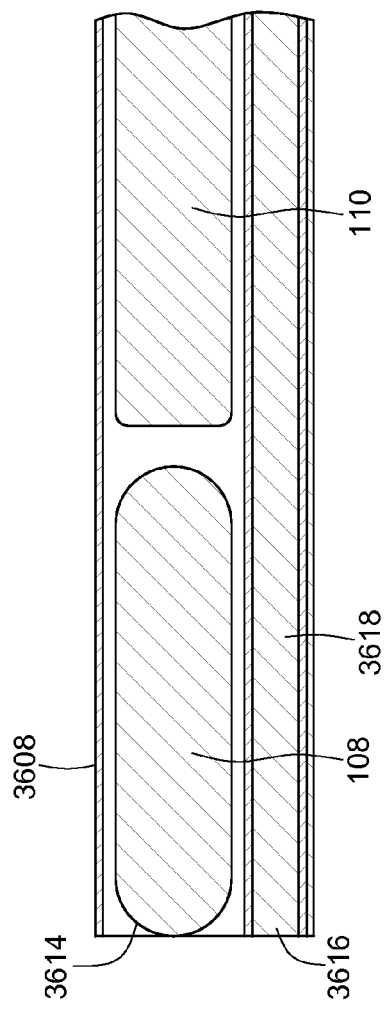
Figure 33D:
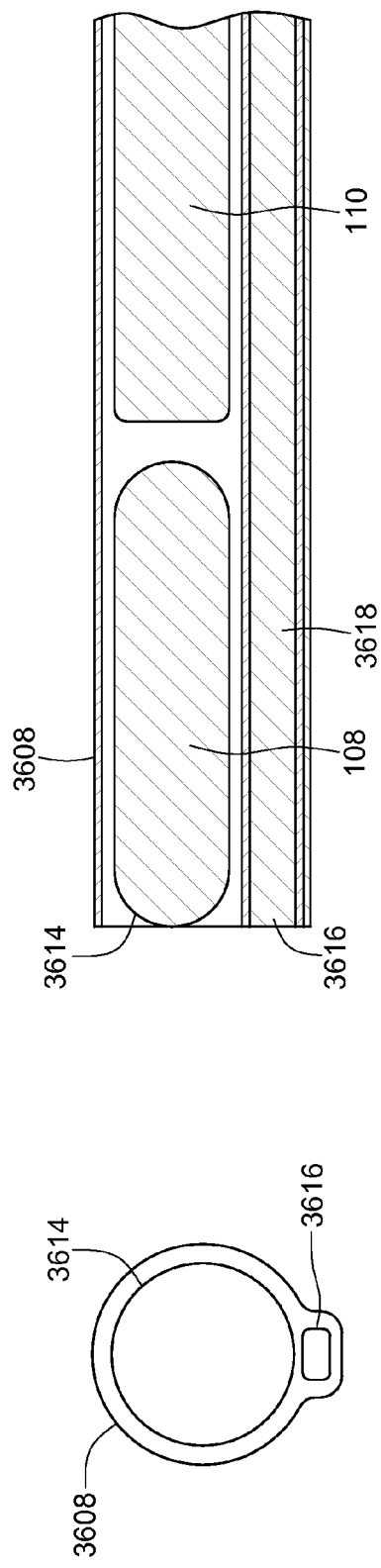

FIG. 33C is an enlarged view of the device 3602 when it is in a partially deployed position. FIG. 33D illustrates a cross section of the radioactive coil member 3608 taken normal to a central longitudinal axis of the coil member 3608 (e.g., taken along line D-D of FIG. 33C), while FIG. 33E illustrates a cross section taken along the longitudinal axis of the coil member 3608. As can be seen in these views, in one embodiment, the coil member 3608 may be an elongate tube having both a first lumen 3614 and a second lumen 3616 that extend through the elongate tube between the sleeves 3612. The first lumen 3614 may house a radiation source, e.g., a series of radioactive seeds 108 that may be offset from one another by optional spacers 110, as shown in FIG. 33E. The second lumen 3616 may contain a shaping and/or stiffening member, such as shaping wire 3618. The shaping wire 3618 may provide stiffness and twisting resistance to the coil member 3608. In the illustrated embodiment, the shaping wire 3618 (and thus the second lumen 3616) is rectangular in cross section as shown in FIG. 33D. The rectangular shape provides desirable twisting resistance to the radioactive source 3608 during deployment, e.g., it keeps the first lumen 3614 positioned outwardly from the core member 3610 during deployment. However, other shapes are certainly possible without departing from the scope of the invention.

The elongate tube that forms the coil member 3608 may be made from various materials. For example, in one embodiment, the elongate tube is made from extruded fluoropolymers or thermoplastics similar to the materials described previously with respect to the member 2906.

The shaping wire 3618 may be made from most any material that can accommodate the helical deployment without undue twisting or permanent deformation. Exemplary materials for the shaping wire include shaped memory alloys such as nitinol or the like.

Figure 33G:
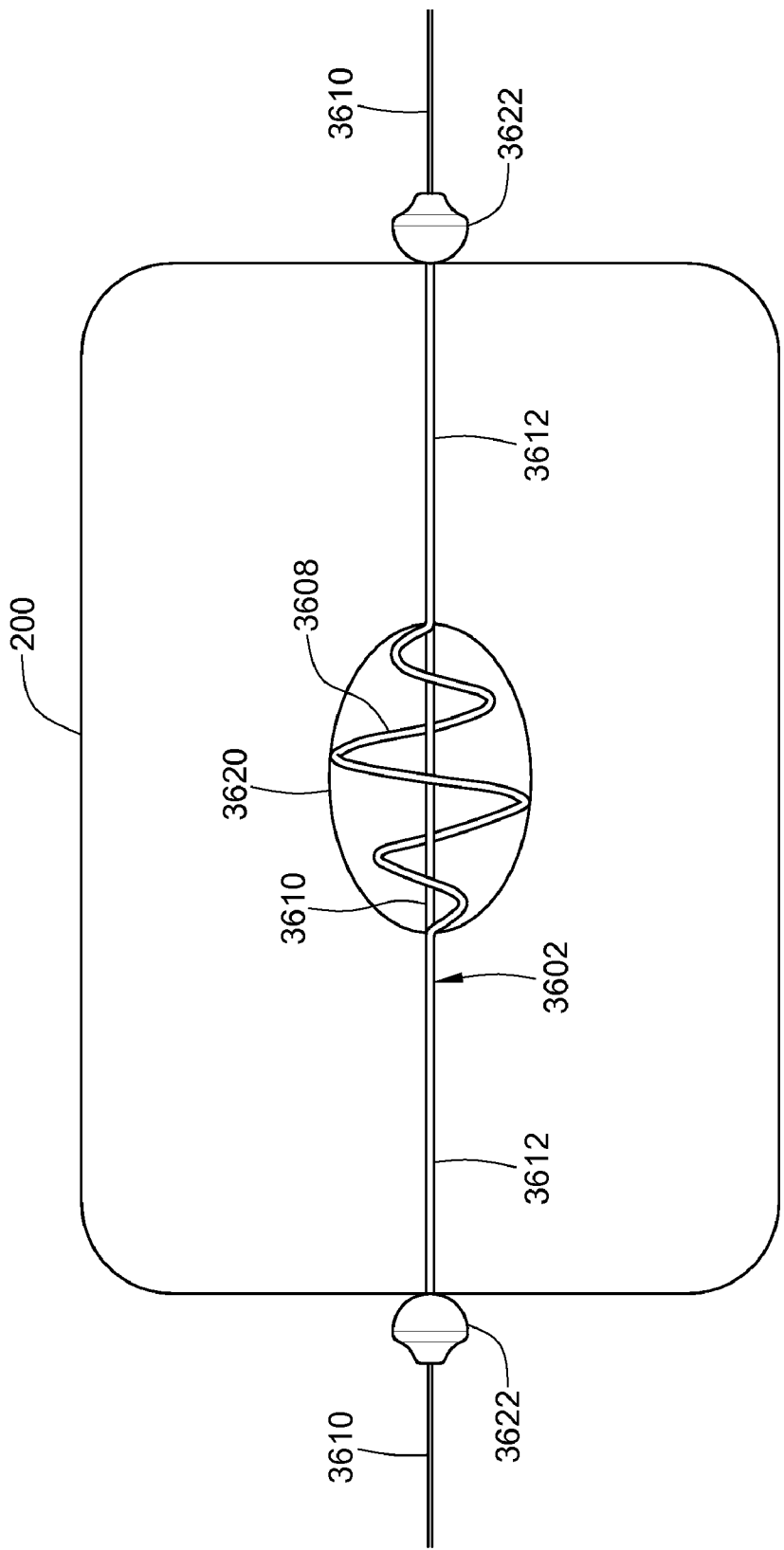

In operation, the device 3602 may be inserted through a tissue structure, e.g., breast 200, while the therapy delivery portion 3604, e.g., coil member 3608, is collapsed along the longitudinal axis of the apparatus 3600. The coil member 3608 may be inserted until it is generally centered in the lumpectomy cavity 3620 as shown in FIG. 33F. The device 3602 may enter through an existing incision (e.g., an incision made at the time of lumpectomy), or it may be placed via a hollow needle (not shown), e.g., as described elsewhere herein with respect to other embodiments. Once the device 3602 is generally in place as shown in FIG. 33F, the physician may manipulate (e.g., twist and/or axially displace) the sleeves 3612 that now protrude from each side of the breast 200 to deploy the device 3602. FIG. 33G illustrates the device 3602 as it may be configured when fully deployed within cavity 202. In an exemplary embodiment, the device 3602 may deploy such that the helical coil member 3608 pushes into the cavity walls as already discussed herein (see, e.g., FIGS. 32D-32G) to secure the apparatus 3600 relative to the surrounding tissue.

To secure the device 3602 in place, the physician may fold the sleeves 3612 that extend outside the body against the skin and secure them, e.g., with tape. Alternatively, locking members 3622 may be slid over the ends of the core member 3610. Each locking member 3622 may frictionally engage its respective sleeve 3612 as well as the core member 3610. By securing the sleeves 3612 relative to the core member 3610, the device 3602 may be generally held in place for the course of treatment.

While illustrated herein as utilizing proximal and/or distal sleeves that may protrude outside the body during implantation, other configurations may utilize sleeves that do not protrude. In this case, a tool, e.g., hollow needle (not shown), may be inserted over the core member to mechanically engage the sleeves and manipulate them as desired (from outside the body) relative to the core member.

Figure 34:
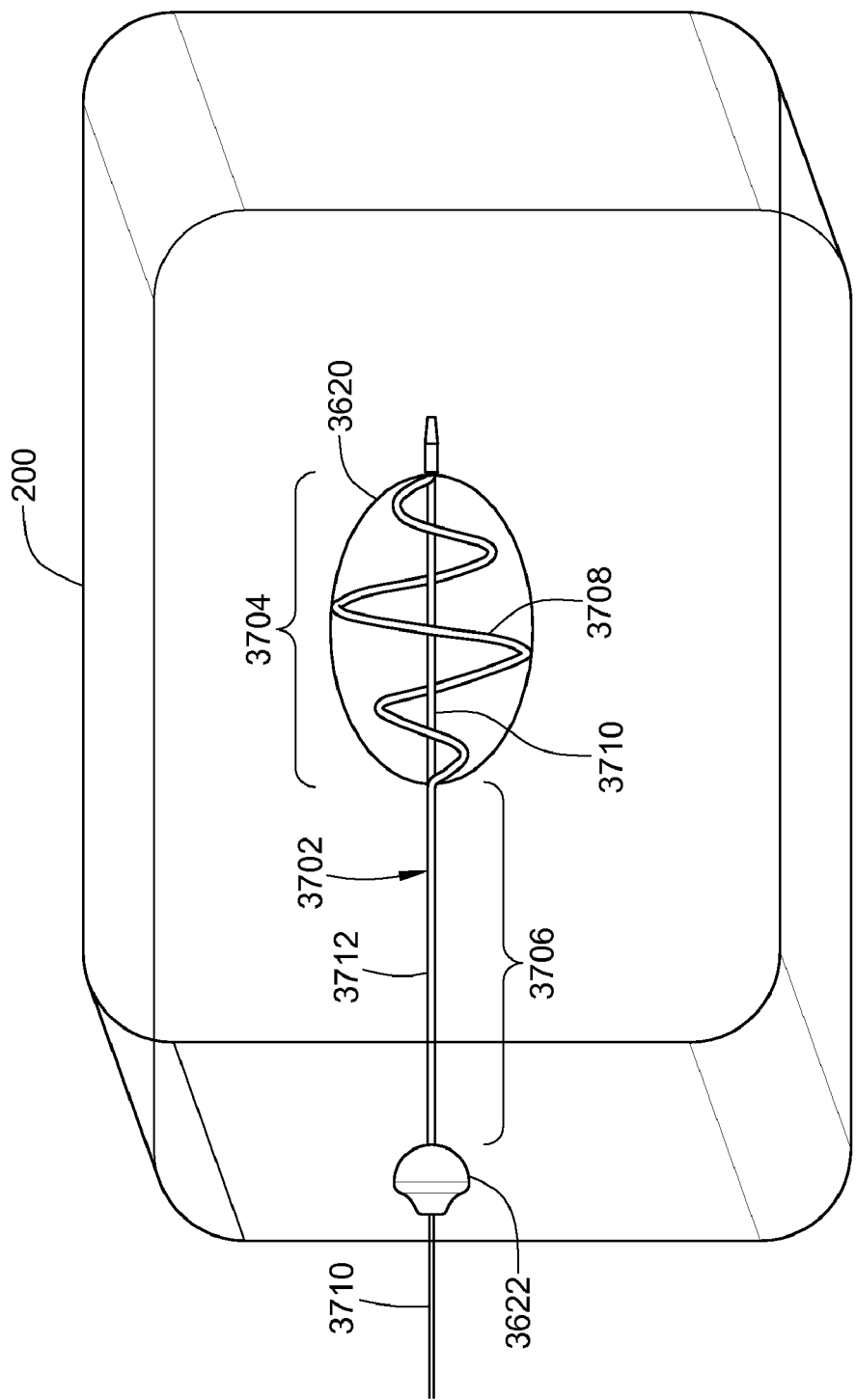
FIG. 34 illustrates a brachytherapy apparatus in accordance with still yet another embodiment, wherein the apparatus is deployed within a target tissue region.

FIG. 34 illustrates a single entry point variation of a brachytherapy device 3702, similar to the device 3602 illustrated in the immediately preceding figures. In this embodiment, a brachytherapy device 3702 is provided having a therapy delivery portion 3704 and a single tail portion 3706. The therapy delivery portion 3704 may be configured as a coil member 3708 substantially similar in construction to the coil member 3608 described above (e.g., helically wound around a core member 3710). The tail portion 3706 may also be formed by a sleeve 3712 similar in most respects to the sleeves 3612 described above. For example, the sleeve member 3712, which may be coupled to a proximal end of the radioactive source 3608, is operable to slide and/or rotate about the core member 3710.

Unlike the device 3602, a distal end of the coil member 3708 may be attached directly to the core member 3710 at or near its distal end as shown in FIG. 34 such that manipulation of the portion of the core member 3710 located outside the body will effect movement of the distal end of the radioactive source.

In operation, the device 3702 may be inserted, while in a collapsed configuration, through the body (e.g., the breast 200) such that the therapy delivery portion 3704 (e.g., coil member 3708) is positioned within the lumpectomy cavity 3620. The device 3702 may enter through an existing incision (e.g., made at the time of lumpectomy) or, it may be placed via a needle (not shown), e.g., as described elsewhere herein with respect to other embodiments. Once the device 3702 is generally in place as shown in FIG. 34, the physician may manipulate both the sleeve 3712 and the core member 3710 that both protrude from a proximal side of the breast 200. That is, axial displacement of the sleeve 3712 towards the distal end of the core member 3710 while rotating the core member 3710 (which is fixed to the distal end of the coil member 3708) may deploy central portions of the coil member 3708 away from the core member 3710 to an expanded configuration, as shown in FIG. 34 (once again, the device 3702 may expand into the tissue as already described herein, see, e.g., FIGS. 32D-32F). The device 3702 may be secured in the deployed configuration in the same manner as described above with respect to the device 3602, e.g., with locking member 3622.

It should be understood that, just as apparatus 3100 includes an inner array of elements 3106b and an outer array of elements 3106a, an alternate embodiment of the apparatus 3600/3700 may also include an inner coiled member (not shown) along with outer coiled member 3608. In both cases, these dual layer devices allow for an additional radial layer of radiation to be delivered. When combined with tissue invagination, these dual layers provide multiple shells or layers of dose clouds that may enshroud a significant thickness of breast tissue that curves around a given lumpectomy cavity.

The apparatus described herein may permit brachytherapy devices (or other radiation sources), via a single point of entry, to deliver radiation to the tissue surrounding a cavity from a position within the cavity. Moreover, the intracavitary apparatus, methods, and systems described herein may permit substantial fixation of one or more radioactive sources relative to the target tissue surrounding the cavity. The surrounding tissue may invaginate sufficiently around the devices to ensure adequate fixation and/or sufficient depth of penetration of the desired radiation dose to the tissue adjacent the lumpectomy cavity throughout the implantation period. As a result, the desired dose delivery to specific tissue may be achieved over the course of brachytherapy treatment. Moreover, irradiation of unintended tissue—due to movement of the device relative to the surrounding tissue—may be minimized.

The brachytherapy devices described herein may be implanted into (and/or around) a tumor before surgical excision (neoadjuvantly), and then subsequently removed before or at the time of surgery. Such treatments may shrink or even destroy the tumor. In other embodiments, the apparatus and methods described herein may be used to deliver brachytherapy after surgically removing tumor tissue to treat surrounding tissue post-operatively (post-lumpectomy in breast). In some instances, it is contemplated that brachytherapy apparatus and methods described and illustrated herein may supplement or reduce the need for conventional treatment options, e.g., tumor excision, full field external beam radiation therapy (EBRT), and chemotherapy. Alternatively, the methods described herein may be performed adjuvantly with these and other treatments, e.g., with chemotherapy, EBRT.

Treatment in accordance with the present invention may also avoid some of the disadvantages of HDR treatment, e.g., high activity, exposure of unintended tissue, potentially bulky and protruding catheters, and/or the need for numerous patient visits to receive treatment. Alternatively, the apparatus and methods described herein may be used to perform HDR treatment, e.g., by delivering one or more HDR radiation sources along pathways of the devices in accordance with known HDR dose plans. In a further alternative, a HDR radiation source (e.g., an Iridium tipped afterloader cable from Varian Medical Systems, Inc., or a small diameter x-ray source, such as those disclosed in U.S. Publication No. 2005/0061533A1, the disclosure of which is expressly incorporated by reference herein) may be advanced through any of the core members described herein, with the expandable devices opening a cavity to facilitate delivering radiation more evenly to the tissue surrounding the cavity. Optionally, the core member may shield the radiation source to direct radiation from the radiation source towards a desired portion of the surrounding tissue.

The brachytherapy devices described herein are also substantially flexible, in comparison to conventional HDR catheters, such that they may be placed in either a straight or curvilinear (e.g., curved or spiral) fashion. Such flexibility may permit implantation of radiation sources (e.g., seeds) in configurations and locations that otherwise may be considered inaccessible.

Apparatus and methods of the present invention may also potentially achieve desired dosage with relatively few catheters. For example, the apparatus and methods described herein potentially may obtain desired dose delivery levels with fewer catheters per target than is typically utilized with conventional HDR methods. Yet, the devices described herein may still be implanted with the use of conventional imaging methods (e.g. stereotactic X-ray, ultrasound, CT).

Apparatus and methods of the present invention may also provide other benefits to the patient. For example, potentially less skin damage and discomfort may result from smaller and more flexible catheter insertions. Further, the small flexible tail portions, once in their proper position, may be trimmed short, but may also be folded and taped against the skin, unlike rigid HDR catheters. Thus, the patient may have less discomfort over the course of treatment and potentially improved post-procedural cosmesis. Further, for example, apparatus and techniques in accordance with the present invention may potentially result in reduced side effects as compared to other treatments, e.g., EBRT and chemo, and may require fewer hospital visits over the course of the treatment regimen as compared to, for example, current HDR brachytherapy.

Still further, the brachytherapy delivery systems described herein may provide a standardized dose of radiation based upon lesion size. As a result, the need for extensive dose calculating and mapping systems may potentially be reduced or eliminated with certain cancers (e.g., breast).

The complete disclosure of the patents, patent documents, and publications cited in the Background, the Detailed Description of Exemplary Embodiments, and elsewhere herein are incorporated by reference in their entirety as if each were individually incorporated. Additional information on brachytherapy apparatus and methods may be found in co-pending application Ser. Nos. 10/658,518, filed Sep. 9, 2003, 60/731,879, filed Oct. 31, 2005, and 60/735,532, filed Nov. 10, 2005, the entire disclosures of which are expressly incorporated by reference herein.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the treatment devices described herein may be combined with any of the delivery systems and methods also described herein. Thus, the invention is limited only by the following claims, and equivalents thereto.

We claim:

1. A brachytherapy treatment apparatus for treating tissue surrounding a cavity within a body, comprising:
    an elongate body comprising a proximal end and a distal end configured for introduction into a tract through tissue, the elongate body comprising a core member and a body member, the core member and body member comprising mating threads for causing the body member to move axially relative to the core member when the body member is rotated relative to the core member;
    a plurality of elongate members on the distal end comprising pathways for receiving a source of radiation therealong, the elongate members including distal ends coupled to the core member and proximal ends coupled to the body member, the elongate members being movable from a collapsed configuration for introduction through a tissue tract to a target location, and an expanded configuration for providing a three dimensional array of pathways at the target location;
    a source of radiation introduceable along the pathways for delivering radiation to the target location; and
    an actuator coupled to one of the core member and body member, the actuator rotatable in a first direction for moving the body member axially relative to the core member to move the elongate members from the collapsed configuration to the expanded configuration and rotatable in a second opposite direction to move the elongate members from the expanded configuration to the collapsed configuration, at least a portion of the actuator being detachable from the elongate body to reduce a profile of the brachytherapy delivery apparatus after implantation, the detachable portion and the elongate body comprising releasable connectors for allowing the detachable portion to be removed after implantation.

2. The brachytherapy treatment apparatus of claim 1, the elongate members being spaced apart in the expanded configuration such that tissue at the target location invaginates between the elongate members.

3. The brachytherapy treatment apparatus of claim 1, further comprising a hub coupled to proximal ends of the elongate members and the body member, the hub being movable axially as the body member is moved axially relative to the core member for moving the elongate members from the collapsed configuration to the expanded configuration.

4. The brachytherapy treatment apparatus of claim 3, wherein the core member is coupled to distal ends of the elongate members, and wherein the hub comprises an outer member coupled to proximal ends of the elongate members, the outer member slidably disposed around the elongate body.

5. The brachytherapy treatment apparatus of claim 4, wherein the outer member comprises passageways communicating with the pathways of the elongate members.

6. The brachytherapy treatment apparatus of claim 3, wherein the hub comprises a plurality of openings communicating with respective pathways for introducing the source of radiation along the pathways.

7. The brachytherapy treatment apparatus of claim 3, wherein the hub comprises one or more indicia for identifying respective pathways of the elongate members.

8. The brachytherapy treatment apparatus of claim 1, wherein each of the elongate members comprises a stiffening member for maintaining the elongate members in a desired orientation when the elongate members are moved from the collapsed configuration to the expanded configuration.

9. The brachytherapy treatment apparatus of claim 1, wherein the source of radiation comprises a plurality of pods carrying radioactive elements that may be introduced along respective pathways of the elongate members.

10. The brachytherapy treatment apparatus of claim 1, wherein the source of radiation comprises a radiation generating device that is introduceable sequentially along each of the pathways of the elongate members.

11. The brachytherapy treatment apparatus of claim 10, wherein the radiation generating device comprises an HDR source of radiation.

12. The brachytherapy treatment apparatus of claim 1, wherein the distal end of the elongate body is sharpened to penetrate through tissue.

13. The brachytherapy treatment apparatus of claim 1, wherein the elongate members comprise tubular members comprising lumens defining the pathways.

14. A brachytherapy treatment apparatus for treating tissue surrounding a cavity within a body, comprising:
    an elongate body comprising a proximal end and a distal end sized for introduction into a tract through tissue, the elongate body comprising a core member and a body member surrounding a portion of the core member, the core member and body member comprising mating threads for causing the body member to move axially relative to the core member when the body member is rotated relative to the core member;
    a plurality of tubular members on the distal end comprising lumens for receiving a source of radiation therein, the tubular members being movable from a collapsed configuration for introduction through a tissue tract to a target location, and an expanded configuration for providing a three dimensional array of pathways at the target location;
    a plurality of openings communicating with respective lumens for inserting the source of radiation into the lumens;
    a hub coupled to proximal ends of the tubular members and the body member, the hub being movable axially as the body member is moved axially relative to the core member for moving the tubular members from the collapsed configuration to the expanded configuration; and
    an actuator coupled to one of the core member and body member, the actuator rotatable in a first direction for moving the body member axially relative to the core member to move the tubular members from the collapsed configuration to the expanded configuration and rotatable in a second opposite direction for collapsed the tubular members to the collapsed configuration, at least a portion of the actuator extending proximally beyond the hub being detachable from the brachytherapy apparatus to reduce a profile of the brachytherapy delivery apparatus after implantation.

15. The brachytherapy treatment apparatus of claim 14, wherein the actuator is coupled to the body member for moving the hub relative to the distal end of the elongate body for moving the tubular members between the collapsed configuration and the expanded configuration.

16. The brachytherapy treatment apparatus of claim 14, further comprising a plurality of pods carrying radioactive elements, the pods being introduceable into respective lumens of the tubular members.

17. The brachytherapy treatment apparatus of claim 14, the tubular members being spaced apart in the expanded configuration such that tissue at the target location invaginates between the tubular members.

18. The brachytherapy treatment apparatus of claim 14, wherein the tubular members comprise a three dimensional array in the expanded configuration that provides multiple layers of radiation when the source of radiation is introduced into the tubular members.

19. A brachytherapy treatment apparatus for treating tissue surrounding a cavity within a body, comprising:
an elongate body comprising a proximal end and a distal end sized for introduction into a tract through tissue;
a plurality of tubular members on the distal end comprising lumens for receiving a source of radiation therein, the tubular members being movable from a collapsed configuration wherein the elongate members extend substantially parallel to the elongate body for introduction through a tissue tract to a target location, and an expanded configuration for providing a three dimensional array of pathways at the target location;
a plurality of openings communicating with respective lumens for inserting the source of radiation into the lumens;
a proximal hub coupled to proximal ends of the tubular members, the proximal hub being movable relative to the elongate body for moving the tubular members from the collapsed configuration to the expanded configuration;
the tubular members comprising first and second sets of tubular members, the first set of tubular members spaced apart about a central axis of the elongate body such that the first set of tubular members generally define a first maximum diameter in the expanded configuration, the second set of tubular members spaced apart about the central axis such that the second set of tubular members generally define a second maximum diameter in the expanded configuration that is less than the first maximum diameter;
a distal hub coupled to a distal tip of the elongate body and distal ends of the first set of tubular members; and
a floating hub coupled to distal ends of the second set of tubular members, the floating hub contacting the distal hub after the proximal hub has been moved relative to the elongate body to cause the first set of tubular members to bow outwardly without expanding the second set of tubular members, whereupon further movement of the proximal hub relative to the elongate body causes both the first and second sets of tubular members to move outwardly towards the expanded configuration such that the second set of tubular members defines a smaller diameter than the first set of tubular members.

20. The brachytherapy treatment apparatus of claim 19, wherein the second set of tubular members is angularly offset from the first set of tubular members about the central axis.

21. The brachytherapy treatment apparatus of claim 19, wherein the second set consists of a single tubular member.

22. The brachytherapy treatment apparatus of claim 19, wherein a tubular member of the second set of tubular members is disposed between two adjacent tubular members in the first set of tubular members and closer to the central axis in the expanded configuration.

23. The brachytherapy treatment apparatus of claim 22, wherein at least one of the two adjacent tubular members in the first set of tubular members has one or more portions with no radiation source.

24. The brachytherapy treatment apparatus of claim 19, wherein the distal hub comprises a pocket that receives the floating hub when the proximal hub has been moved partially relative to the elongate body to cause the first set of tubular members to bow outwardly without expanding the second set of tubular members, thereby preventing further movement of the floating hub relative to the distal hub.

25. A brachytherapy treatment apparatus for treating tissue surrounding a cavity within a body, comprising:
an elongate body comprising a proximal end and a distal end sized for introduction into a tract through tissue, the elongate body comprising a core member and a body member surrounding a portion of the core member, the core member and body member comprising mating threads for causing the body member to move axially relative to the core member when the body member is rotated relative to the core member;
a plurality of elongate members on the distal end comprising pathways for receiving a source of radiation therealong, the elongate members being movable from a collapsed configuration for introduction through a tissue tract to a target location, and an expanded configuration for providing a three dimensional array of pathways at the target location, the elongate members being spaced apart in the expanded configuration such that tissue at the target location invaginates between the elongate members; and
an actuator coupled to one of the core member and body member, the actuator rotatable in a first direction for moving the body member axially relative to the core member to move the elongate members from the collapsed configuration to the expanded configuration and rotatable in a second opposite direction for collapsed the elongate members to the collapsed configuration, at least a portion of the actuator being detachable from the brachytherapy apparatus to reduce a profile of the brachytherapy delivery apparatus after implantation, the detachable portion and the elongate body comprising releasable connectors for allowing the detachable portion to be removed after implantation.

26. The brachytherapy treatment apparatus of claim 25, further comprising a source of radiation introduceable along the pathways for delivering radiation to the target location.

27. A method for brachytherapy treatment of tissue within a body, comprising:
creating a tract through tissue to a target location including a cavity;
advancing an elongate body carrying a plurality of elongate members through the tract into the target location with the elongate members in a collapsed configuration such that an actuator extends from the tract out of the body and the elongate body is disposed within the body, the elongate body comprising a core member and a body member, the core member and body member comprising mating threads for causing the body member to move axially relative to the core member when the body member is rotated relative to the core member;

rotating the actuator to rotate and cause the body member to move axially relative to the core member and thereby direct the elongate members to an expanded configuration at the target location to position the elongate members away from a central axis such that tissue surrounding the cavity extends between at least a portion of adjacent elongate members;

detaching at least a detachable portion of the actuator from the elongate body;

removing the detachable portion of the actuator from the body after expanding the elongate members to the expanded configuration; and delivering radiation to the target location to treat tissue at the target location.

28. The method of claim 27, wherein the elongate members secure the elongate body at the target location when the elongate members are directed to the expanded configuration.

29. The method of claim 27, wherein tissue at the target location invaginates between the elongate members when the elongate members are directed to the expanded configuration.

30. The method of claim 27, wherein the elongate members direct tissue surrounding the cavity outwardly when the elongate members are directed to the expanded configuration.

31. The method of claim 30, wherein one or more of the elongate members extend into tissue surrounding the cavity such that at least a portion of the one or more elongate members is substantially surrounded by tissue.

32. The method of claim 27, wherein one or more of the elongate members penetrate into the tissue surrounding the cavity when the elongate members are directed to the expanded configuration.

33. The method of claim 27, wherein one or more of the elongate members cut into the tissue surrounding the cavity when the elongate members are directed to the expanded configuration.

34. The method of claim 27, wherein the elongate members carry one or more radioactive elements, and wherein radiation is delivered to the target location by leaving the elongate body at the target location for a predetermined time, thereby exposing the tissue to radiation emitted by the one or more radioactive elements.

35. The method of claim 27, wherein delivering radiation to the target location comprises introducing a source of radiation along pathways provided along the elongate members.

36. The method of claim 35, wherein the source of radiation comprises an HDR radiation source that is introduced sequentially into successive pathways of the elongate members.

37. The method of claim 35, wherein the source of radiation comprises a plurality of pods that are introduced along respective pathways provided along the elongate members.

38. The method of claim 37, wherein the elongate members comprise a plurality of tubular members comprising lumens defining respective pathways, and wherein introducing a source of radiation along pathways comprises introducing pods into respective lumens.

39. The method of claim 38, wherein each pod comprises a plurality of radioactive seeds located based upon a predetermined dose plan, and wherein the pods are introduced into the respective lumens to provide a three-dimensional array that is substantially asymmetrical about the central axis.

40. The method of claim 37, wherein the pods comprise seeds, the seeds having different radioactive intensities at predetermined locations in the three dimensional array.

41. The method of claim 40, wherein the radioactive intensities of the seeds are selected to deliver a relatively lower dose of radiation to one or more regions of the target location than to other regions of the target location.

42. The method of claim 41, wherein the one or more regions comprise tissue adjacent skin of the body.

43. The method of claim 41, wherein the one or more regions correspond to one or more specific pathways of the three dimensional array.

44. The method of claim 41, wherein one or more specific pathways include no radioactive seeds.

45. The method of claim 27, wherein the elongate body comprises a sharpened distal tip, and wherein the tract is created when the elongate body is advanced through tissue to the target location.

46. The method of claim 27, further comprising:
directing the elongate members to the collapsed configuration after delivering radiation to the target location; and
removing the elongate body from the target location.

47. The method of claim 27, wherein creating the tract through tissue comprises advancing a tubular member through tissue to the target location, and wherein the elongate body is advanced through the tubular member.

48. The method of claim 47, wherein a piercing member is disposed within the tubular member when the tubular member is advanced through tissue, the piercing member comprising a sharpened distal tip extending beyond the tubular member for penetrating through tissue to create the tract, and wherein the piercing member is removed before the elongate body is advanced through the tubular member.

49. The method of claim 27, wherein the elongate members are directed towards the expanded configuration such that the elongate members contact tissue surrounding the cavity, thereby causing the tissue to invaginate between the elongate members.

50. The method of claim 27, wherein the elongate members carry a plurality of radioactive elements, and wherein the elongate members position the radioactive elements in a three dimensional array when the elongate members are directed to the expanded configuration.

51. The method of claim 50, wherein the radioactive elements define multiple layers of radiation in the expanded configuration.

52. The method of claim 50, wherein the radioactive elements are fixed to the elongate members such that the three dimensional array defined by the radioactive elements corresponds to a predetermined dose plan for treating the tissue at the target location.

53. The method of claim 27, wherein delivering radiation to the target location comprises:
determining a dose plan based upon the expanded configuration within the target location; and
delivering radiation according to the determined dose plan.

54. The method of claim 53, wherein delivering radiation according to the determined dose plan comprises introducing an HDR source sequentially along successive pathways of the elongate members.

55. The method of claim 53, wherein delivering radiation according to the determined dose plan comprises introducing a plurality of pods along respective pathways provided along the elongate members.

56. The method of claim 55, wherein a first set of the elongate members is disposed towards a relatively thin tissue region adjacent the cavity, the pods comprising a first set of pods introduced along the first set of the elongate members, the first set of pods having a lower radiation intensity than other pods.

57. The method of claim 56, wherein the first set of the elongate members comprises an outer layer of pathways, and wherein a second set of the elongate members is disposed below the first set of the elongate members such that second set of the elongate members comprises an inner layer of pathways in the expanded configuration.

58. The method of claim 56, wherein the first set comprises a pair of adjacent elongate members, and wherein the second set comprises an elongate member disposed between the pair of adjacent elongate members and closer to a central axis of the elongate body.

59. The method of claim 27, further comprising removing at least a portion of the actuator after directing the elongate members to the expanded configuration at the target location to reduce a profile of the actuator extending from the body after implantation.

* * * * *